United States Patent
Graupe et al.

(10) Patent No.: US 7,030,116 B2
(45) Date of Patent: *Apr. 18, 2006

(54) COMPOUNDS AND COMPOSITIONS AS CATHEPSIN INHIBITORS

(75) Inventors: Michael Graupe, Pacifica, CA (US); James T. Palmer, Corte Madera, CA (US); John W. Patterson, Mountain View, CA (US); David J. Aldous, Gillette, NJ (US); Sukanthini Thurairatnam, Bedminster, NJ (US); Andreas P. Timm, Morristown, NJ (US); John Link, San Francisco, CA (US); Jiayao Li, San Bruno, CA (US)

(73) Assignees: Aventis Pharmaceuticals Inc., Bridgewater, NJ (US); Axys Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/183,128

(22) Filed: Jun. 26, 2002

(65) Prior Publication Data
US 2003/0105099 A1    Jun. 5, 2003

Related U.S. Application Data

(63) Continuation-in-part of application No. 10/035,783, filed on Dec. 24, 2001.

(60) Provisional application No. 60/257,603, filed on Dec. 22, 2000.

(51) Int. Cl.
A61K 31/535    (2006.01)

(52) U.S. Cl. ............. 514/237.5; 514/231.5; 544/137; 544/138; 544/124; 544/127; 544/141; 544/160

(58) Field of Classification Search ............. 544/137, 544/138, 124, 127, 141, 160; 514/231.5, 514/233.8, 237.5
See application file for complete search history.

(56) References Cited

U.S. PATENT DOCUMENTS

| | | | |
|---|---|---|---|
| 4,927,809 A | 5/1990 | Stuber et al. | |
| 5,424,325 A | 6/1995 | Ando et al. | |
| 5,486,623 A | 1/1996 | Zimmerman et al. | |
| 5,498,616 A | 3/1996 | Mallano et al. | |
| 5,847,135 A | 12/1998 | Bemis et al. | |
| 5,852,007 A | 12/1998 | Chatterjee et al. | |
| 5,874,424 A | 2/1999 | Batchelor et al. | |
| 5,998,390 A | 12/1999 | Ramamurthy et al. | |
| 6,004,933 A | 12/1999 | Spruce et al. | |
| 6,015,791 A | 1/2000 | Gyorkos et al. | |
| 6,022,861 A | 2/2000 | Scarborough et al. | |
| 6,114,310 A | 9/2000 | Chamberland et al. | |
| 6,124,333 A | 9/2000 | Miller et al. | |
| 6,255,453 B1 | 7/2001 | Gyorkos et al. | |
| 6,313,117 B1 * | 11/2001 | Bekkall et al. | ......... 514/235.5 |
| 6,353,017 B1 | 3/2002 | Altman et al. | |
| 6,455,502 B1 | 9/2002 | Bryant et al. | |
| 6,476,026 B1 | 11/2002 | Bryant et al. | |
| 6,492,362 B1 | 12/2002 | Graupe et al. | |
| 6,506,733 B1 | 1/2003 | Buysse | |
| 6,576,630 B1 | 6/2003 | Link et al. | |
| 6,608,057 B1 | 8/2003 | Cywin et al. | |

FOREIGN PATENT DOCUMENTS

| | | |
|---|---|---|
| EP | 0272671 | 6/1988 |
| EP | 0355572 | 2/1990 |
| EP | 0376012 | 7/1990 |
| EP | 0419683 | 4/1991 |
| EP | 0536399 | 4/1993 |
| EP | 0652009 | 10/1995 |
| EP | 0754454 | 1/1997 |
| EP | 0291234 | 11/1998 |
| JP | 42009133 | 5/1967 |
| JP | 63303868 | 12/1988 |
| JP | 06192199 | 7/1994 |
| JP | 2001-011037 | 1/2001 |
| JP | 2001-055366 | 2/2001 |
| WO | WO 95/13069 | 5/1995 |
| WO | WO 95/15309 | 6/1995 |
| WO | WO 95/24382 | 9/1995 |
| WO | WO 96/21655 | 7/1996 |
| WO | WO 96/30353 | 10/1996 |
| WO | WO 96/40647 | 12/1996 |
| WO | WO 96/40744 | 12/1996 |
| WO | WO 96/41638 | 12/1996 |
| WO | WO 97/03679 | 2/1997 |
| WO | WO 98/01133 | 1/1998 |
| WO | WO 98/01428 | 1/1998 |
| WO | WO 98/05336 | 2/1998 |
| WO | WO 98/08802 | 3/1998 |
| WO | WO 98/08867 | 3/1998 |
| WO | WO 98/21188 | 5/1998 |
| WO | WO 98/23588 | 6/1998 |
| WO | WO 98/49190 | 11/1998 |

(Continued)

OTHER PUBLICATIONS

U.S. Appl. No. 10/294,526, filed Nov. 14, 2002, Li, et al.
U.S. Appl. No. 10/719,080, filed Nov. 21, 2003, Graupe, et al.
U.S. Appl. No. 10/787,367, filed Sep. 16, 2002, Graupe, et al.
U.S. Appl. No. 10/418,183, filed Oct. 23, 2003, Li, et al.

(Continued)

*Primary Examiner*—Taofiq Solola
*Assistant Examiner*—Robert Shiao
(74) *Attorney, Agent, or Firm*—Joseph D. Rossi

(57) ABSTRACT

The present invention relates to novel cathepsin S inhibitors, the pharmaceutically acceptable salts and N-oxides thereof, their uses as therapeutic agents and the methods of their making.

9 Claims, No Drawings

FOREIGN PATENT DOCUMENTS

| WO | WO 99/24460 | 5/1999 |
|---|---|---|
| WO | WO 00/48992 | 8/2000 |
| WO | WO 00/49007 | 8/2000 |
| WO | WO 00/49008 | 8/2000 |
| WO | WO 00/51998 | 9/2000 |
| WO | WO 00/59881 | 10/2000 |
| WO | WO00/59881 | 10/2000 |
| WO | WO 00/69855 | 11/2000 |
| WO | WO 01/09110 | 2/2001 |
| WO | WO01/09169 | 2/2001 |
| WO | WO 01/19796 | 3/2001 |
| WO | WO 01/19808 | 3/2001 |
| WO | WO 01/19816 | 3/2001 |
| WO | WO 01/30772 | 5/2001 |
| WO | WO 01/55125 | 8/2001 |
| WO | WO 01/58886 | 8/2001 |
| WO | WO02/20485 | 3/2002 |
| WO | WO02/096892 | 5/2002 |
| WO | WO 02/051983 | 7/2002 |
| WO | WO02/057248 | 7/2002 |
| WO | WO02/057249 | 7/2002 |
| WO | WO02/057270 | 7/2002 |
| WO | WO02/100849 | 12/2002 |

OTHER PUBLICATIONS

Adams, et al., Potent and Selective Inhibitors of the Proteasom: Dipeptidyl Boronic Acids, Bioorganic & Medicinal Chemistry Letters, 8: 333-338 (1998).

Ashworth, et al., 4-Cyanothiazolidides as very potent stable inhibitors of dipeptidyl peptidase IV, Bioorganic & Med. Chem. Letters, B,Oxford, 6(22):2745-2748 (1996).

Bergeman, et al., Studies on the reactivity of .alpha.-cyano.alpha-isocyano alkanoates. Versitile synthons for the assembly of imidazoles, Helv.Chim. ACTA, 82(6):909-918 (1999).

Billson, et al., The Design and Synthesis of Inhibitors of the Cysteinyl , Bioorg. Med. Chem. Lett. vol. 8, pp. 993-998, 1998.

Bromme, et al., Potent Inactivation of Cathepsins S and L , Biol. Chem. Hoppe—Seyler. vol. 375, No. 5, pp. 343-347, 1994.

Chatterjee, et al., D-Amino Acid Containing, High-Affinity Inhibitors of Recombinant Human Calpain I, Journal of Medicinal Chemistry, vol. 41, No. 15, p: 2663-2666 (1998).

Cohen, et al., Therapy of relapsing multiple sclerosis. Treatment approaches for nonresponders, Journal of Neuroimmunology, 98: 29-36 (1999).

Dufour, et al., Engineering nitrile hydratase activity into a cysteine protease by a single mutation, Bio.chemistry, US, Am. Chem. Soc., Easton, PA, 34(50):16382-16388 (1995).

Edwards, et al., Design, Synthesis, and Kinetic Evaluation of a Unique Class of Elastase Inhibitors, the Peptidyl a-Ketobenzoxazoles, and the X-ray Crystal Structure of the Covalent Complex between Porcine Pancreatic Elastase and Ac-Ala-Pro-Val-2-Benzoxazole, Journal of American Chemical Society, vol. 114, No. 5, p 1854-1863 (1992).

Evoli, et al., abstract only, Drugs, 1996, 52(5), 662-70.

Gour-Salin, et al., Inhibition of papain by peptide nitriles: conversion of the nitrile group into other functionalities via the papain:nitrile thiomidate ester adduct, Can. J. of Chem, CA, National Research Council. Ottawa, 69(8):1288-1297 (1991).

Hallegua, et al., Cyclosporine for lupus membranous nephritis: experience with ten patients and review of the literature, Lupus, 9: 241-251 (2000).

Hanzlik, et al., Reversible covalent binding of peptide nitriles to papain, Biochim. Biophys, Acta, vol. 1035, No. 1, 1990, pp. 62-70.

Harris, et al., Characteristics of a continuous fluorogenic assay for calpain I. Kinetic evaluation of peptide aldehydes, halomethyl ketones and )achalasia) methyl ketones as inhibitors of the enzyme, Chemical Abstracts, 110:7, Bioorg. Med. Chem. Lett, 5(4) 393-398 (1995).

Heitmiller, R.F., abstract only., Semin. Thorac. Cardiovasc. Surg., 1999, 11(1), 41-6.

Katritzky, et al., Benzotriazole-assisted synthesis of alpha.-(acylamino) nitrites and a conceptually novel method for peptide elongation, Chem. Soc., Perkin Trans. 1(7):1853-1857 (1990).

Khamashta, et al., Expert. Opin. Investig. Drugs, 2000, 9(7), 1581-93.

Krantz, et al., Peptidyl (Acyloxy)methyl Ketones and the Quiescent , Biochemistry. vol. 30, pp. 4678-4687, 1991.

Levy, E.G., Baillieres Clin. Endocrinol. Metab., 1997, 11(3) 585-595.

Li, et al., Aminoacylpyrrolidine-2-nitriles: Potent and stable inhibitors of dipeptidyl-peptidase IV (CD 26), Archives of Biochem. and Bioph., 323(1)148-154 (1995).

Lipshutz, et al., Chiral induction in orginally racemic amino acids via 5-acyl and 5-acyloxyaminooxazolas, lsr, J. Chem. 27(1):49-55 (1986), abstract.

Lipshutz, et al., Heterocycles as masked diamide/dipeptide equivalents. Formation and reactions of substituted 5-(acylamino)oxazoles as intermediates en route to the cyclopeptide alkaloids, . Am. Chem. Soc., 105(26):7703-7713 (1983).

Lipshutz, et al., Oxazolophanes as masked cyclopeptide alkaloid equivalents: cyclic peptide chemistry without peptide couplings, J. Am. Chem. Soc., 112(19):7032-7041 (1990).

Marquis, et al., Potent dipeptidylketone inhibitors of the cysteine protease cathepsin, Chemical Abstracts, 7:4 581-588 (1999).

McMath, et al., Direct dialkylation of peptide nitriles. Application of the synthesis of 1-aminocyclopropane-1 carboxylic acid (Acc)-containing dipeptides, Bull. Soc. Chim. Fr. 134(1):105-110 (1997).

Moriya, et al., Synthesis and Hypolipidemic Activities of 5-Thienyl-4-oxazoleacetic Acid Derivatives.sup.1, J. Med. Chem., 29: 333-341 (1986).

Moser, et al., 130 Poly (dipeptamidinium)-Salze: definition und metoden zur praparativen herstellung. poly (dipeptamidinium) salts: definition and methods of preperation, Helvitica Chimica ACTA, CH, Verlag, Basel 69:1224-1262 (1986).

Nippon, K., Patent Abstracts of Japan, Publication No. 63301868, 013(137)(1988), abstract.

North, et al., Synthetic studies towards cyclic peptides. Concise synthesis of thiazoline and thiazole containing amino acids, Tetrahedron, 46(24):8627-8290 (1990).

Ogilvie, et al., Peptidomimetic inhibitors of the human cytomegalovirus protease, Journal of Medicinal Chemistry vol. 40 No. 25 (1997).

Picken, et al., Inhibition of bovine cathepsin B by amino acid-derived nitriles, Biochemical Society Transactions, vol. 18, No. 2, p:316 (1990).

Pliura, et al., Comparative behavior of colpain and cathepsin B, Biochem. J. vol. 288, pp. 759-762, 1992.

Polman, et al., Drug treatment of multiple sclerosis , BMJ, 312: 19-26 (2000).

Riese, et al., Essential Role for Cathesin S in MHC Class II-Associated Invariant Chain Processing and Peptide Loading, Immunity, 4: 357-366 (Apr. 1996).

Smith, et al., New Inhibitors of Cysteine Proteinases, J. Am. Chem. Soc. vol. 110, No. 13, pp. 4429-4431, 1988.

Suave, et al., Carboxylmodified amino acids and peptides, I An efficient method for the synthesis of monofunctionalized enamines and monofunctionalized methyl ketone derivatives fom thioamides via episulfides and thioiminium salts, Tetrahedron Lett, 29:19 2295-2298 (1988).

Suzue, S., Hepatic agents. I. Synthesis of aminocyl (and hydroxyacyl) aminoacetonitriles, Chem. and Pharm. Bull. (Tokyo) (1968), 16(8), 1417-32.

Suzue, et al., Studies on Heptic Agents, Chem. Pharm. Bull. vol. 16, No. 8, pp. 1417-1432, Aug. 1968.

Suzuki, et al., Synthesis of 2-Aryl-4(3-thienyl)imidazole Derivatives with Antinflammatory Properties .sup.1), Chem. Pharm. Bull, 34(8): 3111-3120 (1996).

Tao, et al., Inhibition of Calpain By Peptidyl Heterocycles, Bioorganic & Medicinal Chemnistry Letters, 6:24 3009-3112 (1996).

Thompson, et al., Carboxyl-modified amino acids and peptides as protease inhibitors, J. Med. Chem., 29(1):104-111 (1986).

Tsutsumi, et al., Synthesis and Structure-Activity Relationships of Peptidyl a-Keto Heterocycles as Novel Inhibitors of Prolyl Endopeptidase, Journal of Medicinal Chemistry, vol. 37, No. 21, p 3492-3502 (1994).

Vargha, E., Peptide derivatives. VI. N-protected di- and tripeptide nitriles, Stud. Univ. Babes-Bolyai, Ser. Chem., 13(2):31-5 (English abstract of article in Romanian) (1968).

Varghese, The structure and resonance Raman spectra—structure correlations for methyloxycarbonyl-L-phenylatanyl-L-alanine ethyl dithioester, Can. J. Chem., 64(8):1668-1673 (1986).

Yamada, et al., Studies of unusual amino acids and their peptides. IX. The synthetic study of bottomycins B1 and B2, Bul. Chem. Soc., Jpn. 51(3):878-83 (1978), abstract.

Derwent Abstract of Japanese Patent Application 06-192199, (Jul. 12, 1994).

U.S. Appl. No. 09/927,188, filed Aug. 10, 2001, Cai, et al.
U.S. Appl. No. 09/927,324, filed Aug. 10, 2001, Butler, et al.
U.S. Appl. No. 09/928,122, filed Aug. 10, 2001, Breitenbucher, et al.
U.S. Appl. No. 09/946,214, filed Sep. 5, 2001, Gu, et al.
U.S. Appl. No. 10/042,565, filed Nov. 16, 2001, Quibell, et al.
U.S. Appl. No. 10/148,612, filed Aug. 21, 2002, Ohmoto, et al.
U.S. Appl. No. 10/148,613, filed Aug. 28, 2002, Ohmoto, et al.
U.S. Appl. No. 10/181,713, filed Jul. 22, 2002, Ohmoto, et al.
U.S. Appl. No. 10/181,799, filed Jul. 23, 2002, Ohmoto, et al.
U.S. Appl. No. 10/231,426, filed Aug. 28, 2002, Buxton, et al.
U.S. Appl. No. 10/256,512, filed Sep. 27, 2002, Bekkali, et al.
U.S. Appl. No. 10/258,053, filed Oct. 17, 2002, Cummings, et al.
U.S. Appl. No. 10/275,583, filed Nov. 7, 2002, Cowen, et al.
U.S. Appl. No. 10/279,424, filed Oct. 24, 2002, Bekkali, et al.
U.S. Appl. No. 10/468,385, filed Jan. 8, 2004, Quibell, et al.

Chapman, et al., Emerging Roles for Cysteine Proteases In Human Biology, Ann. Rev. Physiol.; 1997; 59; pp. 83-88.

Dranoff, et al., Cathepain S Required for Normal MHC Class II Peptide Loading and Germinal Center Development, Immunity; 1999; 10; pp. 197-208.

Fenwick, et al., Diastereoselective Synthesis, Activity and Chiral Stability of Cyclic Alkoxyketone Inhibitors of Cathepsin K., Bioorg. Med. Chemm. Lett.; 2001; 11(2); pp. 199-202.

Fenwick, et al., Solid-phase Synthesis of Cyclic Alkoxyketones, Inhibitors of the Cysteine Protease Cathepsin K., Bioorg. Med. Chem. Lett.; 2001; 11(2); pp. 195-198.

Greenspan, et al., Identification of Dipeptidyl Nitriles as Potent and Selective Inhibitors of cathepsin B Through Structure-based Drug Design, J. Med. Chem.; 2001; 44; pp. 4524-4534.

Lowe, et al., Kinetic Specificity in Papain-catalyzed Hydrolyses, Biochem. J.; 1971; 124(1); pp. 107-115.

Maciewicz, et al., A comparison of Four Cathepsins (B,L,N and S) with Collagenolytic Activity From Rabbit Spleen, Biochem J.; 1996; 256; pp. 433-440.

Marquis, et al., Azeanone-based Inhibitors of Human and Rat Cathepsin K., J. Med. Chem.; 2000; 44(9); pp. 1380-1395.

Nakagawa, et al., Imparied Invariant Chain Degradation and Antigen Presentation and Diminished Collagen-induced Arthritis in Cathepsin S-null Mice, Immunity; 1999; 10; pp. 207-217.

Otto, et al., Cysteine Proteases and their inhibitors, Chem. Rev.; 1997; 97; pp. 133-171.

Shi, et al., Molecular Cloning and Expression of Human Alveolar Macrophage Cathepsin S, an Elastinolytic Cysteine Protease, J. Biol. Chem.; 1992; 267; pp. 7258-7262.

Singh, et al., beta-lactams as Enzyme Inhibitors., IDrugs; 2000; 9(5); pp. 512-517.

Villadangos, et al., Cathepsin S Activity Regulates Antigen Presentation and Immunity, J. Clin. Invest.; 1998; 101(10); pp. 2351-2363.

* cited by examiner

COMPOUNDS AND COMPOSITIONS AS CATHEPSIN INHIBITORS

This application is a continuation-in-part of U.S. patent application Ser. No. 10/035,783, filed on Dec. 24, 2001, which claims priority from U.S. Provisional Application 60/257,603 filed on Dec. 22, 2000. The two applications, Ser. Nos. 10/035,783 and 60/257,603, are incorporated herein by reference.

THE INVENTION

This application relates to compounds and compositions for treating diseases associated with cysteine protease activity, particularly diseases associated with activity of cathepsin S and the processes of making the compounds.

DESCRIPTION OF THE FIELD

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. An increase in cathepsin S activity contributes to the pathology and/or symptomatology of a number of diseases. Accordingly, molecules that inhibit the activity of cathepsin S protease are useful as therapeutic agents in the treatment of such diseases.

SUMMARY OF THE INVENTION

This application relates to compounds that inhibit the enzymatic activity of Cathapsin S and have a backbone structure of formula I, II or III:

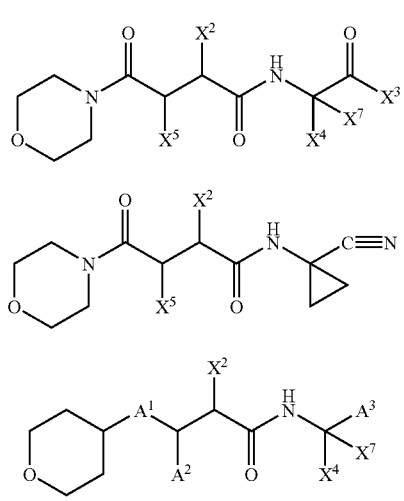

where
$A^1$ is —O—, —N(R)— or —SO$_2$—;
$A^2$ is —H, —F, —OH, or —O—R;
$A^3$ is —C(O)—$X^3$ or cyano; and
$X^2$, $X^3$, $X^4$, $X^5$, $X^7$ and R are chemical groups or radicals.

The compounds of the present invention also include closely related isomers and derivatives that are made from the compounds of the above Formulae. They include, but not limited to, the N-oxide derivatives, prodrug derivatives, protected derivatives, individual isomers and mixture of isomers of the compounds, and the pharmaceutically acceptable salts and solvates of such compounds. For the purpose of this application, "a related chemical entity" of Formula I, II or III means an N-oxide derivative, a produg derivative, a protected derivative, an individual isomer, a mixture of isomers, or a pharmaceutically acceptable salt or solvate, of a compound of Formula I, II or III.

In one aspect of the present invention, the inventive point is the backbone structures of Formulae I and II themselves, wherein the substituents at the $X^2$, $X^3$, $X^4$, $X^5$ and $X^7$ positions can be any chemical groups or radicals which may be substituted at those positions (or general substituents as defined hereinafter), including those substitutions made possible by any conventional means or by any new technologies developed in the future. For the purpose of this application, a substituent stated in a claim that does not serve as a claim element or limitation of the claim is referred to as a "general substituents."

In another aspect of the invention, the inventive point is the backbone structures of Formula I and II plus popular substituents at the $X^2$, $X^3$, $X^4$, $X^5$ and $X^7$ positions. For the purpose of this application, "a popular substituent" means a chemical group or radical which people of ordinary skill in the art, by using the specific substitutions disclosed hereinafter as guidance, would deem practical to substitute at $X^2$, $X^3$, $X^4$, $X^5$ or $X^7$ without undue experimentation in practicing the present invention.

In another aspect of the invention, the inventive point is the backbone structures of Formula I and II plus specific substituents disclosed hereinafter at the $X^2$, $X^3$, $X^4$, $X^5$ and $X^7$ positions.

Another aspect of the invention is a compound of Formula III, wherein $A^1$ is —O—, —N(R)— or —SO$_2$—, $A^2$ is —H, —F, —OH, or —O—R, $A^3$ is cyano or —C(O)—$X^3$, and $X^2$, $X^3$, $X^4$, $X^7$ and R are general substituents.

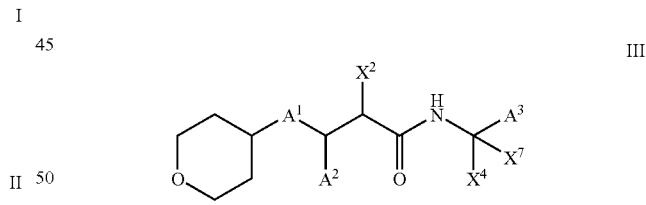

Another aspect of the invention is a method for treating a disease in an animal in which inhibition of cathepsin S can prevent, inhibit or ameliorate the pathology and/or symptomatology of the disease, which method comprises administering to the animal a therapeutically effective amount of a compound of the present invention.

Another aspect of the invention are the processes for preparing compounds of Formulae I, II and III.

Definitions:

"Isomers", as used in this disclosure, mean compounds of Formulae I, II and III having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound, which has one chiral-center has two enantiomeric forms of opposite chirality. A "racemic mixture" contains both enantiomers as a 1:1 ratio. However, in terms of this application a racemic mixture has been employed when both enantiomers were present irrespective of their ratios. A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustrations used in this disclosure to describe compounds of Formulae I, II, and III are meant to encompass all possible stereoisomers. Thus, for example, the name 2-cyclohexylmethyl-N-[1-(5-ethyl-1,2,4-oxadiazole-3-carbonyl)-propyl]-4-morpholin-4-yl-4-oxo-butyramide is meant to include (R)-2-cyclohexylmethyl-N-[(S)-1-(5-ethyl-1,2,4-oxadiazole-3-carbonyl)-propyl]-4-morpholin-4-yl-4-oxo-butyramide and (S)-2-Cyclohexylmethyl-N-[(R)-1-(5-ethyl-1,2,4-oxadiazole- 3-carbonyl)-propyl]-4-morpholin-4-yl-4-oxo-butyramide and any mixture, racemic or otherwise, thereof.

"N-oxide derivatives" means derivatives of compounds of Formulae I, II and III in which nitrogens are in an oxidized state (i.e., N—O) and which possess the desired pharmacological activity.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formulae I, II and III which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methylsulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound which is convertible in vivo by metabolic means to a compound of Formula I, II or III. For example an ester of a compound of Formula I, II or III containing a hydroxy group may be convertible by hydrolysis in vivo to the parent molecule. Alternatively an ester of a compound of Formula I, II or III containing a carboxy group may be convertible by hydrolysis in vivo to the parent molecule. Suitable esters of compounds of Formulae I, II and III containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formulae I, II and III containing a carboxy group are, for example, those described by F. J. Leinweber, Drug Metab. Res., 1987, 18, page 379. An especially useful class of esters of compounds of Formulae I, II and III containing a hydroxy group, may be formed from acid moieties selected from those described by Bundgaard et al., J. Med. Chem., 1989, 32, page 2503–2507, and include substituted (aminomethyl)-benzoates, for example, dialkylamino-methylbenzoates in which the two alkyl groups may be joined together and/or interrupted by an oxygen atom or by an optionally substituted nitrogen atom, e.g., an alkylated nitrogen atom, more especially (morpholino-methyl)benzoates, e.g., 3- or 4-(morpholinomethyl)-benzoates, and (4-alkylpiperazin-1-yl)benzoates, e.g., 3- or 4-(4-alkylpiperazin-1-yl)benzoates.

"Protected derivatives" means derivatives of compounds of Formulae I, II and III in which a reactive site or sites are blocked with protecting groups. Protected derivatives of compounds of Formulae I, II and III are useful in the preparation of compounds of Formulae I, II and III or in themselves may be active cathepsin S inhibitors. A comprehensive list of suitable protecting groups can be found in T. W. Greene, *Protecting Groups in Organic Synthesis*, 3rd edition, John Wiley & Sons, Inc., 1999.

"Therapeutically effective amount" means that amount which, when administered to an animal for treating a disease, is sufficient to effect such treatment for the disease.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

Nomenclature:

The compounds of Formulae I, II and III and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 4.0 (Beilstein Information Systems, Inc.). For example, a compound having the following structure:

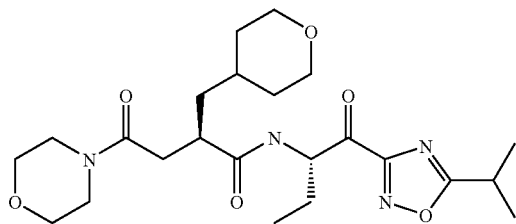

is named (R)-N-[(S)-1-(5-isopropyl-1,2,4-oxadiazole-3-carbonyl)-propyl]-4-morpholin-4-yl-4-oxo-2-(tetrahydro-pyran-4-ylmethyl)-butyramide However, it is understood that, for a particular compound referred to by both a structural formula and a nomenclature name, if the structural formula and the nomenclature name are inconsistent with each other, the structural formula takes the precedence over the nomenclature name.

The various features of novelty which characterize the invention are pointed out with particularity in the claims annexed to and forming a part of this disclosure. For a better understanding of the invention, its operating advantages, and specific objects attained by its use, reference should be made to the following description in which there are illustrated and described preferred embodiments of the invention.

DETAILED DESCRIPTION OF THE PREFERRED EMBODIMENTS

Preferred Compounds:

One particular group of compounds, as preferred embodiments of the present invention, are compounds of Formulae I, II and III,

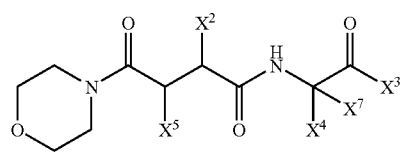

I

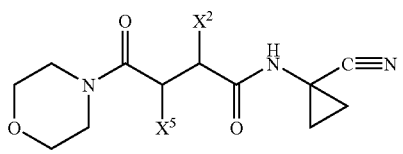

II

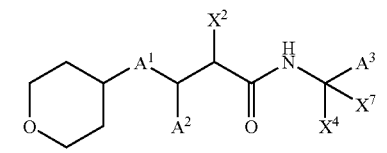

III wherein:
$X^2$ is a substituted alkyl motif or a sulfonyl alkyl motif;
$X^3$ is a heterocyclic motif or an amide motif;
$X^4$ and $X^7$ are independently —H, —R or

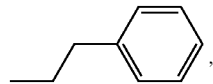

or $X^4$ and $X^7$ taken together with the carbon atom to which both $X^4$ and $X^7$ are attached form a 3–6 membered cycloalkyl group;
$X^5$ is —H, —F, —OH or —O—R;
$A^1$ is —O—, —N(R)— or —SO$_2$—;
$A^2$ is —H, —F, —OH, or —O—R;
$A^3$ is cyano or —C(O)—$X^3$; and
R is an alkyl group with straight or branched-chain containing 1–6 carbon atoms.

For the purpose of this application, a heterocyclic motif is:

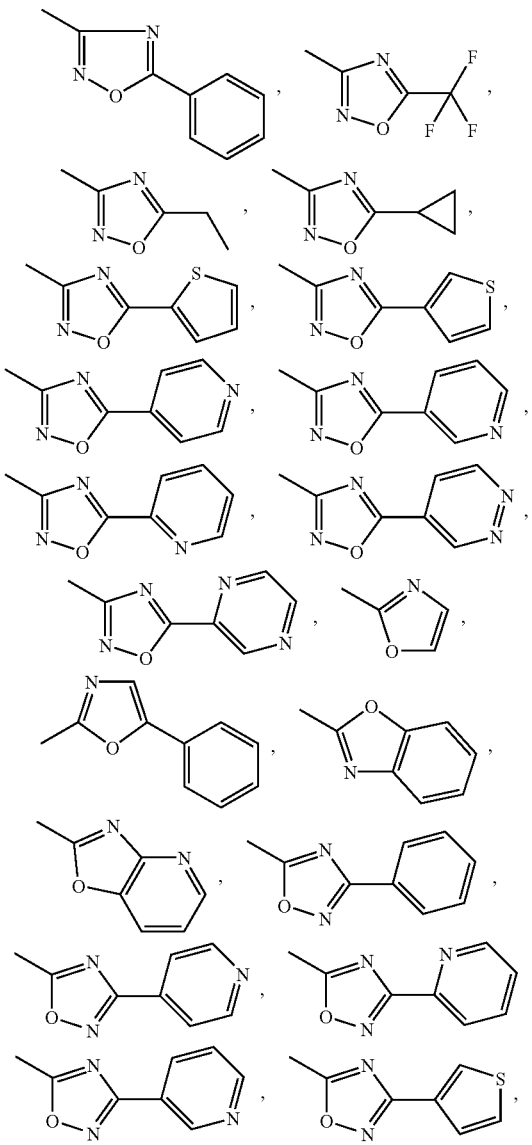

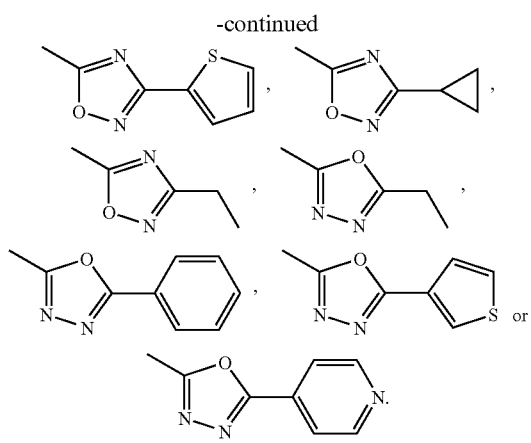
For the purpose of this application, an amide motif is
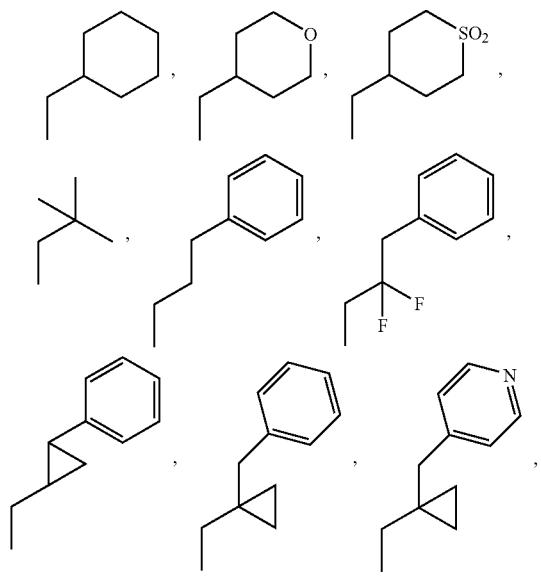
For the purpose of this application, a substituted alkyl motif is:
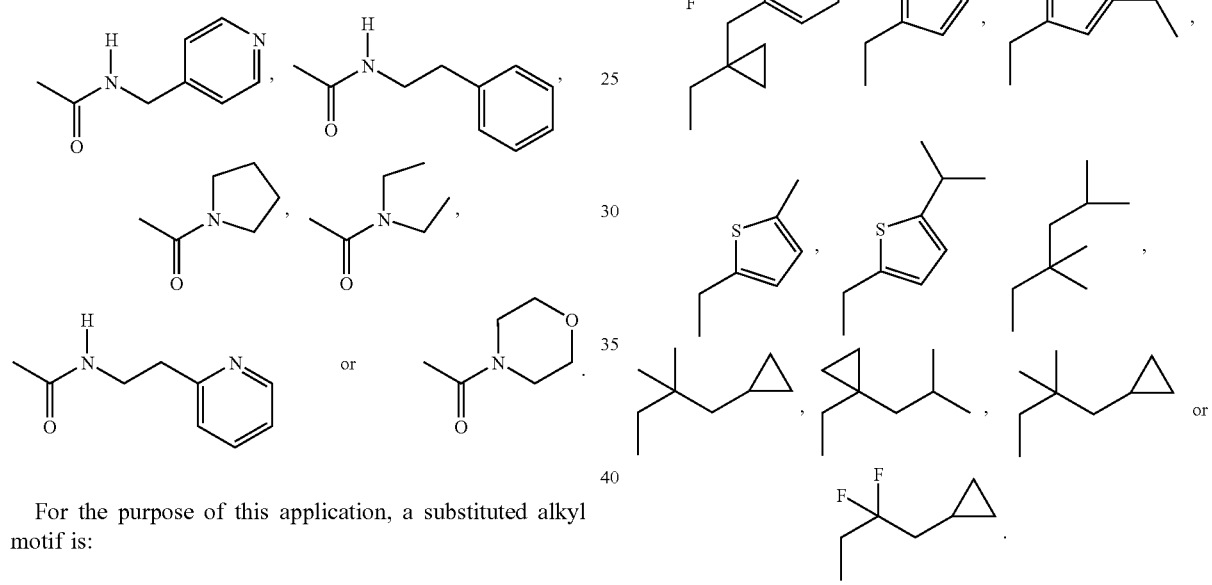
For the purpose of this application, a sulfonyl alkyl motif is:
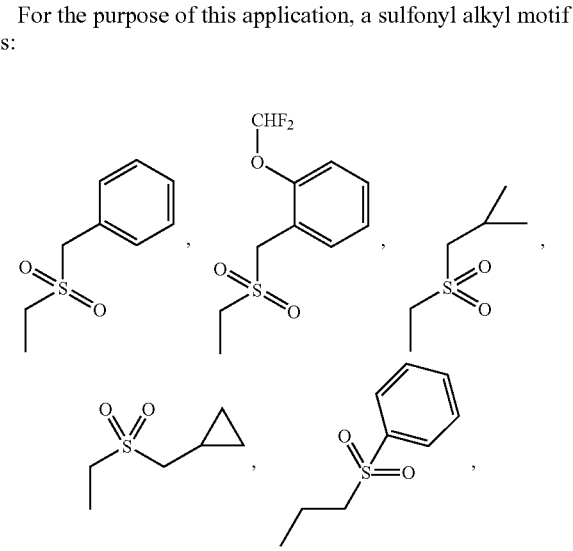

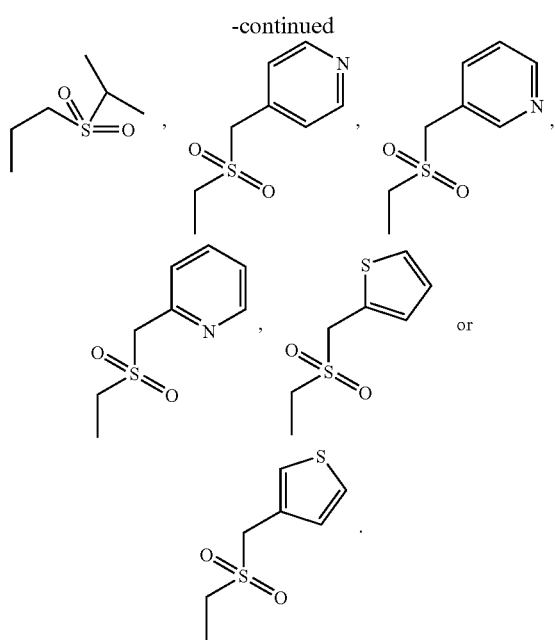

This group of preferred embodiments also encompasses their related chemcial entities as defined above.

Further preferred embodiments are the following compounds:

2-(2-Methyl-propane-1-sulfonylmethyl)-4-morpholin-4-yl-4-oxo-N-[(S)-1-(5-phenyl-1,2,4-oxadiazole-3-carbonyl)-propyl]-butyramide, (R)-2-Cyclohexylmethyl-4-morpholin-4-yl-4-oxo-N-[(S)-1-(5-trifluoromethyl-1,2,4-oxadiazole-3-carbonyl)-propyl]-butyramide, (R)-4,4-Dimethyl-2-(2-morpholin-4-yl-2-oxo-ethyl)-pentanoic acid[(S)-1-(5-trifluoromethyl-1,2,4-oxadiazole-3-carbonyl)-propyl]-amide, 4-Morpholin-4-yl-4-oxo-2-phenylmethanesulfonylmethyl-N-[(S)-1-(5-trifluoromethyl-1,2,4-oxadiazole-3-carbonyl)-propyl]-butyramide, (R)-2-(2-Methyl-propane-1-sulfonylmethyl)-4-morpholin-4-yl-4-oxo-N-[(S)-1-(3-phenyl-1,2,4-oxadiazole-5-carbonyl)-propyl]-butyramide, N-[(S)-1-(5-Ethyl-1,2,4-oxadiazole-3-carbonyl)-propyl]-4-morpholin-4-yl-4-oxo-2-phenylmethanesulfonylmethyl-butyramide, (R)-4-Morpholin-4-yl-4-oxo-2-phenylmethanesulfonylmethyl-N-[(S)-1-(3-phenyl-1,2,4-oxadiazole-5-carbonyl)-propyl]-butyramide, (R)-4-Morpholin-4-yl-4-oxo-2-phenylmethanesulfonylmethyl-N-[1-(3-phenyl-1,2,4-oxadiazole-5-carbonyl)-propyl]-butyramide, 4,4-Dimethyl-2-(2-morpholin-4-yl-2-oxo-ethyl)-pentanoic acid[1-(5-ethyl-1,2,4-oxadiazole-3-carbonyl)-propyl]-amide, (R)-2-Cyclohexylmethyl-N-[(S)-1-(5-ethyl-1,2,4-oxadiazole-3-carbonyl)-propyl]-4-morpholin-4-yl-4-oxo-butyramide, N-[(S)-1-(Benzoxazole-2-carbonyl)-butyl]-2-(1-benzyl-cyclopropylmethyl)-4-morpholin-4-yl-4-oxo-butyramide, N-[(S)-1-(Benzoxazole-2-carbonyl)-butyl]-4-morpholin-4-yl-4-oxo-2-(2-phenyl-cyclopropylmethyl)-butyramide, (R)-4,4-Dimethyl-2-(2-morpholin-4-yl-2-oxo-ethyl)-pentanoic acid[(S)-1-(benzoxazole-2-carbonyl)-butyl]-amide, (R)-4,4-Dimethyl-2-(2-morpholin-4-yl-2-oxo-ethyl)-pentanoic acid[1-(3-phenyl-1,2,4-oxadiazole-5-carbonyl)-propyl]-amide, (R)-4,4-Dimethyl-2-(2-morpholin-4-yl-2-oxo-ethyl)-5-phenyl-pentanoic acid[1-(3-phenyl-1,2,4-oxadiazole-5-carbonyl)-propyl]-amide, 4,4-Dimethyl-2-(2-morpholin-4-yl-2-oxo-ethyl)-5-phenyl-pentanoic acid[(S)-1-(benzoxazole-2-carbonyl)-butyl]-amide, (R)-4,4-Dimethyl-2-(2-morpholin-4-yl-2-oxo-ethyl)-5-phenyl-pentanoic acid[(S)-1-(5-ethyl-1,2,4-oxadiazole-3-carbonyl)-propyl]-amide, (R)-4,4-Dimethyl-2-(2-morpholin-4-yl-2-oxo-ethyl)-5-phenyl-pentanoic acid[(S)-1-(5-trifluoromethyl-1,2,4-oxadiazole-3-carbonyl)-propyl]-amide, (R)-2-(1-Benzyl-cyclopropylmethyl)-N-[(S)-1-(5-ethyl-1,2,4-oxadiazole-3-carbonyl)-propyl]-4-morpholin-4-yl-4-oxo-butyramide, (R)-5-(2-Difluoromethoxy-phenyl)-4,4-dimethyl-2-(2-morpholin-4-yl-2-oxo-ethyl)-pentanoic acid[(S)-1-(5-ethyl-1,2,4-oxadiazole-3-carbonyl)-propyl]-amide, (S)-N-[(S)-1-(Benzoxazole-2-carbonyl)-butyl]-2-(5-methyl-thiophen-2-ylmethyl)-4-morpholin-4-yl-4-oxo-butyramide, (R)-N-[(S)-1-(Benzoxazole-2-carbonyl)-butyl]-2-(1-benzyl-cyclopropylmethyl)-4-morpholin-4-yl-4-oxo-butyramide, (R)-5-(2-Difluoromethoxy-phenyl)-4,4-dimethyl-2-(2-morpholin-4-yl-2-oxo-ethyl)-pentanoic acid[(S)-1-(benzoxazole-2-carbonyl)-butyl]-amide, 2-(2-Morpholin-4-yl-2-oxo-ethyl)-5-phenyl-pentanoic acid [(S)-1-(oxazole-2-carbonyl)-3-phenyl-propyl]-amide (mixture of diastereoisomers), 4-Morpholin-4-yl-N-[1-(oxazole-2-carbonyl)-3-phenyl-propyl]-4-oxo-2-(2-phenyl-cyclopropylmethyl)-butyramide (mixture of diastereoisomers), (R)-2-Cyclohexylmethyl-4-morpholin-4-yl-N-[(S)-1-(oxazole-2-carbonyl)-3-phenyl-propyl]-4-oxo-butyramide, (R)-4,4-Dimethyl-2-(2-morpholin-4-yl-2-oxo-ethyl)-pentanoic acid[(S)-1-(5-phenyl-1,2,4-oxadiazole-3-carbonyl)-propyl-amide, 3-Phenylmethanesulfonyl-N-[(S)-1-(5-phenyl-1,2,4-oxadiazole-3-carbonyl)-propyl]-2-(tetrahydro-pyran-4-yloxymethyl)-propionamide, (R)-4,4,6-Trimethyl-2-(2-morpholin-4-yl-2-oxo-ethyl)-heptanoic acid[(S)-1-(5-ethyl-1,2,4-oxadiazole-3-carbonyl)-propyl]-amide, (R)-4,4,6-Trimethyl-2-(2-morpholin-4-yl-2-oxo-ethyl)-heptanoic acid[(S)-1-(oxazole-2-carbonyl)-propyl]-amide, (R)-4,4,6-Trimethyl-2-(2-morpholin-4-yl-2-oxo-ethyl)-heptanoic acid[(S)-1-(benzoxazole-2-carbonyl)-butyl]-amide, (R)-2-((S)-1-Hydroxy-2-morpholin-4-yl-2-oxo-ethyl)-5-phenyl-pentanoic acid[(S)-1-(oxazole-2-carbonyl)-3-phenyl-propyl]-amide, (S)-2-(1-Fluoro-2-morpholin-4-yl-2-oxo-ethyl)-5-phenyl-pentanoic acid[(S)-1-(benzoxazole-2-carbonyl)-butyl]-amide, (R)-2-((S)-1-Methoxy-2-morpholin-4-yl-2-oxo-ethyl)-5-phenyl-pentanoic acid[(S)-1-(benzoxazole-2-carbonyl)-butyl]-amide, (R)-N-[(S)-1-(3-Cyclopropyl-1,2,4-oxadiazole-5-carbonyl)-propyl]-2-(2-methyl-propane-1-sulfonylmethyl)-4-morpholin-4-yl-4-oxo-butyramide, (R)-2-Cyclopropylmethanesulfonylmethyl-N-[(S)-1-(3-cyclopropyl-1,2,4-oxadiazole-5-carbonyl)-propyl]-4-morpholin-4-yl-4-oxo-butyramide, (R)-4,4-Dimethyl-2-(2-morpholin-4-yl-2-oxo-ethyl)-5-phenyl-pentanoic acid[(S)-1-(3-cyclopropyl-1,2,4-oxadiazole-5-carbonyl)-propyl]-amide, (R)-2-(1-Benzyl-cyclopropylmethyl)-N-[(S)-1-(3-cyclopropyl-1,2,4-oxadiazole-5-carbonyl)-propyl]-4-morpholin-4-yl-4-oxo-butyramide, (R)-4,4,6-Trimethyl-2-(2-morpholin-4-yl-2-oxo-ethyl)-heptanoic acid[(S)-1-(3-cyclopropyl-1,2,4-oxadiazole-5-carbonyl)-propyl]-amide, (R)-5-Cyclopropyl-4,4-dimethyl-2-(2-morpholin-4-yl-2-oxo-ethyl)-pentanoic acid[(S)-1-(3-cyclopropyl-1,2,4-oxadiazole-5-carbonyl)-propyl]-amide, (R)-N-[(S)-1-(3-Cyclopropyl-1,2,4-oxadiazole-5-carbonyl)-propyl]-2-(1-isobutyl-cyclopropylmethyl)-4-morpholin-4-yl-4-oxo-butyramide, (R)-2-(1-Cyclopropylmethyl-cyclopropylmethyl)-N-[(S)-1-(3-cyclopropyl-1,2,4-oxadiazole-5-carbonyl)-propyl]-4-morpholin-4-yl-4-oxo-butyranide, (R)-N-[(S)-1-(3-Ethyl-1,2,4-oxadiazole-5-carbonyl)-propyl]-2-(2-methyl-propane-1-sulfonylmethyl)-4-morpholin-4-yl-4-oxo-butyramide, (R)-2-Cyclopropylmethanesulfonylmethyl-N-[(S)-1-(3-ethyl-1,2,4-oxadiazole-5-carbonyl)-propyl]-4-morpholin-4-yl-4-oxo-butyramide, (S)-2-(2-Benzenesulfonyl-ethyl)-N-[(S)-1-(3-ethyl-1,2,4-oxadiazole-5-carbonyl)-propyl]-4-morpholin-4-yl-4-oxo-butyramide, (S)-N-[(S)-1-(3-Ethyl-1,2,4-oxadiazole-5-carbonyl)-propyl]-4-morpholin-4-yl-4-oxo-2-[2-(propane-2-sulfonyl)-ethyl]-butyramide, 2-(1-Methyl-cyclopentylmethyl)-4-morpholin-4-yl-N-[-(oxazolo[4,5-b]pyridine-2-carbonyl)-propyl]-4-oxo-butyramide, (S)-3-(4-Morpholin-4-yl-4-oxo-2-phenylmethanesulfonylmethyl-butyrylamino)- 2-oxo-pentanoic acid (pyridin-4-ylmethyl)-amide, (S)-3-(4-Morpholin-4-yl-4-oxo-2-phenylmethanesulfonylmethyl-butyrylamino)-2-oxo-pentanoic acid diethylamide, N-((S)-1-Ethyl-2,3-dioxo-3-pyrrolidin-1-yl-propyl)-4-morpholin-4-yl-4-oxo-2-phenylmethanesulfonylmethyl-butyramide, (S)-3-(4-Morpholin-4-yl-4-oxo-2-phenylmethanesulfonylmethyl-butyrylamino)-2-oxo-pentanoic acid phenethylamide, (S)-3-(4-Morpholin-4-yl-4-oxo-2-phenylmethanesulfonylmethyl-butyrylamino)-2-oxo-pentanoic acid (2-pyridin-2-yl-ethyl)-amide, N-(1-Cyano-cyclopropyl)-4-morpholin-4-yl-4-oxo-2-phenylmethanesulfonylmethyl-butyramide, and their related chemical entities.

Pharmacology and Utility:

The compounds of the invention are inhibitors of cathepsin S and, as such, are useful for treating diseases in which cathepsin S activity contributes to the pathology and/or symptomatology of the disease. For example, the compounds of the invention may be useful in treating autoimmune disorders, including, but not limited to, juvenile onset diabetes, multiple sclerosis, pemphigus vulgaris, Graves' disease, myasthenia gravis, systemic lupus erythemotasus, irritable bowel disease, rheumatoid arthritis and Hashimoto's thyroiditis, allergic disorders including but not limited to, asthma, and allogeneic immune responses, including, but not limited to, organ transplants or tissue grafts.

Cathepsin S is also implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibrinl formation and, therefore, inhibitors of cathepsins S may be of use in treatment of systemic amyloidosis.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Examples 46, 47, 48, 49, infra.

Administration and Pharmaceutical Compositions:

In general, compounds of the present invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of the invention may range from about 1 micrograms per kilogram body weight (µg/kg) per day to about 60 milligram per kilogram body weight (mg/kg) per day, typically from about 1 µg/kg/day to about 20 mg/kg/day. Therefore, a therapeutically effective amount for a 80 kg human patient may range from about 80 µg/day to about 4.8 g/day, typically from about 80 µg/day to about 1.6 g/day. In general, one of ordinary skill in the art, acting in reliance upon personal knowledge and the disclosure of this Application, will be able to ascertain a therapeutically effective amount of a compound of the invention for treating a given disease.

The compounds of the invention can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of the invention in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of the invention in the composition may vary widely depending upon the type of formulation, size of a unit dosage, kind of excipients and other factors known to those of skill in the art of pharmaceutical sciences. In general, a composition of a compound of the invention for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of the invention are described in Example 50.

Chemistry:

Processes for Making Compounds of the Invention:

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of the invention can be prepared by proceeding according to Reaction Scheme 1:

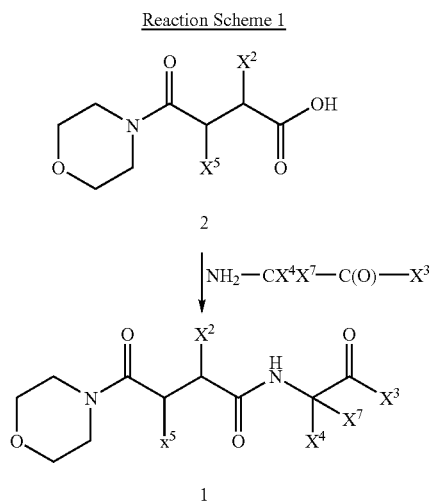

where each $X^2$, $X^3$, $X^4$, and $X^5$ are as defined for Formula I in the Summary of the Invention.

As indicated in the scheme, compounds of Formula I can be prepared by condensing an acid of Formula 2 with an amino compound of the formula $NH_2CX^4X^7-C(O)-X^3$. The condensation reaction can be effected with an appropriate coupling agent (e.g., benzotriazol-1-yloxytrispyrrolidinophosphonium hexafluorophosphate (PyBOP®), 1-(3-dimethylaminopropyl)-3-ethylcarbodiimide hydrochloride (EDCI), O-benzotriazol-1-yl-N,N,N',N'-tetramethyluroniumhexafluorophosphate (HBTU), 1,3-dicyclohexylcarbodiimide (DCC), O-(7-azabenzotrizol-1-yl)-1,1,3,3,tetramethyluroniumhexafluorophosphate (HATU), or the like) and optionally an appropriate catalyst (e.g., 1-hydroxybenzotriazole (HOBt), 1-hydroxy-7-azabenzotriazole (HOAt), or the like) and non-nucleophilic base (e.g., triethylamine, N-methylmorpholine, and the like, or any suitable combination thereof) at ambient temperature and requires 1 to 10 hours to complete.

Compounds of the invention can be prepared by proceeding according to Reaction Scheme 2:

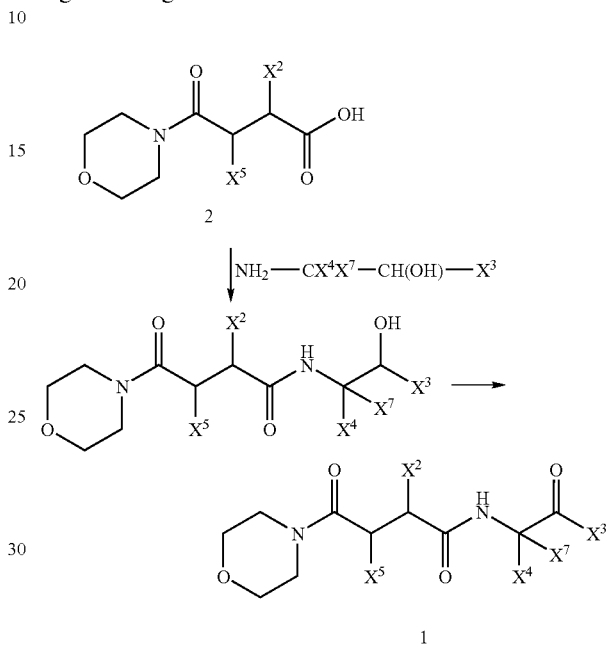

The condensation reaction can be effected with an appropriate coupling agent as above and the oxidation step can be carried out with an oxidizing agent (e.g. Dess-Martin Periodinane or Sodium hypochlorite and TEMPO) in a suitable solvent at ambient temperature. Detailed descriptions for the synthesis of a compound of Formula I by the processes in Reaction Scheme 2 are set forth in the Examples 1, 2 and 10.

Similarly, compounds of Formulae II and III can be synthesized by following the same schemes 1 and 2 with corresponding starting materials, i.e. the corresponding acid and amino compounds.

Compounds of Formula 2 can be prepared by reacting a compound of Formula 3 with a compound of Formula $X^2L$:

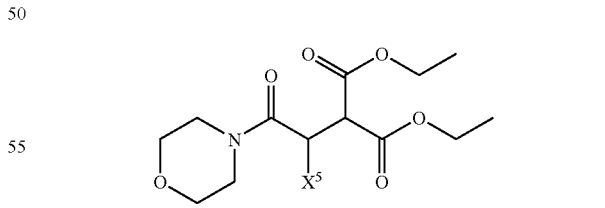

in which L is a leaving group and $X^2$ and $X^5$ are as defined in the Summary of the Invention. The reaction involves alkylation followed by alkaline hydrolysis at a temperature during which the dicarboxylic acid formed undergoes monodecarboxylation. The decarbalkoxylation can be effected under strongly basic conditions (e.g. in the presence of 1N aqueous sodium hydroxide) in a suitable solvent (e.g. ethanol).

Some of the compounds of Formula 2 can be prepared according to the following reaction scheme:

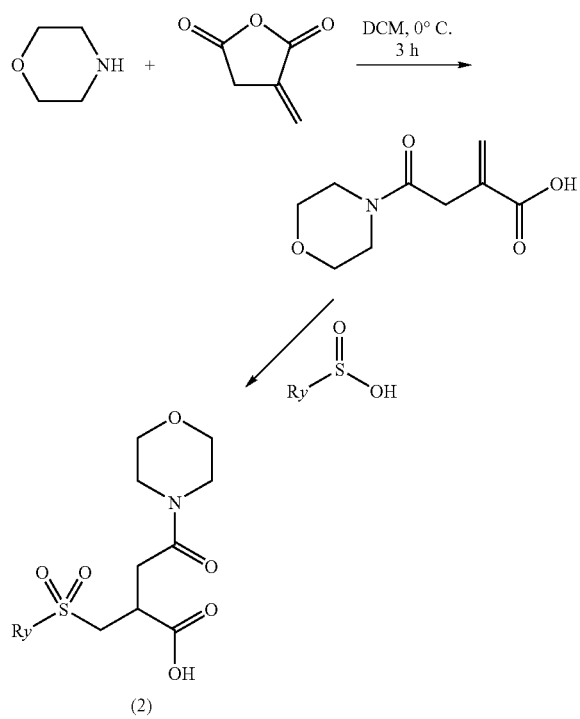

where Ry is, for example, benzyl, iso-butyl, cyclopropylmethyl. Ry is not limited to the examples provided. Other substituents at Ry may also provide satisfactory results, and those sastisfactory substituents are referred to as "equivalent substituents" for the purpose of this application.

If applicable, compounds 2 can be resolved as their individual stereoisomers by chiral HPLC or by reacting a racemic mixture of the compound with an optically active resolving agent to form a pair of diastereoisomeric compounds, separating the diastereomers and recovering the optically pure enantiomer. Diastereomers have distinct physical properties (e.g., melting points, boiling points, solubilities, reactivity, etc.) and can be readily separated by taking advantage of these dissimilarities. The diastereomers can be separated by separation/resolution techniques based upon differences in solubility. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

A compound of Formula I, II or III can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I, II or III can be prepared by reacting the free acid form of the compound with a pharmaceutically acceptable inorganic or organic base. Inorganic and organic acids and bases suitable for the preparation of the pharmaceutically acceptable salts of compounds of Formulae I, II and III are set forth in the definitions section of this Application.

Alternatively, the salt forms of the compounds of Formulae I, II and III can be prepared using salts of the starting materials or intermediates.

The free acid or free base forms of the compounds of Formulae I, II and III can be prepared from the corresponding base addition salt or acid addition salt form. For example, a compound of Formula I, II or III in an acid addition salt form can be converted to the corresponding free base by treating with a suitable base (e.g., ammonium hydroxide solution, sodium hydroxide, and the like). A compound of Formula I, II or III in a base addition salt form can be converted to the corresponding free acid by treating with a suitable acid (e.g., hydrochloric acid, etc).

The N-oxides of compounds of Formulae I, II and III can be prepared by methods known to those of ordinary skill in the art. For example, N-oxides can be prepared by treating an unoxidized form of the compound of Formula I, II or III with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formulae I, II and III can be prepared from the N-oxide of an appropriate starting material.

Compounds of Formulae I, II and III in unoxidized form can be prepared from N-oxides of compounds of Formulae I, II and III by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formulae I, II and III can be prepared by methods known to those of ordinary skill in the art (e.g., for further details see Saulnier et al.(1994), *Bioorganic and Medicinal Chemistry Letters*, Vol. 4, p. 1985). For example, appropriate prodrugs can be prepared by reacting a non-derivatized compound of Formula I, II or III with a suitable carbamylating agent (e.g., 1,1-acyloxyalkylcarbonochloridate, para-nitrophenyl carbonate, or the like).

Protected derivatives of the compounds of Formulae I, II and III can be made by means known to those of ordinary skill in the art. A detailed description of the techniques applicable to the creation of protecting groups and their removal can be found in T. W. Greene, *Protecting Groups in Organic Synthesis*, 3$^{rd}$ edition, John Wiley & Sons, Inc. 1999.

Compounds of the present invention may be conveniently prepared, or formed during the process of practicing the invention, as solvates (e.g. hydrates). Hydrates of compounds of the present invention may be conveniently prepared by recrystallisation from an aqueous/organic solvent mixture, using organic solvents such as dioxane, tetrahydrofuran or methanol.

The present invention is further exemplified, but not limited by, the following examples that illustrate the preparation of the compounds of the present invention (Examples) and their corresponding intermediates (References). These specifically exemplified embodiments are intended to provide guidance to carry out the present invention to a greater extent.

Reference 1

(S)-2-Amino-1-(3-cyclopropyl-1,2,4-oxadiazol-5-yl)-butan-1-ol

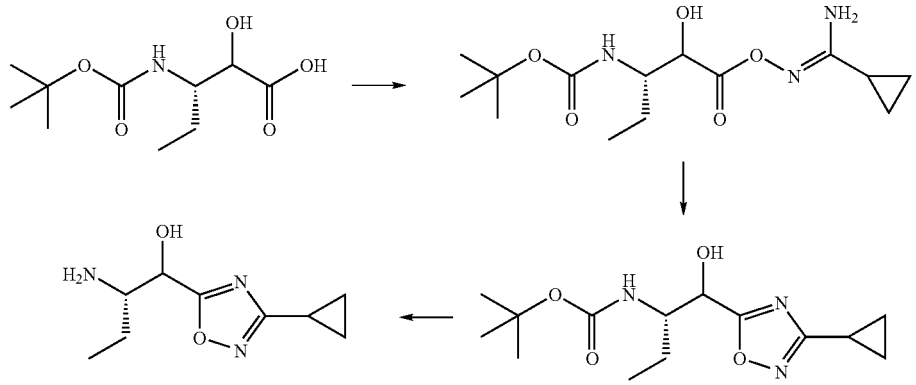

A solution of (S)-3-tert-Butoxycarbonylamino-2-hydroxy-pentanoic acid (2.00 g, 8.57 mmol) and N-Hydroxy-cyclopropanecarboxamidine (1.03 g, 10.29 mmol) in dichloromethane (20 mL) was stirred at 0° C. and 1.25 equivalents of N-cyclohexylcarbodiimide-N'-methyl polystyrene (1.70 mmol/g, 6.30 g, 10.72 mmol) was added in portions. The reaction mixture stirred under nitrogen for three hours while warming to 15° C. The reaction mixture was filtered, the resin washed with dichloromethane and the filtrate evaporated under vacuum to dryness. [LC/MS m/z=338 (M+H+Na)] The residue was dissolved in tetrahydrofuran (20 mL) and heated in a microwave reactor (Smith Creator) at 160° C. for three minutes, cooled to room temperature and evaporated under vacuum to dryness. [LC/MS m/z=320 (M+H+Na)]. The residue was dissolved in dichloromethane (50 mL) and stirred at room temperature as a 50 mL solution of 50% trifluoroacetic acid in dichloromethane was added dropwise. After three hours the reaction was evaporated under vacuum to dryness and dissolved in 50 mL of dichloromethane again. Three equivalents of Silicycle triamine-3 was added and the mixture stirred at room temperature overnight. The mixture was filtered and washed with dichloromethane. Evaporate under vacuum to give 1.04 g (61% overall). [LC/MS m/z=198 (M+H)]

Reference 2

(S)-2-Amino-1-(3-phenyl-1,2,4-oxadiazol-5-yl)-butan-1-ol

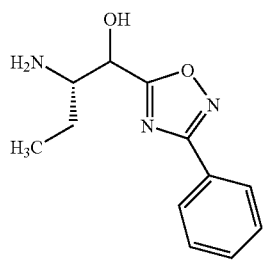

A solution of (S)-3-tert-Butoxycarbonylamino-2-hydroxy-pentanoic acid (2.00 g, 8.57 mmol) and N-hydroxy-benzamidine (1.3 g, 9.5 mmol) in dichloromethane (40 mL) was stirred at 0° C. N-cyclohexylcarbodiimide-N'-methyl polystyrene (1.90 mmol/g, 6 g, 11.4 mmol) was added in portions. The reaction mixture was stirred under nitrogen for one hour. The reaction mixture was filtered, the resin washed with dichloromethane and the filtrate evaporated under vacuum to dryness. [LC/MS m/z=352 (M+H+), 296(M+H+-isobutene)]. The residue was dissolved in tetrahydrofuran (20 mL) and heated in a microwave reactor (Smith Creator) at 180° C. for three minutes, cooled to room temperature and evaporated under vacuum to dryness. The crude product was purified via flash chromatography (eluted with a gradient from 5% to 65% ethyl acetate in heptane) to give the product as a white solid [LC/MS m/z=356 (M+Na+), 234 (M+H+-Boc)].

It was dissolved in dichloromethane (45 mL) and trifluoroacetic acid (5 mL) was added. After two hours the reaction was evaporated under vacuum to dryness. The residue was redissolved in 50 mL of dichloromethane. Silicycle triamine-3 (9.9 g, 39 mmol) was added and the mixture stirred at room temperature overnight. The mixture was filtered and washed with dichloromethane. The Filtrate was concentrated under vacuum to give 775 mg (38% overall) product as a white solid. [LC/MS m/z=234 (M+H)]

¹HNMR (CDCl₃) 8.12–8.06 (m, 2H), 7.54–7.45 (m, 3H), 4.93 & 4.75 (2xd, J=5 Hz & 3.5 Hz, 1H), 3.25 & 3.11 (2xm, 1H), 1.78–1.42 (2xm, 2H), 1.04 & 1.01 (2x t, J=7.5 Hz, 3H).

Reference 3

(S)-2-Amino-1-(5-phenyl-[1,2,4]oxadiazol-3-yl)-butan-1-ol

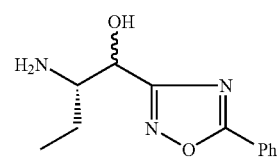

Reference 3 was synthesized as described in the following reaction protocol:

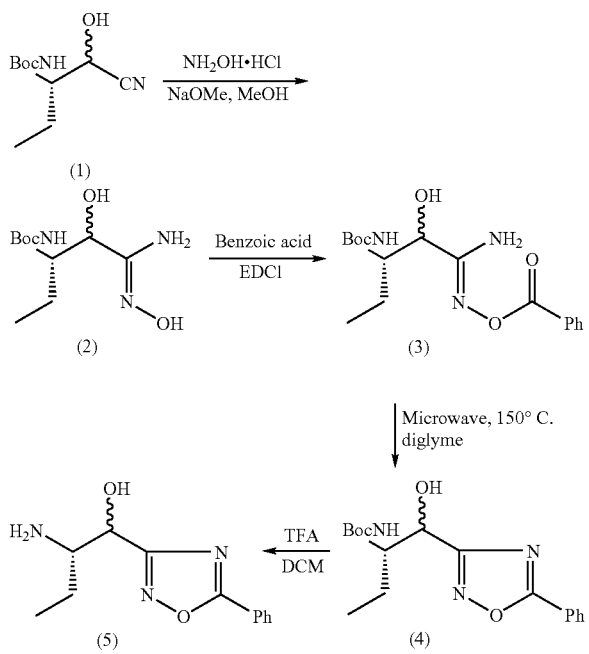

{(S)-1-[Hydroxy-(N-hydroxycarbamimidoyl)-methyl]-propyl}-carbamic acid tert-butyl ester (2)

A solution of (2-cyano-1-ethyl-2-hydroxy-ethyl)-carbamic acid tert-butyl ester (9.53 g, 44 mmol) in methanol (80 ml) was cooled to 0° C. and treated successively with hydroxylamine hydrochloride (3.05, 44 mmol) in methanol (80 ml) and 25% sodium methoxide solution in methanol (10.2 ml). Stirred at 0° C. for 5 minutes, cold bath removed and the reaction mixture stirred at room temperature for 5 hours. Methanol evaporated off under reduced pressure, crude partitioned between ethyl acetate and water. Organic layer separated, dried (MgSO$_4$) and evaporated under reduced pressure to give yellow oil. Purified by mplc, eluting with a mixture of ethyl acetate-heptane to give the title compound as white solid (3.5 g); MS: M(H$^+$) 248.

{1-[Hydroxy-(N-benzoyloxycarbamimidoyl)-methyl]-propyl}-carbamic acid tert-butyl ester (3)

A solution of {1-[hydroxy-(N-hydroxycarbamimidoyl)-methyl]-propyl}-carbamic acid tert-butyl ester (2) (2.5 g, 10 mmol) in dichloromethane (125 ml) was treated with benzoic acid (1.36 g, 11 mmol), EDCI (2.14 g, 11 mmol), HOBT (1.37 g, 10 mmol) and triethylamine (1.35 ml, 11 mmol) and stirred at room temperature overnight. Reaction mixture was washed with saturated sodium bicarbonate solution and then water and dried over Na$_2$SO$_4$. Solvent evaporated under reduced pressure, crude purified by mplc eluting with 1% triethylamine in 2:3 v/v ethyl acetate and heptane mixture to give yellow solid (850 mg); MS: MH$^+$ 352.

2-Amino-1-(5-phenyl-[1,2,4]oxadiazol-3-yl)-butan-1-ol (5)

A solution of (3) (1.5 g, 4.3 mmol) in diglyme was heated at 150° C. in a microwave reactor (Smith Creator, S00219) for 40 minutes. Solvent evaporated under vacuum in Genevac Evaporator at 80° C. for 3hours to give a brown solid. This was taken in dichloromethane (40 ml) and treated with trifluoroacetic acid at room temperature for 2 hours. Solvent evaporated to dryness under reduced pressure, crude taken in water, washed with DCM, aqueous layer basified with 1M NaOH solution and extracted with dichloromethane. Organic layer dried over Na$_2$SO$_4$ and evaporated under reduced pressure to give pale brown solid (300 mg); $^1$HNMR (CDCl$_3$) 8.14–8.10 (m, 2H), 7.59–7.47 (m, 3H), 4.83 & 4.65 (d, J=5 Hz, 1H), 3.18–3.05 (2m, 1H), 2H), 1.05–0.97 (2Xt, J=7.2 Hz, 3H).

Reference 4

(S)-2-Amino-1-(5-trifluoromethyl-1,2,4-oxadiazol-3-yl)-butan-1-ol; compound with trifluoro-acetic acid

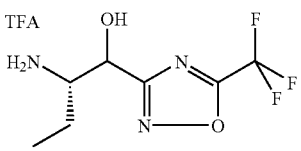

A solution of {(S)-1-[Hydroxy-(N-hydroxycarbamimidoyl)-methyl]-propyl}-carbamic acid tert-butyl ester (452 mg, 1.83 mmol) in dioxane (5 mL) was treated with trifluoroacetic anhydride (0.349 ml, 2.47 mmol) and heated at 100° C. in a microwave reactor (Smith Creator, S00219) for 7 minutes. Solvent evaporated under reduced pressure and the crude was purified by flash chromatography eluting with a mixture of ethyl acetate and heptane to give {(S)-1-[Hydroxy-(5-trifluoromethyl-1,2,4-oxadiazol-3-yl)-methyl]-propyl}-carbamic acid tert-butyl ester as a brown solid (476 mg) (mixture of diastereoisomers).

$^1$H NMR (CDCl$_3$): 5.00 (d, J=4 Hz, 1H), 4.82, 4.65 (bd, J=7 Hz, 1H), 4.00, 3.85 (broad m, 1H), 1.78–1.52 (m, 1H), 1.52–1.32 (m, 1H), 1.44, 1.37 (2xs, 9H), 1.02 (2xt, J=7 Hz & 4 Hz, 3H).

MS: 348 (M+Na)

A solution of {(S)-1-[Hydroxy-(5-trifluoromethyl-1,2,4-oxadiazol-3-yl)-methyl]-propyl)}-carbamic acid tert-butyl ester (3.6 g, 0.011 mol) in methylene chloride (15 mL) was treated with trifluoroacetic acid (8.53 ml, 0.111 mol) and stirred at room temperature for 3 h. Solvent evaporated under reduced pressure to give (S)-2-amino-1-(5-trifluoromethyl-1,2,4-oxadiazol-3-yl)-butan-1-ol; compound with trifluoro-acetic acid as a brown oil (4.42 g) (mixture of diastereoisomers).

$^1$H NMR (CDCl$_3$): 8.22 (bs, 2H), 7.04 (bs, 1H), 5.14, 4.90 (d, J=4 Hz & 7 Hz, 1H) 3.40–3.28 (m, 1H), 1.64–1.37 (m, 2H), 0.80 (2xt, J=7 Hz, 3H).

MS: 226 (MH$^+$)

Reference 5

(S)-2-Amino-1-(5-ethyl-1,2,4-oxadiazol-3-yl)-butan-1-ol; compound with trifluoro-acetic acid

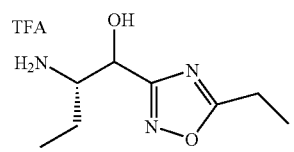

A solution of {(S)-1-[Hydroxy-(N-hydroxycarbamimidoyl)-methyl]-propyl}-carbamic acid tert-butyl ester (525 mg, 2.13 mmol) in dioxane (5 mL) was treated with propionic anhydride (0.300 ml, 2.34 mmol) and heated at 150° C. in a microwave reactor (Smith Creator, S00219) for 35 minutes. Solvent evaporated under reduced pressure and the crude was purified by flash chromatography eluting with a mixture of ethyl acetate and heptane to give {(S)-1-[(5-Ethyl-1,2,4-oxadiazol-3-yl)-hydroxy-methyl]-propyl}-carbamic acid tert-butyl ester as a yellow solid (406 mg) (mixture of diastereoisomers).

$^1$H NMR (CDCl$_3$): 4.98–4.72 (m, 2H), 4.00, 3.88 (m, 1H), 3.64, 3.45 (bs, 1H), 2.89 (2xq, J=7.6 Hz, 2H), 1.69 (m, 1H), 1.47 (m, 1H), 1.45, 1.39 (2xs, 9H), 1.44–1.36 (m, 3H), 0.98 (2xt, J=9 Hz & 7 Hz, 3H).

MS: 308 (M+Na)

A solution of {(S)-1-[(5-Ethyl-1,2,4-oxadiazol-3-yl)-hydroxy-methyl]-propyl}-carbamic acid tert-butyl ester (214 mg, 0.751 mmol) in methylene chloride (5 mL) was treated with trifluoroacetic acid (0.578 ml, 7.504 mmol) and stirred at room temperature for 3 h. Solvent evaporated under reduced pressure to give (S)-2-Amino-1-(5-ethyl-1,2,4-oxadiazol-3-yl)-butan-1-ol; compound with trifluoro-acetic acid as a brown oil (224 mg) (mixture of diastereoisomers).

MS: 186 (MH$^+$)

$^1$H NMR (CDCl$_3$): 8.10–7.33 (2xbs, 3H), 5.24, 5.07 (d, J=3.5 Hz & 5.5 Hz, 1H), 3.77, 3.62 (bs, 1H), 2.91 (2xq, J=7 Hz, 2H), 1.78 (m, 1H), 1.76–1.40 (m, 1H), 1.39 (2xt, J=7 Hz, 3H), 1.02 (2xt, J=7.5 Hz, 3H).

Reference examples 6, 7, 8 were prepared according to the scheme below

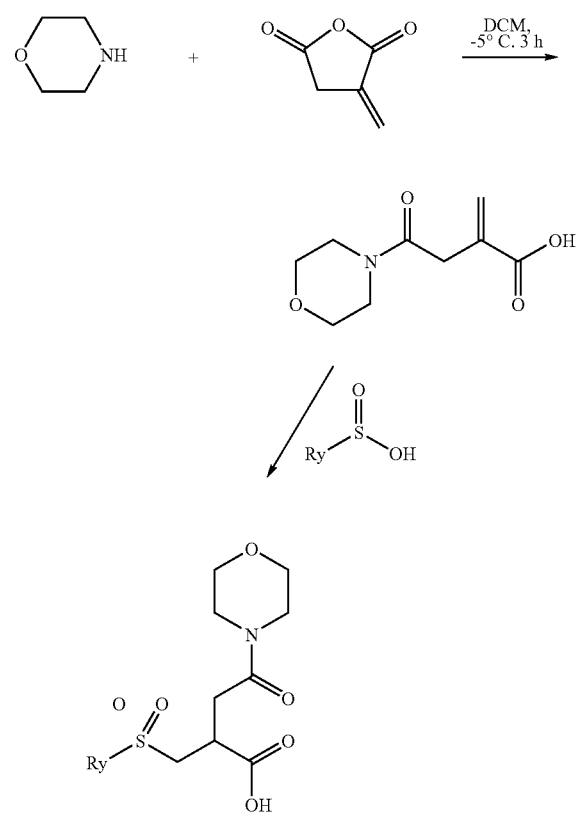

Ry = Benzyl, iso-butyl, cyclopropylmethyl

Reference 6

4-Morpholin-4-yl-4-oxo-2-phenylmethanesulfonylmethyl-butyric acid

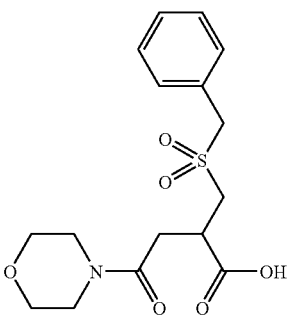

Morpholine (23.6 g, 271 mmol) was slowly added to a stirred solution of itaconic anhydride (30.36 g, 271 mmol) suspended in dichloromethane (200 mL) below −5° C. and stirred at that temperature for 1 hr. The reaction mixture was allowed to slowly warm up to room temperature and evaporated under reduced pressure below 30° C. to give a viscous oil. This was triturated with ethyl acetate to give 2-Methylene-4-morpholin-4-yl-4-oxo-butyric acid as white solid (36.8 g, 68%). The product was used without further purification in the next step.

A mixture of 2-Methylene-4-morpholin-4-yl-4-oxo-butyric acid (12.74 g, 64 mmol) and benzyl sulphinic acid (10.0 g, 64 mmol) was suspended in anhydrous toluene (270 mL) and anhydrous acetonitrile (55 mL). This mixture was warmed to 85° C. and stirred vigorously for 3 h (during this period the external bath temperature climbes to 95° C.). The reaction mixture was allowed to cool to room temperature then concentrated under vacuum. The solid residue was triturated with methanol (approximately 35 mL) and filtered. The solid was washed with 2×15 mL of methanol then washed with ether to give 9.9 g of product. The mother liquor was concentrated then taken up in 30 mL of methanol. This solution was allowed to stand at −20° C. overnight. The resulting precipitate was filtered, washed with methanol and ether to give 2.1 g of product. The combined product (9.9+2.1=12.0 g) was 86% pure by HPLC (UV analysis 254 nM). This material was taken up in 400 mL of 20% methanol in CH$_2$Cl$_2$. The cloudy solution was filtered and concentrated under vacuum. The residue was triturated with about 50 mL of methanol, filtered and the solid washed with ether then dried under vacuum to give 10.7 g of product as a white solid, 96% pure by HPLC analysis. $^1$H NMR (DMSO): δ 12.63 (bs), 7.40 (m, 5H), 4.55 (dd, AB pattern, J=14 Hz, 2H), 3.53 (m, 4H), 3.40–3.2 (m, 7H), 2.78 (d, 2H), LC (C$_{18}$ Dynamax column; CH$_3$CN/H$_2$O/0.1% TFA; 20–100 CH$_3$CN over 20 min; rt= 7.59 min).

Chiral separation of the enantiomers on a Chiralpak AD column using 80% ethanol/20% heptane/0.01% TFA gave (R)-4-Morpholin-4-yl-4-oxo-2-phenylmethanesulfonylmethyl-butyric acid (6a) and (S)-4-Morpholin-4-yl-4-oxo-2-phenylmethanesulfonylmethyl-butyric acid (6b).

Reference 7

2-(2-Methyl-propane-1-sulfonylmethyl)-4-morpholin-4-yl-4-oxo-butyric acid

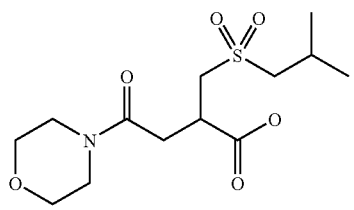

A mixture of 2-Methylene-4-morpholin-4-yl-4-oxo-butyric acid (3.98 g, 20 mmol) and isobutyl-sulphinic acid (2.44 g, 20 mmol) were suspended in anhydrous toluene (80 mL) and anhydrous acetonitrile (20 mL). This mixture was warmed to 85° C. and stirred vigorously for 4.5 h. The reaction mixture was allowed to cool to room temperature and concentrated under vacuum. The residue was purified by flash chromatography using a 90 g silica gel column eluting with 10% methanol/$CH_2Cl_2$. Recovered 3.7 g of product as an oil. Triturated residue with isopropanol (5 mL)/ether (100 mL). Product began to precipitate out. Cooled this to 5° C. for 17 hrs(overnight). Product was collected by filtration, washed with ether and dried under vacuum to give 2-(2-Methyl-propane-1-sulfonylmethyl)-4-morpholin-4-yl-4-oxo-butyric acid as a white solid (1.8 g).

$^1$H NMR (DMSO): δ 12.59 (bs, 1H), 3.56–3.52 (m, 5H), 3.43–3.40 (m, 4H), 3.3–3.1 (m, 2H), 3.08 (d, 2H), 2.79 (m, 2H), 2.20 (m, 1H), 1.06 (d, 6H). MS: m/z 320 (M−H)$^-$.

Chiral separation of the enantiomers on a Chiralpak AD column using 70% ethanol/70% heptane/0.01% TFA gave (R)-2-(2-Methyl-propane-1-sulfonylmethyl)-4-morpholin-4-yl-4-oxo-butyric acid (7a) and (S)-2-(2-Methyl-propane-1-sulfonylmethyl)- 4-morpholin-4-yl-4-oxo-butyric acid (7b)

Reference 8

2-Cyclopropylmethanesulfonylmethyl-4-morpholin-4-yl-4-oxo-butyric acid

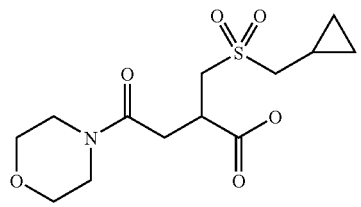

To a solution of cyclopropylmethylsulphinic acid (1.8 g, 15 mmol) in anhydrous toluene (45 mL) and anhydrous acetonitrile (9 mL) was added 2-Methylene4-morpholin-4-yl-4-oxo-butyric acid (2.98 g, 15 mmol). The resulting solution was warmed to 85° C. and stirred at this temperature for 4.5 h. The heterogeneous reaction mixture is then allowed to cool to room temperature then concentrated under reduced pressure. The residue is then purified by flash chromatography eluting with 7% methanol in dichloromethane to give 2-Cyclopropylmethanesulfonylmethyl-4-morpholin-4-yl-4-oxo-butyric acid (1.92 g) as viscous oil which was re crystallized from hot ethyl acetate to give a white solid.

$^1$H NMR (CDCl$_3$): δ 8.23 (bs, 1H), 3.80–3.55 (m, 8H), 3.55–3.40 (m, 2H), 3.4–3.2 (m, 1H), 3.2–2.84 (m, 2H), 2.95 (d, 2H), 1.28–1.15 (m, 1H), 0.84–0.64 (m, 2H), 0.45–0.35 (m, 2H).

MS: 320 (MH$^+$), 342 (M+Na).

Combustion Analysis: Calculated: C; 48.9, H; 6.6, N; 4.4. Found: C; 48.9, H; 6.8, N; 4.3.

Chiral separation of the enantiomers on a Chiralpak AD column using 70% ethanol/70% heptane/0.01% TFA gave (R)-2-Cyclopropylmethanesulfonylmethyl-4-morpholin-4-yl-4-oxo-butyric acid (8a) and (S)-2-Cyclopropylmethanesulfonylmethyl-4-morpholin-4-yl-4-oxo-butyric acid (8b)

Reference examples (9)–(14) were made according to the scheme below.

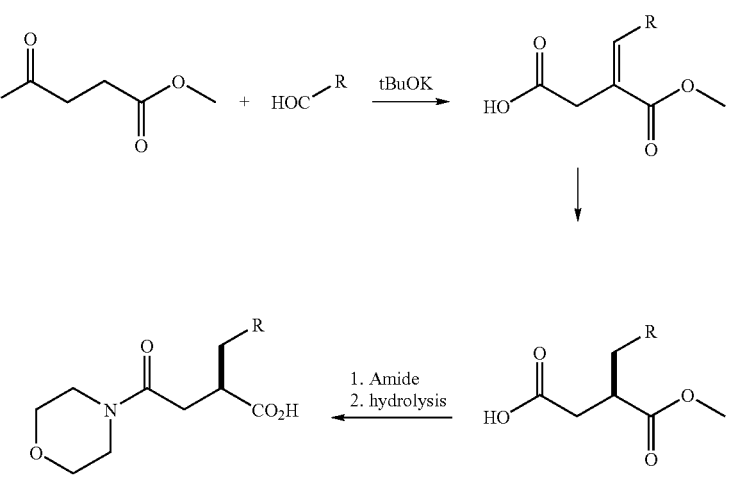

References:
Angew. Chem. Int. Ed. 1998, 37(13/14), 1931–1933.
Angew. Chem. Int. Ed. 2000, 39(11), 1981–1984 (Amido-derivatives).

Reference 9

(R)-2-(1-Benzyl-cyclopropylmethyl)-4-morpholin-4-yl-4-oxo-butyric acid

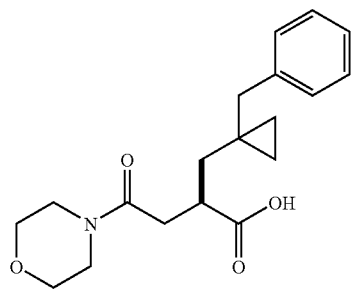

To a warmed solution (75° C.) of tBuOK 1M in tBuOH (1.3 eq., 16.0 mmol, 16.0 mL) under N2 was added slowly a mixture of dimethyl succinate (2.42 g, 14.7 mmol, 1.2 eq) and 1-Benzyl-cyclopropanecarbaldehyde (1.97 g, 12.3 mmol). After the addition, the mixture was heated to 85° C. for another 5 hr, cooled and concentrated in vacuum. The residue was diluted with water (150 mL), and extracted with ether (50 mL). The aqueous layer was acidified to pH 1 and extracted with ether (2×75 mL). The acidic extracts were dried (MgSO4) and concentrated in vacuum. The residue was purified over 90 g silica gel, eluted with ethyl acetate and heptane (1:1 then 2:1) to afford 2-[1-(1-Benzyl-cyclopropyl-meth-(Z)-ylidene]-succinic acid 1-methyl ester as a light yellow oil (3.096 g, 91.8% yield).

$^1$H NMR (CDCl$_3$) 7.2 (m, 5H), 7.0 (s, 1H), 3.75 (s, 3H), 3.2 (s, 2H), 2.75 (s, 2H), 0.85 (m, 2H), 0.75 (m, 2H).

A solution of 2-[1-(1-Benzyl-cyclopropyl)-meth-(Z)-ylidene]-succinic acid 1-methyl ester (2.686 g, 9.79 mmol) and sodium methoxide (0.1 eq., 0.98 mmol, 52.9 mg) in dry methanol (25 mL) was degassed with N2 for 5 min then (+)-(2S,5S)-2,5-Diethylphospholanobenzene (cyclooctadiene) Rhodium tetrafluoroborate (25 mg) was added. The mixture was hydrogenated at 60 psi for 24 hr, then concentrated in vacuum. The residue was diluted with NaHCO$_3$ (150 mL) and the solution was made basic with NaOH and extracted with ether (80 mL). The aqueous layer was acidified to pH 1 and extracted with ether (2×100 mL). The acidic extracts were dried (MgSO4) and concentrated in vacuum to afford (R)-2-(1-Benzyl-cyclopropylmethyl)-succinic acid 1-methyl ester as a yellow oil (2.465 g, 91% yield).

$^1$H NMR (CDCl$_3$) 7.3 m (5H), 3.75 (s, 3H), 3.15 (m, 1H), 2.9 (d, J=14.3 Hz, 1H), 2.75 (dd, J=17.2, 9.8 Hz, 1H), 2.5 (d, J=14.3 Hz, 1H), 1.58 (dd, J=14.1, 6.5 Hz, 1H), 1.42, 9.3 Hz, 1H), 0.6 (m, 1H), 0.4 (m, 3H).

To a solution of (R)-2-(1-Benzyl-cyclopropylmethyl)-succinic acid 1-methyl ester (2.453 g, 8.88 mmol), di-isopropyl amine (1.1 eq, 9.76 mmol, 1.26 g) and morpholine (1.5 eq., 13.3 mmol, 1.16 g) in dry dichloromethane under N$_2$ was added PyBOP (1.1 eq., 9.76 mmol, 5.08 g). The mixture was stirred at room temperature for 5 hr, and concentrated in vacuum. The residue was dissolved in ethyl acetate (150 mL) and washed with water (100 mL), NH$_4$Cl (100 mL), NaHCO$_3$ (2×100 mL), then water (100 mL). The organic layer was dried (MgSO$_4$) and concentrated in vacuum. The residue was purified over 120 g silica gel, eluted with ethyl acetate:heptane (1:1.5, 1:1, to 2:1) to afford the desired compound contaminated with PyBOP residues. A solution of the mixture in ether containing ethyl acetate (250 mL total) was washed with dilute HCl (150 mL), water (150 mL) dilute NaOH (150 mL) then water (150 mL). The organic layer was dried (MgSO4) and concentrated in vacuum to afford (R)-2-(1-Benzyl-cyclopropylmethyl)-4-morpholin-4-yl-4-oxo-butyric acid methyl ester as a white solid (2.292 g, 74.7% yield).

$^1$H NMR (CDCl$_3$) 7.3 (m, 5H), 3.8 (s, 3H), 3.6 (m, 6H), 3.4 (m, 2H), 3.2 (m, 1H), 3.0 (d, J=14.4 Hz, 1H), 2.7 (dd, J=16.1, 10.3 Hz, 1H), 2.5 (d, J=14.5 Hz, 1H), 2.3 (dd, J=16.2, 3.9 Hz, 1H), 1.6 (dd, J=14, 5.9 Hz, 1H), 1.27 (dd, J=14, 10 Hz, 1H), 0.55 (m, 1H), 0.4 (m, 3H).

To a solution of (R)-2-(1-Benzyl-cyclopropylmethyl)-4-moipholin-4-yl-4-oxo-butyric acid methyl ester (2.29 g, 6.63 mmol) in MeOH:H2O (2:1 vol, 21 mL) was added THF (5 mL) followed by lithium hydroxide monohydrate (3.0 eq., 19.9 mmol, 834.5 mg). The mixture was stirred at rt for 19 hr, then concentrated in vacuum. The residue was diluted with water (100 mL) and extracted with ether (60 mL). The aqueous layer was acidified to pH 1 and extracted with ethyl acetate (2×70 mL). The acidic extracts were dried (MgSO4) and concentrated in vacuum to afford (R)-2-(1-Benzyl-cyclopropylmethyl)-4-morpholin-4-yl-4-oxo-butyric acid as colorless oil (2.128 g, 96.8% yield).

$^1$H NMR (CDCl$_3$) 7.25 (m, 5H), 3.65 (m, 6H), 3.45 (m, 2H), 3.2 (m, 1H), 2.9 (d, J=14.4 Hz, 1H), 2.78 (dd, J=16.3, 10.0 Hz, 1H), 2.55 (d, J=14.5 Hz, 1H), 2.48 (dd, J=16.5, 4.0 Hz, 1H), 1.6 (m, 2H), 0.5 (m, 4H).

Reference 10

(R)-4,4-Dimethyl-2-(2-morpholin-4-yl-2-oxo-ethyl)-pentanoic acid

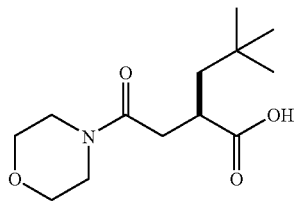

Similarly prepared according to the general procedure for Reference 9 but using dimethyl succinate and 2,2-Dimethyl-propionaldehyde as the aldehyde component.

$^1$H NMR (CDCl$_3$) 3.7 (m, 6H), 3.5 (m, 2H), 3.0 (m, 1H), 2.7 (dd, J=16.2, 9.0 Hz, 1H), 2.5 (dd, J=16.3, 4.5 Hz, 1H), 1.9 (dd, J=14.1, 7.4 Hz, 1H), 1.3 (dd, J=14.1, 4.2 Hz, 1H), 1.0 (s, 9H).

Reference 11

(R)-4,4-Dimethyl-2-(2-morpholin-4-yl-2-oxo-ethyl)-5-phenyl-pentanoic acid

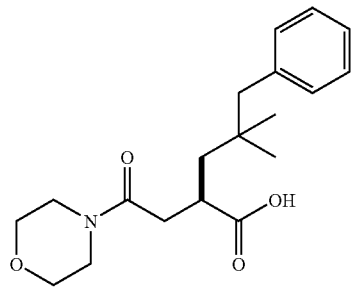

Similarly prepared according to the general procedure for Reference 9 but using dimethyl succinate and 2,2-Dimethyl-3-phenyl-propionaldehyde as the aldehyde component.

$^1$H NMR (CDCl$_3$) 7.3 (m, 3H), 7.15 (m, 2H), 3.7 (m, 6H), 3.5 (m, 2H), 3.0 (m, 1H), 2.8 (dd, J=16.4, 9.2 Hz, 1H), 2.6 (s, 2H), 2.5 (dd, J=16.5, 4.4 Hz, 1H), 2.0 (dd, J=14.3, 7.5 Hz, 1H), 1.3 (dd, J=14.3, 3.9 Hz, 1H), 0.95 (s, 3H), 0.93 (s, 3H).

Reference 12

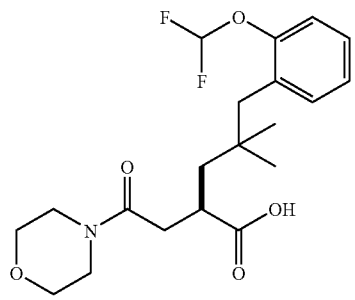

(R)-5-(2-Difluoromethoxy-phenyl)-4,4-dimethyl-2-(2-morpholin-4-yl-2-oxo-ethyl)-pentanoic acid Similarly prepared according to the general procedure for Reference 9 but using dimethyl succinate and 3-(2-Difluoromethoxy-phenyl)-2,2-dimethyl-propionaldehyde as the aldehyde component.

$^1$H NMR (CDCl$_3$) 7.2 (m, 4H), 6.5 (t, J=74 Hz, 1H), 3.65 (m, 6H), 345 (m, 2H), 3.1 (m, 1H), 2.77 (dd, J=16.4, 9.2 Hz, 1H), 2.7 (d, J=13 Hz, 1H), 2.6 (d, J=13 Hz, 1H), 2.5 (dd, J=16.4, 4.4 Hz, 1H), 2.0 (dd, J=14.1, 7.6 Hz, 1H), 1.38 (dd, J=14.2, 3.7 Hz, 1H), 0.95 (s, 6H).

Reference 13

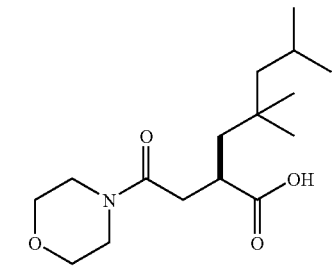

(R)-4,4,6-Trimethyl-2-(2-morpholin-4-yl-2-oxo-ethyl)-heptanoic acid Similarly prepared according to the general procedure for Reference 9 but using dimethyl succinate and 2,2,4-Trimethyl-pentanal as the aldehyde component.

$^1$H NMR (CDCl$_3$) 3.7 (m, 6H), 3.5 (m, 2H), 2.9 (m, 1H), 2.75 (dd, J=16.3, 9.6 Hz, 1H), 2.45 (dd, J=16.2, 4.0 Hz, 1H), 2.8–1.0 (m, 8H), 0.9 (m, 8H).

Reference 14

(S)-2-(5-Methyl-thiophen-2-ylmethyl)-4-morpholin-4-yl-4-oxo-butyric acid

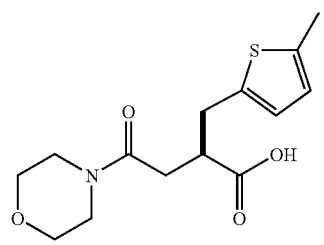

Similarly prepared according to the general procedure for Reference 9 but using dimethyl succinate and 5-Methyl-thiophene-2-carbaldehyde as the aldehyde component.

$^1$H NMR (CDCl$_3$) 6.6 (m, 2H), 3.7 (m, 6H), 3.4 (m, 2H), 3.3 (dd, J=14.2, 5.0 Hz, 1H), 3.2 (m, 1H), 3.02 (dd, J=14.3, 8.7 Hz, 1H), 2.68 (dd, J=16.6, 8.5 Hz, 1H), 2.58 (dd, J=16.5, 4.1 Hz, 1H), 2.45 (d, J=0.6 Hz, 3H).

Reference 15

2-Amino-1-oxazolo[4,5-b]pyridin-2-yl-butan-1-ol

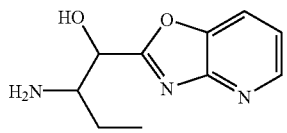

A mixture of 2-amino-3-hydroxy pyridine (25 g, 227 mmol), triethylorthoformate (75 ml) and p-toluenesulfonic acid (61 mg) was heated at 140° C. for 8 hours. Excess triethylorthoformate was removed under vacuum. The product was crystallized from ethyl acetate to yield 22.5 g of oxazolo[4,5-b]pyridine; H$^1$NMR (DMSO-δ): 9.26 (1H, s), 8.78 (1H, d), 8.45 (1H, d), 7.7(1H, dd); MS: 120.8 (M+1).

Oxazolo[4,5-b]pyridine (600 mg, 5 mmol) in 30 ml THF was cooled to 0° C. before the addition of isopropanyl magnesium chloride (2M in THF, 2.5 ml, 5 mmol). After stirring for 1 hour at 0° C., (S)-(1-formyl-propyl)-carbamic acid tert-butyl ester (573 mg, 3 mmol) in 20 ml THP was added. The ice bath was removed and the reaction allowed to warm to room temperature. The reaction mixture was stirred for 2 hours and quenched with saturated ammonium chloride solution. Excess THF was removed and the residue was extracted with EtOAc, washed with brine, dried with anhydrous MgSO$_4$, filtered and concentrated. The crude residue was purified by chromatography to yield 383 mg product; H1 NMR (DMSO-δ): 8.42(1H, m), 8.18(1H, m), 7.3(1H, m), 6.8, 6.6(1H, dd, d, OH, diastereomeric), 6.3, 6.02(1H, d, d, NH, diastereomeric), 4.82, 4.5(1H, m, m, diastereomeric), 1.8–1.3(2H, m), 1.2, 1.05(9H, s,s, diastereomeric), 0.89(3H, m); MS: 306.2(M−1), 308.6(M+1).

Alternative procedure: To a stirred solution of the oxazolo [4,5-b]pyridine (12 g, 100 mmol) in THF (300 ml) was added n-BuLi (1.6M solution in 62.5 ml of hexane) drop wise under $N_2$ at −78° C. After 1 hour, $MgBr.Et_2O$ (25.8 g, 100 mmol) was added and the reaction mixture was allowed to warm to −45° C. for 1 hour before being treated with (S)-(1-formyl-propyl)-carbamic acid tert-butyl ester (11.46 g, 60 mmol) in THF (50 ml). The reaction mixture was stirred for 1 hour, quenched with saturated $NH_4Cl$, and extracted with ethyl acetate. The organic layer was washed with brine, dried with $MgSO_4$ and concentrated. The residue was purified by silica gel column chromatography to yield (S)-[1-(hydroxy-oxazolo[4,5-b]pyridin-2-yl-methyl)-propyl]-carbamic acid tert-butyl ester (14.1 g).

(S)-[1-(Hydroxy-oxazolo[4,5-b]pyridin-2-yl-methyl)-propyl]-carbamic acid tert-butyl ester (311 mg, 1 mmol) and $MeCl_2$ (5 ml) were mixed and TFA (1 ml) was added at room temperature. After stirring for 1 hour, the solvent and excess TFA were removed under vacuum to produce 355 mg of 2-Amino-1-oxazolo[4,5-b]pyridin-2-yl-butan-1-ol TFA salt.

Reference 16

3-Benzylsulfonyl-2-(tetrahydro-pyran-4-yloxymethyl)-propionic acid

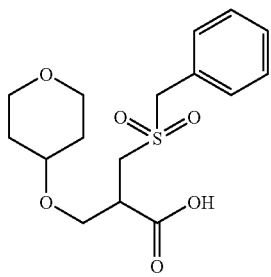

2-(Tetrahydro-pyran-4-yloxymethyl)-acrylic acid ethyl ester (1)

NaH added to a solution of 4-hydroxy tetrahydropyran (5 g, 49 mmol) in THF (40 ml) stirred at room temperature for 30 minutes. A solution of ethyl 2-(bromomethyl) acrylate (9.6 g, 49 mmol) in THF (30 ml) was added and stirred at room temperature overnight. Reaction mixture cooled in ice, quenched with saturated $NH_4Cl$ solution and extracted with ethyl acetate. Organic extracts dried, ($Na_2SO_4$) and purified by mplc eluting with 1:9 to 2:8 v/v ethyl acetate-heptane mixture to give the title compound as yellow oil (6.56 g, 61%). MS: $MH^+$ 215; LCMS retention time 3.29 minutes.

3-Benzylsulfanyl-2-(tetrahydro-pyran-4-yloxymethyl)-propionic acid ethyl ester (2a)

A suspension of 2-(tetrahydro-pyran-4-yloxymethyl)-acrylic acid ethyl ester (2.2 g, 10.2 mmol) in ethanol (100 ml) was treated with a solution of $NaHCO_3$ (0.86 g, 10.2 mmol) in water ml (10 ml) and benzyl mercaptan (1.21 ml, 10.2 mmol) at room temperature overnight. Ethanol evaporated off under reduced pressure, crude partitioned between ethyl acetate and water, organic layer separated and purified by mplc eluting with 1:9 to 2:8 v/v ethyl acetate-heptane mixture to give the title compound as pale yellow oil (1.27 g). MS: 339 ($MH^+$); LCMS (Protocol B) retention time 4.3 minutes.

3-Benzylsulfanyl-2-(tetrahydro-pyran-4-yloxymethyl)-propionic acid (3a)

A solution of 3-benzylsulfanyl-2-(tetrahydro-pyran-4-yloxymethyl)-propionic acid ethyl ester (1.27 g) in ethanol (30 ml) was treated with 2N NaOH (9.4 ml) overnight. Usual water work up gave the title compound as white solid; MS: 333 (M+Na), 311 (M+1); LCMS retention time 3.7 minutes.

3-Benzylsulfonyl-2-(tetrahydro-pyran-4-yloxymethyl)-propionic acid (Reference 15)

A solution of 3-Benzylsulfanyl-2-(tetrahydro-pyran-4-yloxymethyl)-propionic acid (1.16 g, 3.7 mmol) in a mixture

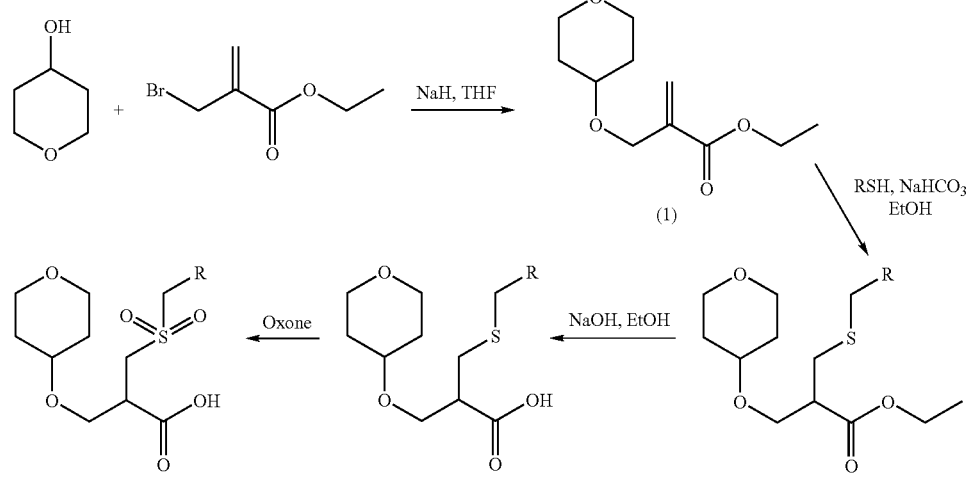

(27a) R = Ph
(27b) R = Me (3a) R = Ph
(3b) R = Me (2a) R = Ph
(2b) R = Me of MeOH (10 ml) and water (30 ml) was treated oxone (3.5 g, 5.6 mmol) overnight. Methanol evaporated off under reduced pressure, aqueous layer extracted with ethyl acetate, dried ($Na_2SO_4$) and evaporated under reduced pressure to give the title compound as white solid (1.36 g); MS: 365 (M+Na), 343 ($MH^+$); LCMS retention time 3.1 minutes.

Reference 17

2-Cyclohexylmethyl-4-morpholin-4-yl-4-oxo-butyric acid

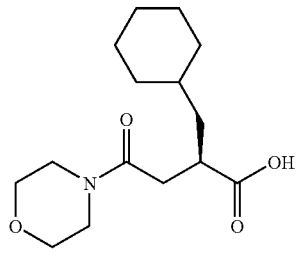

A 0.05 M solution of 1-(4-benzyl-2-oxo-oxazolidin-3-yl)-2-cyclohexylmethyl-4-morpholin-4-yl-butane-1,4-dione (1 g) in 3:1 –THF/$H_2O$ was treated at 0° C. with 8 equivalents of 30% $H_2O_2$ followed by 2.0 equivalents of LiOH. The resulting mixture was stirred at 0–25° C. until the substrate had been consumed (approximately 1 hour). The excess peroxide was quenched at 0° C. with a 10% excess of 1.5 N aqueous $Na_2SO_3$. After buffering to pH 9–10 with aqueous $NaHCO_3$ and evaporation of the THF, the oxazolidone chiral auxiliary was recovered by $MeCl_2$ extraction. The carboxylic acid was isolated by EtOAc extraction of the acidified (pH 1–2) aqueous phase, then recrystallized from EtOAc and hexane to yield 0.58 g of 2-cyclohexylmethyl-4-morpholin-4-yl-4-oxo-butyric acid;

$H^1$ NMR (DMSO-δ): 12(1H, s, COOH), 3.6–3.3(8H, m), 2.8–2.3(3H, m), 1.8–1.1(1H, m), 0.9–0.7(2H, m); MS: 282.2 (M−1), 284.1 (M+1).

Reference Examples (18)–(19) were prepared according to the scheme below.

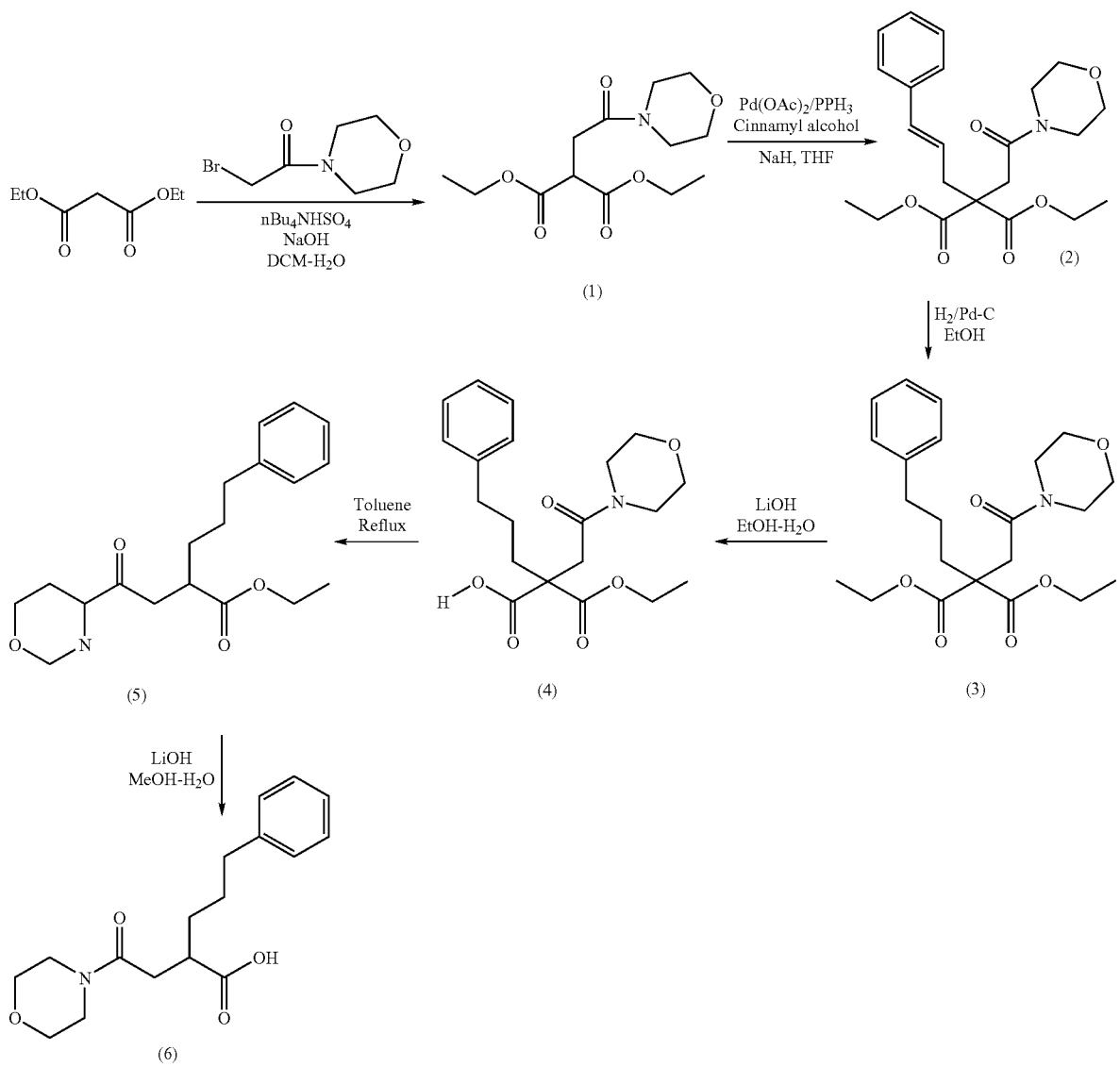

Reference 18

2-(2-Morpholin-4-yl-2-oxo-ethyl)-5-phenyl-pentanoic acid

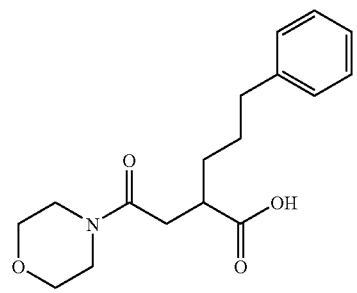

2-(2-Morpholin-4-yl-2-oxo-ethyl)-malonic acid diethyl ester (1)

To a solution of n-tetra butyl ammonium hydrogen sulfate (1.18 g, 3.48 mmol) and NaOH (560 mg, 13.9 mmol) in water (8 ml) was added a solution of 4-(2-bromoacetyl morpholine) (1.45 g, 6.97 mmol) and diethyl malonate (1.34 g, 8.36 mmol) in DCM (8 ml). The mixture was stirred at room temperature for 3 hours, diluted with water (30 ml) and extracted with DCM (2×30 ml). The organic layer was dried (MgSO$_4$) and concentrated in vacuum. The residue was purified by chromatography (silica) eluting with 1:2 v/v ethyl acetate-heptane to give 2-(2-morpholin-4-yl-2-oxo-ethyl)-malonic acid diethyl ester as a colorless oil (1.19 g, 59%); $^1$H NMR (CDCl$_3$) 4.25 (m, 4H), 4.0 (t, J=7.2 Hz, 1H), 3.8–3.45 (m, 8H), 3.0 (d, J=7.4 Hz, 2H), 1.3 (t, J=7.1 Hz, 6H).

2-(2-Morpholin-4-yl-2-oxo-ethyl)-2-(3-phenyl-allyl)-malonic acid diethyl ester (2)

To a mixture of Pd(OAc)$_2$ (17.5 mg, 0.078 mmol) and PPh$_3$ (40.9 mg, 0.156 mmol) in dry THF (2 ml) under N$_2$, cinnamyl alcohol (105.1 mg, 0.78 mmol) was added followed by a solution of 2-(2-morpholin-4-yl-2-oxo-ethyl)-malonic acid diethyl ester (250 mg, 0.87 mmol) and NaH (17.4 mg, 0.43 mmol) in dry THF (3 ml). BF$_3$ (1M in THF, 1 ml, 1 mmol) was then added and the yellow solution was stirred at room temperature for 6.5 hours. The mixture was diluted with ethyl acetate (50 ml) and washed with 1N HCl (10 ml) and brine (2×20 ml). The organic layer was dried (MgSO$_4$), concentrated in vacuum and purified by chromatography eluting with 1:1 v/v ethyl acetate-heptane mixture to give 2-(2-morpholin-4-yl-2-oxo-ethyl)-2-(3-phenyl-allyl)-malonic acid diethyl ester as a thick, yellow oil (266.5 mg, 85%); $^1$H NMR (CDCl$_3$) 7.25 (m, 5H), 6.40 (d, J=15.6 Hz, 1H), 6.1 (dt, J=15.8, 7.7 Hz), 4.2 (q, J=7.1 Hz, 4H), 3.6 (m, 6H), 3.45 (m, 2H), 3.05 (d, J=7.6 Hz, 2H), 3.0 (s, 2H), 1.25 (t, J=7.1 Hz 6H). MS: 404 (MH$^+$)

2-(2-Morpholin-4-yl-2-oxo-ethyl)-2-(3-phenyl-propyl)-malonic acid diethyl ester (3)

A solution of 2-(2-morpholin-4-yl-2-oxo-ethyl)-2-(3-phenyl-allyl)-malonic acid diethyl ester (257 mg, 0.637 mmol) in EtOH (15 ml) was hydrogenated over Pd/C at 55 Psi for 7.5 hrs. The catalyst filtered off over a pad of Celite and the filtrate evaporated under vacuum to give 2-(2-morpholin-4-yl-2-oxo-ethyl)-2-(3-phenyl-propyl)-malonic acid diethyl ester as a light yellow oil (260 mg); $^1$H NMR (CDCl$_3$) 7.4–7.1 (m, 5H), 4.20 (q, J=7.1 Hz, 4H), 3.7–3.4 (m, 8H), 3.0 (s, 2H), 2.6 (t, J=7.6 Hz, 2H), 2.2 (m, 2H), 2.55 (m, 2H), 1.20 (t, J=7.1 Hz, 6H). MS: 406 (MH$^+$).

2-(2-Morpholin-4-yl-2-oxo-ethyl)-2-(3-phenyl-propyl)-malonic acid monoethyl ester (4)

To a solution of 2-(2-morpholin-4-yl-2-oxo-ethyl)-2-(3-phenyl-propyl)-malonic acid diethyl ester (934 mg, 2.3 mmol) in a 2:1 mixture of ethanol and water (12 ml) LiOH.H$_2$O (193.3 mg, 4.61 mmol) was added and heated at 40° C. for 19 hrs. Ethanol was evaporated under reduced pressure, the residual aqueous mixture was acidified to pH 1 and extracted with methylene chloride (2×40 ml). The organic extract was dried with MgSO$_4$ and evaporated under reduced pressure to give 2-(2-morpholin-4-yl-2-oxo-ethyl)-2-(3-phenyl-propyl)-malonic acid monoethyl ester as a thick, yellow oil (831 mg); $^1$H NMR (CDCl$_3$) 7.4–7.1 (m, 6H), 4.25 (q, J=7.1 Hz, 2H), 3.8–3.4 (m, 8H), 3.20 (d, J=16.4 Hz, 1H), 2.9 (d, J=16.4 Hz, 1H), 2.6 (m, 2H), 2.1–1.8 (m, 4H), 1.25 (t, J=7.1 Hz, 3H). MS: 378 (MH$^+$).

2-(2-Morpholin-4-yl-2-oxo-ethyl)-5-phenyl-pentanoic acid ethyl ester (5)

A Solution of 2-(2-morpholin-4-yl-2-oxo-ethyl)-2-(3-phenyl-propyl)-malonic acid monoethyl ester (809 mg, 2.14 mmol) in toluene (25 ml) was heated under reflux for 23 hours. The colorless solution was concentrated under reduced pressure, the residue was taken up in diethyl ether (50 ml), washed with saturated NaHCO$_3$ and dried over MgSO$_4$. The solvent was evaporated under reduced pressure to give 2-(2-morpholin-4-yl-2-oxo-ethyl)-5-phenyl-pentanoic acid ethyl ester as yellow oil (617 mg); $^1$H NMR (CDCl$_3$) 7.3–7.1 (m, 5H), 4.2 (m, 2H), 3.8–3.4 (m, 8H), 3.0 (m ,1H), 2.75 (dd, J=15.9, 9.4 Hz, 1H), 2.65 (m, 2H), 2.35 (dd, J=15.9, 5.1 Hz, 1H), 1.8–1.55 (m, 4H), 1.29 (t, J=7.1 Hz, 3H). MS : 334 (MH$^{30}$ ).

2-(2-Morpholin-4-yl-2-oxo-ethyl)-5-phenvl-pentanoic acid (6)

To a solution of 2-(2-morpholin-4-yl-2-oxo-ethyl)-5-phenyl-pentanoic acid ethyl ester (604 mg, 1.81 mmol) in a 2:1 mixture of MeOH—H2O (12 ml) LiOH.H2O (228 mg, 5.43 mmol) was added and stirred overnight at room temperature. Ethanol was removed under reduced pressure, residue diluted with water (40 ml) and washed with ether. The aqueous layer was acidified to pH1 with 1N HCl and extracted with diethyl ether (3×25 ml). The combined organic extracts were dried with MgSO4 and concentrated under reduced pressure to give 2-(2-morpholin-4-yl-2-oxo-ethyl)-5-phenyl-pentanoic acid as a white solid (492 mg); 1H NMR (CDCl3) 8.0–7.5 (1H), 7.4–7.1 (m, 5H), 3.8–3.4 (m, 8H), 3.0 (m, 1H), 2.8 (dd, J=16.4, 9.6 Hz, 1H), 2.65 (t, J=7.2 Hz, 2H), 2.40 (dd, J=16.4, 4.3 Hz, 1H), 1.9–1.5 (m, 4H). MS: 306 (MH+).

Reference 19

2-(1-Benzyl-cyclopropylmethyl)-4-morpholin-4-yl-4-oxo-butyric acid

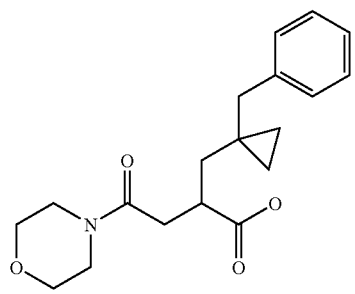

Similarly prepared according to the Scheme illustrated for Reference Example 18 as colorless oil.

$^1$H NMR (CDCl$_3$) 7.25 (m, 5H), 3.65 (m, 6H), 3.45 (m, 2H), 3.2 (m, 1H), 2.9 (d, J=14.4 Hz, 1H), 2.78 (dd, J=16.3, 10.0 Hz, 1H), 2.55 (d, J=14.5 Hz, 1H), 2.48 (dd, J=16.5, 4.0 Hz, 1H), 1.6 (m, 2H), 0.5 (m, 4H).

Reference 20

2-(1-methyl-cyclopentylmethyl)-4-morpholin-4-yl-4-oxo-butyric acid

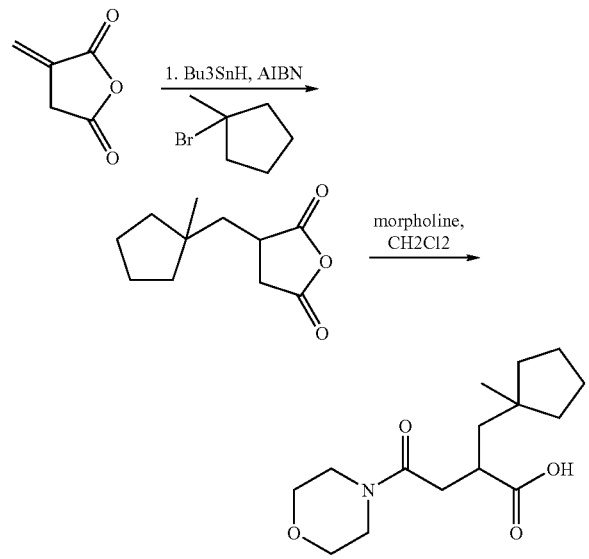

To 1-methylcyclopentanol (5 g, 50 mmol) was added 48% aqu. HBr (15 mL). The mixture was stirred rapidly for 30 min and then was extracted with hexane (2×50 mL). The combined organic layers were washed with water, dried with MgSO$_4$ and evaporated under vacuum. The crude 1-bromo-1-methyl-cyclopentane (6.6 g, 40.5 mmol) was used without further purification.

Tributyltinhydride (2.69 mL, 10 mmol), AIBN (164 mg, 1 mmol), and 1-bromo-1-methyl-cyclopentane (2.4 g, 15 mmol) were added to a solution of itaconic anhydride (1 g, 8.93 mmol) in dry benzene (20 mL) and heated at reflux for 3 hours. After cooling, the benzene was removed under vacuum and the residue was dissolved in dry dichloromethane (20 mL). The solution was cooled to −78° C. and morpholine (1.5 mL) was added dropwise over 2 min. The mixture was allowed to warm to room temperature over 2 hours. The mixture was partitioned between diethylether (100 mL) and sat. aqu. NaHCO$_3$ solution (100 mL). The aqueous layer was extracted two more times with diethylether, was acidified with 6N aqu. HCl and extracted with ethyl acetate (3×50 mL). The combined organic layers were washed with brine, dried with MgSO4 and evaporated under vacuum. The crude 2-(1-methyl-cyclopentylmethyl)-4-morpholin-4-yl-4-oxo-butyric acid (400 mg, 1.41 mmol) was used without further purification.

Reference 21

2-Amino-1-benzoxazol-2-yl-butan-1-one; hydrochloride

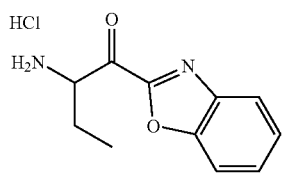

Prepared according to the general procedure for oxidation of amino alcohol to aminoketone template.

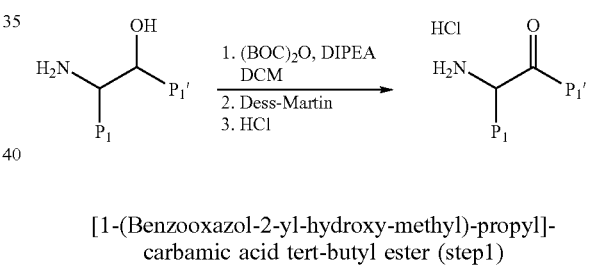

[1-(Benzooxazol-2-yl-hydroxy-methyl)-propyl]-carbamic acid tert-butyl ester (step1)

DIPEA (0.35 ml, 2 mmol) and di-tret-butyl dicarbonate (355 mg, 1.63 mmol) were added to a solution of 2-Amino-1-benzooxazol-2-yl-butan-1-ol (320 mg, 1.55 mmol) in dry methylene chloride (10 ml) and stirred at room temperature for 4 hrs. The reaction was quenched with saturated aqueous NH$_4$Cl and the pH was adjusted to neutral. Oraganic layer separated and the aqueous layer extracted with methylene chloride. The organic extracts were dried over MgSO$_4$ and concentrated under reduced pressure to give [1-(Benzooxazol-2-yl-hydroxy-methyl)-propyl]-carbamic acid tert-butyl ester (500 mg).

[1-(Benzooxazole-2-carbonyl)-propyl]-carbamic acid tert-butyl ester (step2)

Dess-Martin Periodinane (15 wt % in DCM, 8.8 g, 3.1 mmol) was added to a solution of [1-(Benzooxazol-2-yl-hydroxy-methyl)-propyl]-carbamic acid tert-butyl ester (475 mg, 1.55 mmol) in dry methylene chloride (15 ml) and stirred at room temperature for 4 hrs. The reaction was quenched with a solution of Na$_2$S$_2$O$_3$ in aqueous NaHCO$_3$. The organic layer was separated and the aqueous extracted with dichloromethane. The organic extracts were dried over sodium sulfate and concentrated under reduced pressure. Column chromatography on silica eluting with a mixture of heptane and methylene chloride gave the title compound as a off-white powder (0.38 g).

2-Amino-1-benzoxazol-2-yl-butan-1-one; hydrochloride (step3).

Hydrogen chloride (4M in 1,4 dioxane, 1 ml) was added to a solution of [1-(Benzooxazole-2-carbonyl)-propyl]-carbamic acid tert-butyl ester (100 mg, 0.33 mmol) in dry methylene chloride and the reaction mixture was stirred for 4 hours at rt. The reaction mixture was concentrated under reduced pressure to gave the title compound as a yellowish solid (65 mg).

$^1$H NMR (DMSO) δ 0.99 (t, J=7.5 Hz, 3H), 2.20–2.05 (m, 2H), 4.96 (m, 1H), 7.58 (t, J=7.4 Hz, 1H), 7.68 (t, J=7.4 Hz, 1), 7.95 (d, J=8.2 Hz, 1H), 8.06 (d, J=8.2 Hz, 1H), 8.75 (m, 3H); MS: 207(M$^+$)

Reference Examples (22)–(25) were made as shown in the scheme below

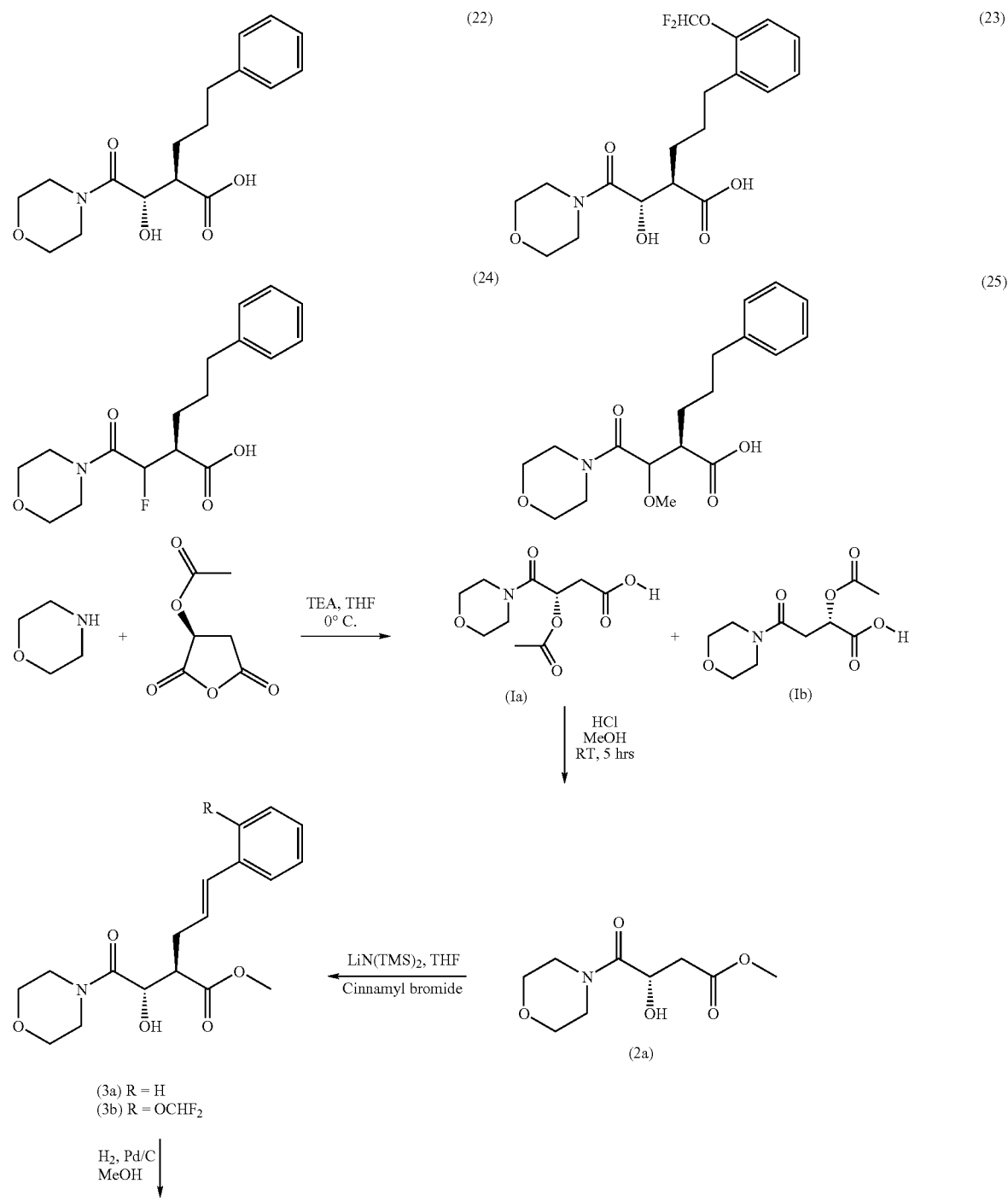

-continued

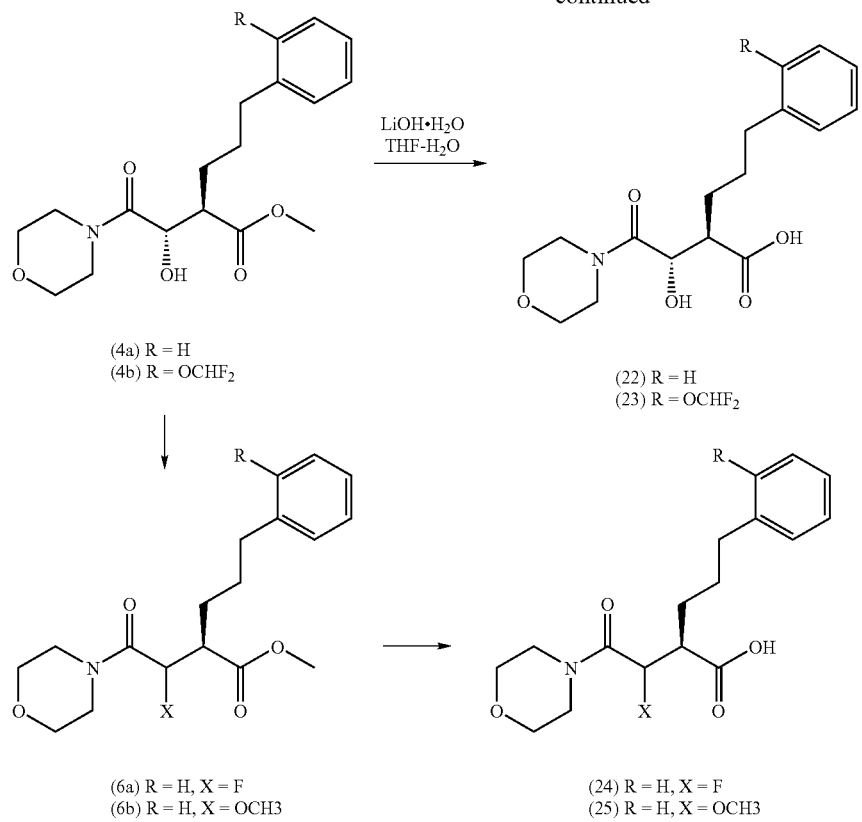

(4a) R = H
(4b) R = OCHF₂

(22) R = H
(23) R = OCHF₂

(6a) R = H, X = F
(6b) R = H, X = OCH3

(24) R = H, X = F
(25) R = H, X = OCH3

(S)-3-Acetoxy-4-morpholin-4-yl-4-oxo-butyric acid (1a) and (S)-2-Acetoxy-4-morpholin-4-yl-4-oxo-butyric acid (1b).

Morpholine (14.48 ml) and Triethylamine (23.14 ml, 166 mmol) were added to an ice-cold solution of Acetic acid (S)-2,5-dioxo-tetrahydro-furan-3-yl ester (25 g, 158.12 mmol) in dry THF (600 ml) and the solution was stirred at room temperature over the week end. Solvent was evaporated under reduced pressure, residue diluted with water, acidified to pH 2 with 1N HCl and extracted with ethyl acetate. Combined organic extracts were dried over MgSO₄ and evaporated under reduced pressure to give a mixture of (S)-3-Acetoxy-4-morpholin-4-yl-4-oxo-butyric acid and 2-Acetoxy-4-morpholin-4-yl-4-oxo-butyric acid (14 g) as white solid.

(S)-3-Hydroxy-4-morpholin-4-yl-4-oxo-butyric acid methyl ester (2a).

To a mixture of (S)-3-Acetoxy-4-morpholin-4-yl-4-oxo-butyric acid and 2-Acetoxy-4-morpholin-4-yl-4-oxo-butyric acid (11 g, 44.8 mmol) in dry methanol (30 mL) HCl in dioxane (4M, 7.3 ml, 29.16 mmol) was added and stirred at room temperature for 5 hrs. The reaction mixture was neutralized with solid NaHCO₃, filtered through a mixture of Celite/Na₂SO₄ (1:1) and concentrated under reduced pressure. Column chromatography on silica eluting with a mixture of ethyl acetate and methylene chloride gave (S)-3-Hydroxy-4-morpholin-4-yl-4-oxo-butyric acid methyl ester (6 g).

(E)-(R)-2-((S)-1-Hydroxy-2-morpholin-4-yl-2-oxo-ethyl)-5-phenyl-pent-4-enoic acid methyl ester (3a).

Lithium hexamethyldisilazide (1M in THF, 14.5 ml, 14.5 mmol) was added to a solution of (S)-3-Hydroxy-4-morpholin-4-yl-4-oxo-butyric acid methyl ester (1.5 g, 6.9 mmol) in dry THF (15 ml) at −78° C. under N₂ and stirred for 30 min. Cinnamyl bromide (1.6 g, 7.32 mmol) was then added, the reaction mixture stirred at −78° C. for 2 hrs, warmed up to room temperature and stirred overnight at room temperature. The reaction was quenched with saturated ammonium chloride solution, adjusted the pH to 6 with 1N HCl and extracted with ethyl acetate. Combined ethyl acetate extracts were dried over MgSO₄ and concentrated under reduced pressure to give yellow solid. Column chromatography on silica eluting with a mixture of ethyl acetate and methylene chloride gave the title compound as pale yellow solid (1.15 g).

(E)-(R)-5-(2-Difluoromethoxy-phenyl)-2-((S)-1-hydroxy-2-morpholin-4-yl-2-oxo-ethyl)-pent-4-enoic acid methyl ester (3b)

It is similarly prepared according to the procedure above but replacing cinnamyl bromide with 1-((E)-3-Bromo-propenyl)-2-difluoromethoxy-benzene.

(R)-2-((S)-1-Hydroxy-2-morpholin-4-yl-2-oxo-ethyl)-5-phenyl-pentanoic acid methyl ester (4a)

A solution of (E)-(R)-2-((S)-1-Hydroxy-2-morpholin-4-yl-2-oxo-ethyl)- 5-phenyl-pent-4-enoic acid methyl ester (1.55 g, 4.65 mmol) in methanol (15 ml) was hydrogenated at 50 psi over Pd/C for 4 hrs. The catalyst was removed by filtration through celite and the filtrate concentrated under reduced pressure to give (R)-2-((S)-1-Hydroxy-2-morpholin-4-yl-2-oxo-ethyl)-5-phenyl-pentanoic acid methyl ester as yellow solid (1.45 g).

(R)-5-(2-Difluoromethoxy-phenyl)-2-((S)-1-hydroxy-2-morpholin-4-yl-2-oxo-ethyl)-pentanoic acid methyl ester (4b).

It is similarly prepared according to the procedure above but using (E)-(R)-5-(2-Difluoromethoxy-phenyl)-2-((S)-1-hydroxy-2-morpholin-4-yl-2-oxo-ethyl)-pent-4-enoic acid methyl ester.

(R)-2-((S)-1-Hydroxy-2-morpholin-4-yl-2-oxo-ethyl)-5-phenyl-pentanoic acid (22)

A solution of (R)-2-((S)-1-Hydroxy-2-morpholin-4-yl-2-oxo-ethyl)-5-phenyl-pentanoic acid methyl ester (230 mg, 0.69 mmol) and LiOH.H$_2$O (57.5 mg, 1.37 mmol) in a mixture of THF and water (2:1, 6 ml) was stirred at room temperature for 2.5 hrs. The reaction was diluted with water and THF removed under reduced pressure. The pH of the aqueous solution was adjusted to 5 with 1N HCl and extracted with ethyl acetate. The combined organic extracts were dried over MgSO$_4$ and evaporated under reduced pressure to give the title compound as white solid (180 mg).
$^1$H NMR (CDCl$_3$) δ 1.92–1.60 (m, 4H), 2.75–2.60 (m, 3H), 3.78–3.45 (m, 9H), 4.5 (d, J=8 Hz, 1H), 7.35–7.18 (m, 5H);
MS: 322(M$^+$).

(R)-5-(2-Difluoromethoxy-phenyl)-2-((S)-1-hydroxy-2-morpholin-4-yl-2-oxo-ethyl)-pentanoic acid (23)

It is similarly prepared according to the procedure above but using (R)-5-(2-Difluoromethoxy-phenyl)-2-((S)-1-hydroxy-2-morpholin-4-yl-2-oxo-ethyl)-pentanoic acid methyl ester.
$^1$H NMR (CDCl$_3$) δ 1.90–1.65 (m, 4H), 2.77–2.68 (m, 3H), 3.70–3.53 (m, 9H), 4,51 (d, J=4.4 Hz, 1H), 6.52 (t, J=74 Hz, 1H), 7.28–7.14 (m, 4H);
MS: 388(M$^+$).

(S)-2-(1-Fluoro-2-morpholin-4-yl-2-oxo-ethyl)-5-phenyl-pentanoic acid methyl ester (6a)

(Diethylamino)sulfur trifluoride (2.0 ml, 15.2 mmol) was added to a ice cold solution of (R)-2-((S)-1-Hydroxy-2-morpholin-4-yl-2-oxo-ethyl)-5-phenyl-pentanoic acid methyl ester (4a) (0.85 g, 2.5 mmol) in dry methylene chloride (15 ml) and the reaction mixture was stirred overnight while warming to room temperature. The reaction was quenched with aqueous NaHCO$_3$ solution and extracted with methylene chloride. The organic extracts were dried over Na$_2$SO$_4$ and concentrated under reduced pressure. Column chromatography on silica eluting with a mixture of ethyl acetate and methylene chloride gave the title compound as a off-white solid (230 mg). $^1$H NMR (CDCl$_3$) δ 1.90–1.58 (m, 4H), 2.78–2.57 (m, 2H), 3.28–3.10 (m, 1H), 3.75 (s, 3H), 3.74–3.45 (m, 8H), 5.40–5.12 (m, 1H), 7.35–7.18 (m, 5H);
MS: 338(M$^+$).

(R)-2-(1-Methoxy-2-morpholin-4-yl-2-oxo-ethyl)-5-phenyl-pentanoic acid methyl ester (6b).

Sodium hydride (60% in mineral oil, 114 mg, 2.86 mmol) was added to a solution of (R)-2-((S)-1-Hydroxy-2-morpholin-4-yl-2-oxo-ethyl)-5-phenyl-pentanoic acid methyl ester (800 mg, 2.38 mmol) in dry dimethylformamide followed by addition of methyl iodide (0.74 ml, 11.9 mmol) and the reaction mixture was stirred for two hours at rt. The reaction was diluted with water and extracted with Ethyl acetate. The organic extracts were washed with water and brine, dried over MgSO4 and concentrated under reduced pressure to give the title compound as a colorless oil solid (660 mg).

(S)-2-(1-Fluoro-2-morpholin-4-yl-2-oxo-ethyl)-5-phenyl-pentanoic acid (24).

It is similarly prepared according to the procedure of (22), but using (S)-2-(1-Fluoro-2-morpholin-4-yl-2-oxo-ethyl)-5-phenyl-pentanoic acid methyl ester (6a).
$^1$H NMR (CDCl$_3$) δ 1.88–1.62 (m, 4H), 2.78–2.64 (m, 2H), 3.30–3.15 (m, 1H), 3.80–3.50 (m, 8H), 5.40–5.16 (m, 1H), 7.36–7.18 (m, 5H), 8.78–8.50 (b, 1H);
MS: 324 (M$^+$).

(R)-2-(1-Methoxy-2-morpholin-4-yl-2-oxo-ethyl)-5-phenyl-pentanoic acid (25).

It is similarly prepared according to the procedure of (22), but using (R)-2-(1-Methoxy-2-morpholin-4-yl-2-oxo-ethyl)-5-phenyl-pentanoic acid methyl ester (6b).
$^1$H NMR (CDCl$_3$) δ 1.90–1.58 (m, 4H), 2.74–2.60 (m, 2H), 2.98–2.84 (m, 1H), 3.36 (s, 3H), 3.78–3.40 (m, 8H), 4.32 (m, 1H), 7.38–7.16 (m, 5H), 9.94–9.56 (b, 1H); MS: 336 (M$^+$).

Reference 26

2-Amino-1-oxazol-2-yl-butan-1-ol

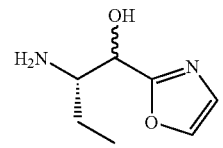

2-Amino-1-oxazol-2-yl-butan-1-ol was prepared according to the following reaction scheme:

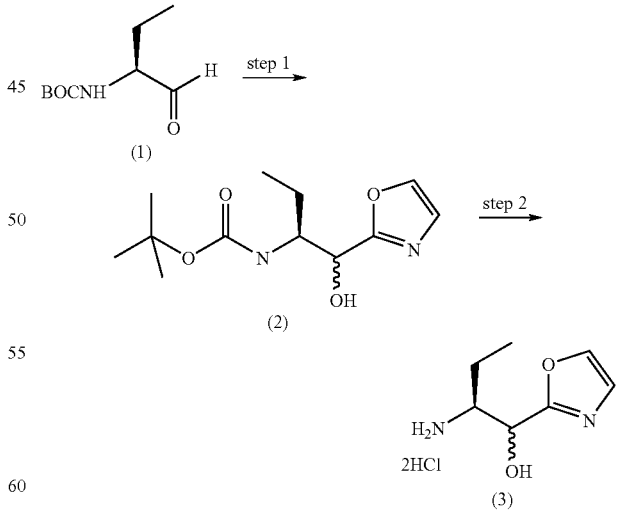

Step 1

Triethylborane (1.0 M in THF, 149.5 ml, 149.5 mmol) was added to oxazole (10.33 g, 149.5 mmol) and stirred for 45 minutes at room temperature. The mixture was then cooled to −78° C. and n-BuLi (2.5 M in hexane, 59.8 ml, 149.5 mmol) was added dropwise and allowed to stir for one hour under nitrogen. Compound (1) (8.0 g, 42.7 mmol) was dissolved in 25 ml of THF and added to the reaction mixture. The reaction was stirred for 5 hours at −78° C. then it was allowed to warm to 0° C. for one hour. The reaction was then cooled back to −78° C. and quenched with 7% acetic acid in ethanol (700 ml) which was allowed to stir overnight at room temperature. The mixture was concentrated in vacuum and the residue was dissolved in ether and filtered. The filtrate was concentrated in vacuum and the residue was dissolved in ethyl acetate washed twice with 0.005 N HCl, twice with saturated sodium bicarbonate and brine. The organic layer was dried over magnesium sulfate, filtered and concentrated in vacuum. The residue was purified on silica using 10–40% ethyl acetate/heptane to give [(S)-1-(Hydroxy-oxazol-2-yl-methyl)-propyl]-carbamic acid tert-butyl ester ((2), 3.85 g).

Step 2

To a solution of [(S)-1-(Hydroxy-oxazol-2-yl-methyl)-propyl]-carbamic acid tert-butyl ester (2) (1.1 g, 4.29 mmol) in dry methylene chloride (10.0 mL), stirring under nitrogen at room temperature, was added 4M HCl (in dioxane, 10.73 ml) dropwise followed by 5 ml of methanol. The reaction was stirred overnight then concentrated in vacuo to give (S)-2-Amino-1-oxazol-2-yl-butan-1-ol (1.2 g) as a brown solid.

Reference 27

(S)-2-Amino-1-oxazol-2-yl-4-phenyl-butan-1-ol

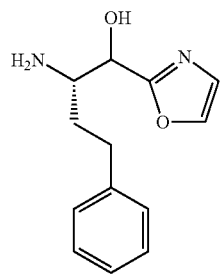

It is similarly prepared according to the procedure for Reference Example 26 LCMS RT=1.1 min., 231 (M+1).

Reference 28

(S)-2-Amino-1-oxazol-2-yl-butan-1-one; hydrochloride

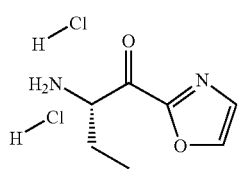

It is similarly prepare according to the general procedure for Reference Example 21 but using [(S)-1-(Hydroxy-oxazol-2-yl-methyl)-propyl]-carbamic acid tert-butyl ester.

EXAMPLE 1

2-(2-Methyl-propane-1-sulfonylmethyl)-4-morpholin-4-yl-4-oxo-N-[(S)-1-(5-phenyl-1,2,4-oxadiazole-3-carbonyl)-propyl]-butyramide A suspension of PS-bound N-cyclohexylcarbodiimide (HL 200–400 mesh cross linked with 2% DVB) from Novabiochem (436 mg, 0.841 mmol, 1.93 mmol/g loading) in methylene chloride (6 mL) was treated with 2-(2-Methyl-propane-1-sulfonylmethyl)-4-morpholin-4-yl-4-oxo-butyric acid (154 mg, 0.480 mmol) in methylene chloride (3 mL) and stirred at room temperature for 10 minutes. A solution of (S)-2-Amino-1-(5-phenyl-1,2,4-oxadiazol-3-yl)-butan-1-ol (96 mg, 0.412 mmol) in methylene chloride (3 mL) was added and the reaction mixture was stirred at room temperature for 3 h. The mixture was filtered and the filtrate was evaporated under reduced pressure. Crude purified by flash chromatography eluting with a mixture of ethyl acetate and heptane to give N-{(S)-1-[Hydroxy-(5-phenyl-1,2,4-oxadiazol-3-yl)-methyl]-propyl}-2-(2-methyl-propane-1-sulfonylmethyl)-4-morpholin-4-yl-4-oxo-butyramide as an off white solid (41 mg) (mixture of diastereoisomers).

MS: 537 (MH$^+$)

A solution of N-{(S)-1-[Hydroxy-(5-phenyl-1,2,4-oxadiazol-3-yl)-methyl]-propyl}-2-(2-methyl-propane-1-sulfonylmethyl)-4-morpholin-4-yl-4-oxo-butyramide (41 mg, 0.076 mmol) in methylene chloride (6 mL) was treated with Dess-Martin periodinane (39 mg, 0.092 mmol) and stirred at room temperature for 90 minutes. The reaction mixture was washed with a solution of $Na_2S_2O_3$ in water (0.26M), saturated aqueous bicarbonate solution and water, dried over $Na_2SO_4$ and the solvent evaporated under reduced pressure. The residue was purified by flash chromatography eluting with a mixture of ethyl acetate and heptane to give 2-(2-Methyl-propane-1-sulfonylmethyl)-4-morpholin-4-yl-4-oxo-N-[(S)-1-(5-phenyl-1,2,4-oxadiazole-3-carbonyl)-propyl]-butyramide as an off white solid (18 mg) (mixture of diastereoisomers).

MS: 535 (MH$^+$).

$^1$H NMR (CDCl$_3$): 8.21 (d, J=7 Hz, 2H), 7.80, 7.64 (d, J=7 Hz, 1H), 7.56 (t, J=7 Hz, 3H), 5.32 (m, 1H), 3.79–3.51 (m, 8H), 3.51–3.36 (m, 2H), 3.08 (2xdd, J=14 Hz & 6 Hz, 1H), 2.97–2.91 (m, 2H), 2.97–2.70 (m, 2H), 2.38 (m, 1H), 2.08 (m, 1H), 1.88 (m, 1H),1.26 (m, 1H), 1.15–1.09 (2xd, J=7 Hz, 6H), 1.03 (2xt, J=7.5 Hz, 3H).

EXAMPLE 2

(R)-2-Cyclohexylmethyl-4-morpholin-4-yl-4-oxo-N-[(S)-1-(5-trifluoromethyl-1,2,4-oxadiazole-3-carbonyl)-propyl]-butyramide

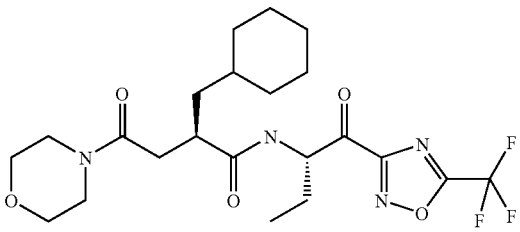

A solution of (R)-2-Cyclohexylmethyl-4-morpholin-4-yl-4-oxo-butyric acid (223 mg, 0.788 mmol) in dimethylformamide (10 ml) was treated successively with (S)-2-Amino-1-(5-trifluoromethyl-1,2,4-oxadiazol-3-yl)-butan-1-ol; compound with trifluoroacetic acid (267 mg, 0.788 mmol), O-(7-azabenzotriazol-1-yl)-N,N,N',N'-tetramethyluronium hexafluorophosphate (299 mg, 0.787 mmol) and diisopropylethylarmine (0.274 ml, 1.576 mmol). Reaction stirred at room temperature overnight. Solvent evaporated under reduced pressure. Residue taken up in ethyl acetate and washed with 1N hydrochloric acid, saturated aqueous bicarbonate solution and water, dried over $Na_2SO_4$ and solvent evaporated under reduced pressure to give (R)-2-Cyclohexylmethyl-N-{(S)-1-[hydroxy-(5-trifluoromethyl-1,2,4-oxadiazol-3-yl)-methyl]-propyl}-4-morpholin-4-yl-4-oxo-butyramide as a yellow solid (324 mg).

MS: 491 ($MH^+$)

A solution of (R)-2-Cyclohexylmethyl-N-{(S)-1-[hydroxy-(5-trifluoromethyl-1,2,4-oxadiazol-3-yl)-methyl]-propyl}-4-morpholin-4-yl-4-oxo-butyramide (324 mg, 0.661 mmol) in methylene chloride (10 ml) was treated with Dess Martin periodinane (308 mg, 0.726 mmol) and stirred at room temperature for 90 minutes. The reaction mixture was washed with an aqueous solution of $Na_2S_2O_3$ (0.26M), saturated aqueous bicarbonate solution and water, dried over $Na_2SO_4$ and the solvent evaporated under reduced pressure. The crude was purified by flash chromatography eluting with a mixture of ethyl acetate and heptane to give (R)-2-Cyclohexylmethyl-4-morpholin-4-yl-4-oxo-N-[(S)-1-(5-trifluoromethyl-1,2,4-oxadiazole-3-carbonyl)-propyl]-butyramide as an off white solid (10 mg).

$^1$H NMR ($CDCl_3$): 6.68 (d, J=6 Hz, 1H), 5.19 (m, 1H), 3.73–3.60 (m, 4H), 3.60–3.52 (m, 2H), 3.52–3.40 (m, 2H), 2.97 (m, 1H), 2.71 (dd, J=16 Hz & 10 Hz, 1H), 2.26 (dd, J=16 Hz & 3 Hz, 1H), 2.14–1.96 (m, 1H), 1.88–1.44 (m, 7H), 1.32–1.07 (m, 5H), 1.02 (t, J=7 Hz, 3H), 0.95–0.76 (m, 2H).

MS: 489 (MH+)

EXAMPLE 3

(R)-4,4-Dimethyl-2-(2-morpholin-4-yl-2-oxo-ethyl)-pentanoic acid[(S)-1-(5-trifluoromethyl-1,2,4-oxadiazole-3-carbonyl)-propyl]-amide

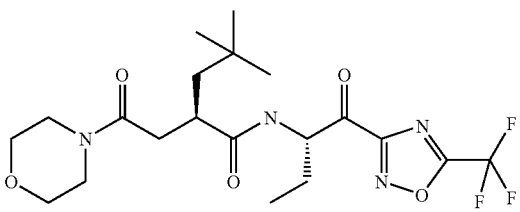

It is similarly prepared according to general procedure given for Example 2 above but using (R)-4,4-Dimethyl-2-(2-morpholin-4-yl-2-oxo-ethyl)-pentanoic acid and(S)-2-Amino-1-(5-trifluoromethyl-1,2,4-oxadiazol-3-yl)-butan-1-ol; compound with trifluoroacetic acid, $^1$H NMR ($CDCl_3$): 6.79 (d, J=5 Hz, 1H), 5.16 (m, 1H), 3.86–3.51 (m, 6H), 3.51–3.28 (m, 2H), 2.96 (m, 1H), 2.72 (dd, J=16 Hz & 10 Hz, 1H), 2.28 (dd, J=16 Hz & 3 Hz, 1H), 2.15–1.96 (m, 1H), 1.96–1.72 (m, 2H), 1.14 (m, 1H), 1.00 (t, J=7 Hz, 3H), 0.88 (s, 9H).

MS: 463 ($MH^+$).

EXAMPLE 4

4-Morpholin-4-yl-4-oxo-2-phenylmethanesulfonylmethyl-N-[(S)-1-(5-trifluoromethyl-1,2,4-oxadiazole-3-carbonyl)-propyl]-butyramide

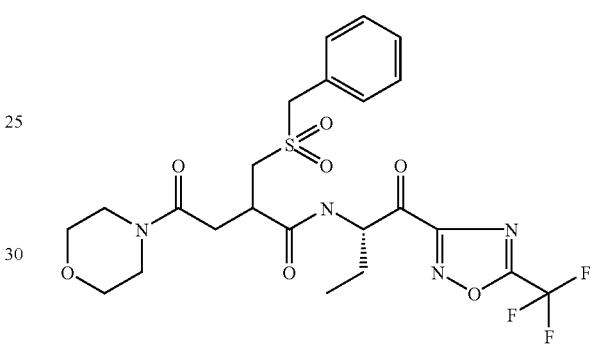

It is similarly prepared according to general procedure given for Example 2 above but using 4-Morpholin-4-yl-4-oxo-2-phenylmethanesulfonylmethyl-butyric acid and (S)-2-Amino-1-(5-trifluoromethyl-1,2,4-oxadiazol-3-yl)-butan-1-ol; compound with trifluoroacetic acid.

$^1$H NMR ($CDCl_3$): 7.82, 7.61 (d, J=6 Hz, 1H), 7.40 (m, 5H), 5.08 (m, 1H), 4.28 (m, 2H), 3.78–3.47 (m, 7H), 3.47–3.30 (m, 3H), 2.91 (dd, J=14 Hz & 7 Hz, 1H), 2.82–2.56 (m, 2H), 2.14–1.96 (m, 1H), 1.94–1.76 (m, 1H), 1.02 (t, J=7.5 Hz, 3H).

MS: 561 ($MH^+$).

EXAMPLE 5

(R)-2-(2-Methyl-propane-1-sulfonylmethyl)-4-morpholin-4-yl-4-oxo-N-[(S)-1-(3-phenyl-1,2,4-oxadiazole-5-carbonyl)-propyl]-butyramide

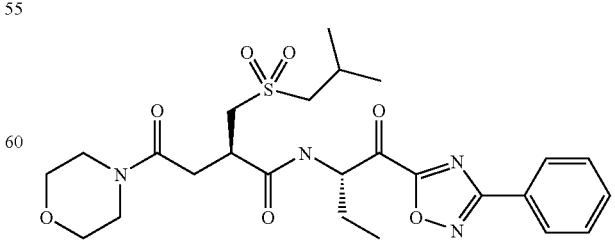

It is similarly prepared according to general procedure given for Example 2 above but using 2-(2-Methyl-propane- 1-sulfonylmethyl)-4-morpholin-4-yl-4-oxo-butyric acid and (S)-2-Amino-1-(3-phenyl-1,2,4-oxadiazol-5-yl)-butan-1-ol.

$^1$H NMR (CDCl$_3$) δ 8.12 (d, 2 H), 7.66 (d, 1 H), 7.54–7.46 (m, 3 H), 5.27 (m, 1 H), 3.67–3.57(m, 7H), 3.51–3.4 (m, 3 H), 3.08 (dd, 1 H), 2.92–2.79 (m, 4H), 2.36 (m, 1 H), 2.11 (m, 1 H), 1.90 (m, 1 H), 1.10 (d, 6 H), 1.05 (t, 3 H).

MS: m/z 535 (M$^+$+H)

EXAMPLE 6

N-[(S)-1-(5-Ethyl-1,2,4-oxadiazole-3-carbonyl)-propyl]-4-morpholin-4-yl-4-oxo-2-phenylmethane-sulfonylmethyl-butyramide

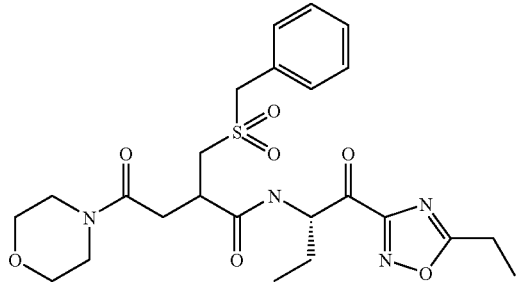

It is similarly prepared according to general procedure given for Example 2 above but using 4-Morpholin-4-yl-4-oxo-2-phenylmethanesulfonylmethyl-butyric acid and (S)-2-Amino-1-(5-ethyl-1,2,4-oxadiazol-3-yl)-butan-1-ol.

1H NMR (CDCl$_3$): δ 0.98 (t, 3H), 1.43 (t, 3H), 1.80 (m, 1H), 2.03 (m, 1H), 2.74 (m, 2H), 2.95 (m, 1H), 2.98 (q, 2H), 3.4–3.71 (m, 1H), 4.25 (dd, 1H), 4.30 (dd, 1H), 5.22 (m, 1H), 7.39 (m, 5H), 7.66 (d, 1H).

LC/MS (2.82 min) m/z=521 (M+H).

EXAMPLE 7

(R)-4-Morpholin-4-yl-4-oxo-2-phenylmethanesulfonylmethyl-N-[(S)-1-(3-phenyl-1,2,4-oxadiazole-5-carbonyl)-propyl]-butyramide

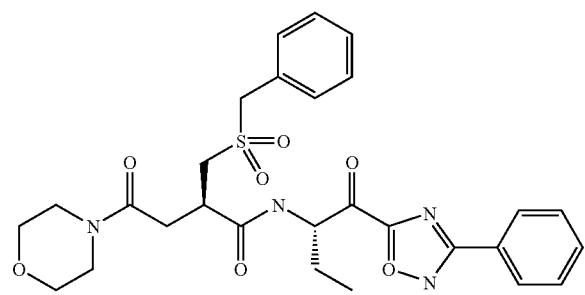

It is similarly prepared according to general procedure given for Example 2 above but using 4-Morpholin-4-yl-4-oxo-2-phenylmethanesulfonylmethyl-butyric acid and (S)-2-Amino-1-(3-phenyl-1,2,4-oxadiazol-5-yl)-butan-1-ol.

1H NMR (CDCl$_3$): δ 1.03 (t, 3H), 1.91 (m, 1H), 2.13 (m, 1H), 2.72 (dd, 1H), 2.79 (dd, 1H), 2.95 (dd, 1H), 3.40 (m, 3H), 3.65 (m, 7H), 4.27 (d, 1H), 4.30 (d, 1H), 5.29 (m, 1H), 7.40 (m, 3H), 7.54 (m, 5H), 8.14 (m, 2H).

MS m/z=569 (M+H).

EXAMPLE 8

4,4-Dimethyl-2-(2-morpholin-4-yl-2-oxo-ethyl)-pentanoic acid[1-(5-ethyl-1,2,4-oxadiazole-3-carbonyl)-propyl]-amide

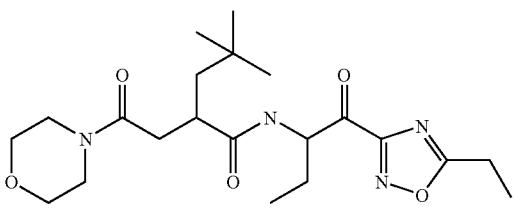

A solution of (R)-4,4-Dimethyl-2-(2-morpholin-4-yl-2-oxo-ethyl)-pentanoic acid (200 mg, 0.778 mmol) in dimethylformamide (10 ml) was treated successively with (S)-2-Amino-1-(5-ethyl-1,2,4-oxadiazol-3-yl)-butan-1-ol; compound with trifluoro-acetic acid (233 mg, 0.779 mmol), O-(7-azabenzotriazol-1-yl)-N,N,N',N'-tetramethyluronium hexafluorophosphate (296 mg, 0.779 mmol) and diisopropylethylamine (0.271 ml, 1.559 mmol). Reaction stirred at room temperature overnight. Solvent evaporated under reduced pressure. Residue taken up in ethyl acetate and washed with 1N hydrochloric acid, saturated aqueous bicarbonate solution and water, dried over Na$_2$SO$_4$ and solvent evaporated under reduced pressure to give (R)-4,4-Dimethyl-2-(2-morpholin-4-yl-2-oxo-ethyl)-pentanoic acid {(S)-1-[(5-ethyl-1,2,4-oxadiazol-3-yl)-hydroxy-methyl]-propyl}-amide as a yellow solid (277 mg).

MS: 425 (MH$^+$)

A solution of (R)-4,4-dimethyl-2-(2-morpholin-4-yl-2-oxo-ethyl)-pentanoic acid {(S)-1-[(5-ethyl-1,2,4-oxadiazol-3-yl)-hydroxy-methyl]-propyl}-amide (277 mg, 0.653 mmol) in methylene chloride (6 ml) was treated with Dess-Martin periodinane (332 mg, 0.783 mmol) and stirred at room temperature for 90 minutes. The reaction mixture was washed with a solution of Na$_2$S$_2$O$_3$ in water (0.26M), saturated aqueous bicarbonate solution and water, dried over Na$_2$SO$_4$ and solvent evaporated under reduced pressure. The residue was purified by flash chromatography eluting with a mixture of ethyl acetate and heptane to give 4,4-Dimethyl-2-(2-morpholin-4-yl-2-oxo-ethyl)-pentanoic acid[1-(5-ethyl-1,2,4-oxadiazole-3-carbonyl)-propyl]-amide as a yellow solid (44 mg) (mixture of diastereoisomers).

$^1$H NMR (CDCl$_3$): 6.60 (d, J=7 Hz, 1H), 5.24 (m, 1H), 3.66–3.54 (m, 4H), 3.54–3.46 (m, 2H), 3.44–3.28 (m, 2H), 2.91 (q, J=8 Hz, 2H), 2.93–2.83 (m, 1H), 2.68 (dd, J=16 Hz & 10 Hz, 1H), 2.20 (dd, J=16 Hz & 4 Hz, 1H), 1.96 (m, 1H), 1.82 (m, 1H), 1.70 (m, 1H), 1.37 (t, J=7 Hz, 3H), 1.09 (m, 1H), 0.88 (t, J=7 Hz, 3H), 0.82 (s, 9H).

MS: 423 (MH$^+$).

EXAMPLE 9

(R)-2-Cyclohexylmethyl-N-[(S)-1-(5-ethyl-1,2,4-oxadiazole-3-carbonyl)-propyl]-4-morpholin-4-yl-4-oxo-butyramide

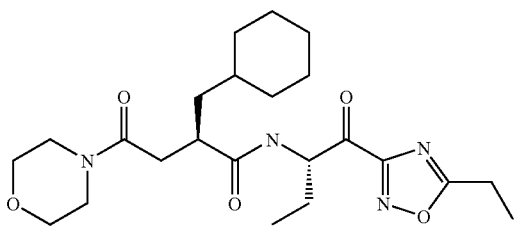

It is similarly prepared according to general procedure given for example 8 above but using (R)-2-Cyclohexylmethyl-4-morpholin-4-yl-4-oxo-butyric acid and (S)-2-Amino-1-(5-ethyl-1,2,4-oxadiazol-3-yl)-butan-1-ol; compound with trifluoro-acetic acid.

$^1$H NMR (CDCl$_3$): 6.53 (d, J=7 Hz, 1H), 5.35 (m, 1H), 3.70–3.61 (m, 4H), 3.61–3.53 (m, 2H), 3.50–3.40 (m, 2H), 3.01–2.92 (m, 11H), 2.99 (q, J=8 Hz, 2H), 2.74 (dd, J=16 Hz & 10 Hz, 1H), 2.25 (dd, J=16 Hz & 3.5 Hz, 1H), 2.05 (m, 1H), 1.85–1.69 (m, 1H), 1.70–1.48 (m, 6H), 1.44 (t, J=7.5 Hz, 3H), 1.32–1.04 (m, 5H), 0.97 (t, J=7.5 Hz, 3H), 0.96–0.78 (m, 2H).

MS: 449 (MH$^+$).

EXAMPLE 10

N-[(S)-1-(Benzoxazole-2-carbonyl)-butyl]-2-(1-benzyl-cyclopropylmethyl)-4-morpholin-4-yl-4-oxo-butyramide

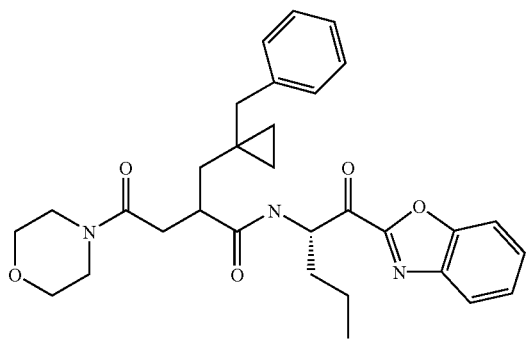

To a solution of 2-(1-Benzyl-cyclopropylmethyl)-4-morpholin-4-yl-4-oxo-butyric acid (53 mg, 0.16 mmol) in dry DCM (4.5 mL) under N$_2$ was added PS-bound N-cyclohexylcarbodiimide (HL 200–400 mesh cross-linked with 2% DVB) from Novabiochem (188 mg, 0.0.32 mmol, 1.93 mmol/g loading) followed by Hydroxybenzotriazole (36.7 mg, 0.27 mmol). After stirring at room temperature for 15 min, (S)-2-Amino-1-benzoxazol-2-yl-pentan-1-ol (35.2 mg, 0.16 mmol) was added and the reaction mixture was stirred over night at room temperature. Silacycle trisamine (222 mg, 0.8 mmol, 3.6 mmol/g loading) was then added and the mixture was stirred for 2 hrs. Solid filtered off and the filtrate evaporated under reduced pressure to give yellow solid (80 mg). The crude was purified by silica gel column chromatography eluting with a mixture of ethyl acetate and heptane to give N-[(S)-1-(Benzoxazol-2-yl-hydroxy-methyl)-butyl]-2-(1-benzyl-cyclopropylmethyl)-4-morpholin-4-yl-4-oxo-butyramide (55 mg).

To a solution of N-[(S)-1-(Benzoxazol-2-yl-hydroxy-methyl)-butyl]-2-(1-benzyl-cyclopropylmethyl)-4-morpholin-4-yl-4-oxo-butyramide (55 mg, 0.103 mmol) in dry dichloromethane under N$_2$ was added a solution of Dess-Martin Periodinane solution in dichloromethane (15% wt in DCM, 0.206 mmol) and stirred at room temperature for 1 hr. The mixture was quenched with a solution Na$_2$SO$_3$ (65.4 mg) in saturated NaHCO$_3$ (20 mL). The aqueous layer was extracted with dichloromethane (2×25 mL). Organic extracts dried (MgSO$_4$) and concentrated under reduced pressure. Residue purified by silica gel column chromatography eluting with a mixture of ethyl acetate and heptane (1:1 then 2:1) to give N-[(S)-1-(Benzoxazole-2-carbonyl)-butyl]-2-(1-benzyl-cyclopropylmethyl)-4-morpholin-4-yl-4-oxo-butyramide as white solid (43 mg).

$^1$H NMR (CDCl$_3$): 7.92 (d, J=8 Hz, 1H), 7.67 (d, J=8 Hz, 1H), 7.56 (t, J=7.5 Hz, 1H), 7.47 (t, J=7.5 Hz, 1H), 7.42–7.14 (m, 5H), 6.78, 6.64 (d, J=7 Hz, 1H), 5.63 (m, 1H), 3.84–3.53 (m, 6H), 3.53–3.32 (m, 2H), 3.18 (m, 1H), 2.88–2.58 (m, 2H), 2.50 (d, J=14.5 Hz, 1H), 2.30 (m, 1H), 2.08 (m, 1H), 1.82 (m, 1H), 1.58–1.36 (m, 4H), 0.98 (t, J=7 Hz, 3H), 0.58–0.26 (m, 4H).

MS: 532 (MH$^+$).

EXAMPLE 11

N-[(S)-1-(Benzoxazole-2-carbonyl)-butyl]-4-morpholin-4-yl-4-oxo-2-(2-phenyl-cyclopropylmethyl)-butyramide

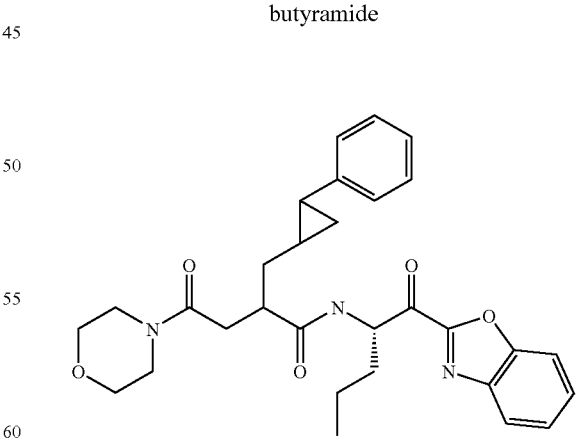

It is similarly prepared according to general procedure given for example 10 above but using 4-Morpholin-4-yl-4-oxo-2-(2-phenyl-cyclopropylmethyl)-butyric acid and (S)-2-Amino-1-benzoxazol-2-yl-pentan-1-ol.

LC/MS: RT=3.39 min, MH$^+$=518.

EXAMPLE 12

(R)-4,4-Dimethyl-2-(2-morpholin-4-yl-2-oxo-ethyl)-pentanoic acid[(S)-1-(benzoxazole-2-carbonyl)-butyl]-amide

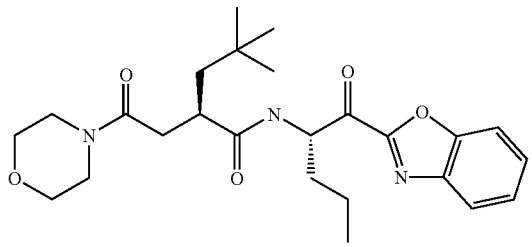

It is similarly prepared according to general procedure given for example 10 above but using (R)-4,4-Dimethyl-2-(2-morpholin-4-yl-2-oxo-ethyl)-pentanoic acid and (S)-2-Amino-1-benzoxazol-2-yl-pentan-1-ol.

$^1$H NMR (CDCl$_3$): 7.91 (d, J=8 Hz, 1H), 7.66 (d, J=8 Hz, 1H), 7.55 (dt, J=8 Hz & 1.2 Hz, 1H), 7.47 (dt, J=8 Hz & 1.2 Hz, 1H), 6.79 (d, J=7 Hz, 1H), 5.61 (m, 1H), 3.75–3.58 (m, 6H), 3.56–3.42 (m, 2H), 3.01 (m, 1H), 2.78 (dd, J=16 Hz & 10 Hz, 1H), 2.30 (dd, J=16 Hz & 4 Hz, 1H), 2.11–2.01 (m, 1H), 1.99–1.74 (m, 2H), 1.54–1.41 (m, 2H), 1.18 (dd, J=14 Hz & 3 Hz, 1H), 0.97 (t, J=7 Hz, 3H), 0.90 (s, 9H).

MS: 458 (MH$^+$).

EXAMPLE 13

(R)-4,4-Dimethyl-2-(2-morpholin-4-yl-2-oxo-ethyl)-pentanoic acid[1-(3-phenyl-1,2,4-oxadiazole-5-carbonyl)-propyl]-amide

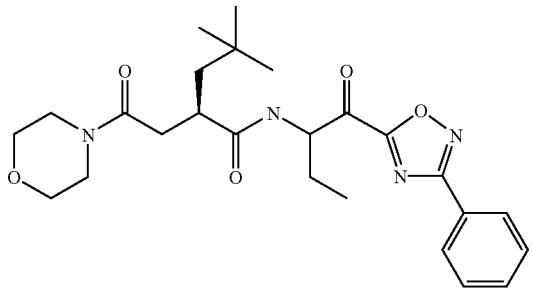

It is similarly prepared according to general procedure given for example 10 above but using 4,4-Dimethyl-2-(2-morpholin-4-yl-2-oxo-ethyl)-pentanoic acid and (S)-2-Amino-1-(3-phenyl-1,2,4-oxadiazol-5-yl)-butan-1-ol.

$^1$H NMR (CDCl$_3$): 8.15 (dd, J=8 Hz & 1.6 Hz, 2H), 7.57–7.52 (m, 3H), 6.86 (d, J=6 Hz, 1H), 5.36 (dd, J=12 Hz & 7 Hz, 1H), 3.76–3.54 (m, 6H), 3.54–3.34 (m, 2H), 3.07–2.93 (m, 1H), 2.78 (dd, J=16 Hz & 10 Hz, 1H), 2.32 (dd, J=16 Hz & 3 Hz, 1H), 2.15 (m, 1H), 2.00–1.80 (m, 2H), 1.19 (dd, J=14 Hz & 3 Hz, 1H), 1.05 (t, J=7.5 Hz, 3H), 0.91 (s, 9H).

MS: 471 (MH$^+$).

EXAMPLE 14

(R)-4,4-Dimethyl-2-(2-morpholin-4-yl-2-oxo-ethyl)-5-phenyl-pentanoic acid [1-(3-phenyl-1,2,4-oxadiazole-5-carbonyl)-propyl]-amide

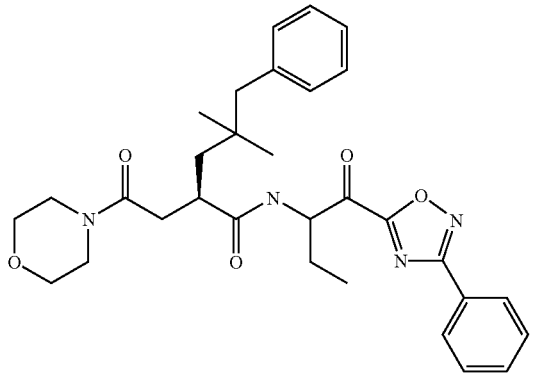

It is similarly prepared (as mixture of diastereoisomers) according to general procedure given for example 10 above but using (R)-4,4-Dimethyl-2-(2-morpholin-4-yl-2-oxo-ethyl)-5-phenyl-pentanoic acid and 2-Amino-1-(3-phenyl-1,2,4-oxadiazol-5-yl)-butan-1-ol $^1$H NMR (CDCl$_3$): 8.15 (dd, J=8 Hz & 1.6 Hz, 2H), 7.61–7.44 (m, 3H), 7.32–7.16 (m, 7.09 (d, J=6.6 Hz, 2H), 6.93 (d, J=6.5 Hz, 1H), 5.35 (dd, J=12 Hz & 7 Hz, 1H), 3.76–3.54 (m, 6H), 3.52–3.34 (m, 2H), 3.11 (m, 1H), 2.76 (dd, J=16 Hz & 10 Hz, 1H), 2.53 (s, 2H), 2.29 (dd, J=16 Hz & 3 Hz, 1H), 2.07 (m, 1H), 2.01 (m, 1H), 1.90 (m, 1H), 1.22 (dd, J=14 Hz & 3 Hz, 1H), 1.05 (t, J=7 Hz, 3H), 0.88 (s, 6H)

MS : 547 (MH$^+$).

EXAMPLE 15

4,4-Dimethyl-2-(2-morpholin-4-yl-2-oxo-ethyl)-5-phenyl-pentanoic acid[(S)-1-(benzoxazole-2-carbonyl)-butyl]-amide

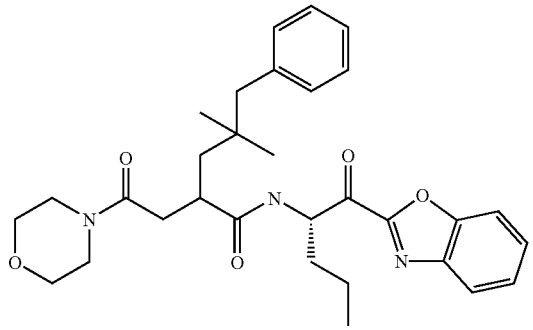

It is similarly prepared according to general procedure given for example 10 above but using (R)-4,4-Dimethyl-2-(2-morpholin-4-yl-2-oxo-ethyl)-5-phenyl-pentanoic acid and (S)-2-Amino-1-benzoxazol-2-yl-pentan-1-ol.

$^1$H NMR (CDCl$_3$): 7.91 (d, J=7.6 Hz, 1H), 7.66 (d, J=8.1 Hz, 1H), 7.55 (dt, J=7 Hz & 1 Hz, 1H), 7.47 (dt, J=8 Hz & 1 Hz, 1H), 7.30–7.15 (m, 3H,) 7.09 (d, J=8 Hz, 2H), 6.86 (d,

J=7 Hz, 1H), 5.62 (m, 1H), 3.75–3.55 (m, 6H), 3.54–3.38 (m, 2H), 3.12 (m, 1H), 2.77 (dd, J=16 Hz & 10 Hz, 1H), 2.52 (s, 2H), 2.27 (dd, J=16 Hz & 4 Hz, 1H), 2.13–1.94 (m, 2H), 1.81 (m, 1H), 1.47 (m, 2H), 1.21 (dd, J=14 Hz & 3 Hz, 1H), 0.98 (t, J=7 Hz, 3H), 0.88 (s, 6H).

MS: 534 (MH$^+$), 0.88(2xS, 6H).

EXAMPLE 18

(R)-4,4-Dimethyl-2-(2-morpholin-4-yl-2-oxo-ethyl)-5-phenyl-pentanoic acid[(S)-1-(5-ethyl-1,2,4-oxadiazole-3-carbonyl)-propyl]-amide

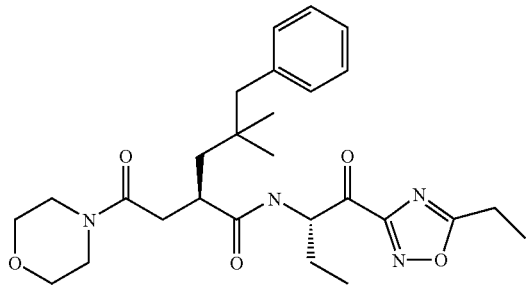

It is similarly prepared according to the general procedure for Example 10.

$^H$NMR (CDCl$_3$), (ppm): 7.20–7.29(m, 3H), 7.10–7.19(d, 2H), 6.78–6.80(d, H), 5.31–5.35(m, H), 3.61–3.68 (m, 6H), 3.44–3.48(m, 2H), 3.06–3.21(m, H), 2.96–3.03(q, 2H), 2.73–2.82(dd, H), 2.53(s, 2H), 2.24–2.31(dd, H), 1.98–2.18 (m, 2H), 1.78–1.85(m, H), 1.43–1.48(t, 3H), 1.19–1.24(dd, H), 0.96–1.01(t, 3H), 0.89(s, 3H), 0.88(s, 3H).

MS: 499 (MH$^+$).

EXAMPLE 19

(R)-4,4-Dimethyl-2-(2-morpholin-4-yl-2-oxo-ethyl)-5-phenyl-pentanoic acid[(S)-1-(5-trifluoromethyl-1,2,4-oxadiazole-3-carbonyl)-propyl]-amide

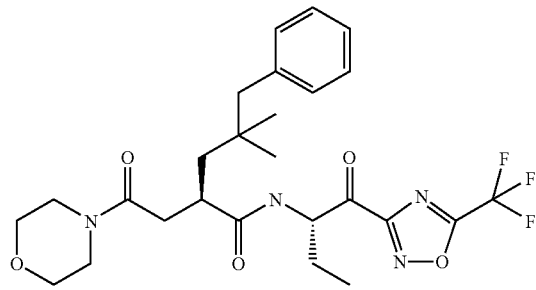

It is similarly prepared according to the general procedure for Example 10.

$^H$NMR (CDCl$_3$), (ppm): 7.19–7.30(m, 3H), 7.10–7.13(d, 211), 6.89–6.91(d, H), 5.15–5.32(m, H), 3.60–3.73 (m, 6H), 3.44–3.46(m, 2H), 3.05–3.14(m, H), 2.70–2.78(dd, H), 2.53 (s, 2H), 2.25–2.32(dd, H), 1.98–2.15(m, H), 1.78–1.90(m, H), 1.27–1.32(m, H), 1.17–1.22(dd, H), 1.01–1.06(t, 3H), 0.89(s, 3H), 0.87(s, 3H).

MS: 539 (MH$^+$).

EXAMPLE 20

(R)-2-(1-Benzyl-cyclopropylmethyl)-N-[(S)-1-(5-ethyl-1,2,4-oxadiazole-3-carbonyl)-propyl]-4-morpholin-4-yl-4-oxo-butyramide

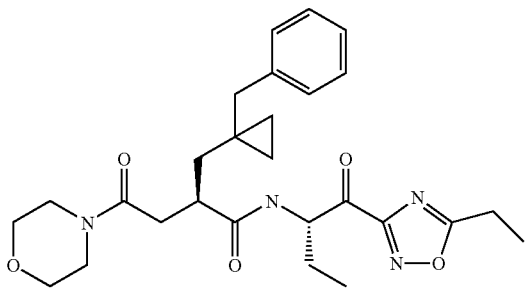

It is similarly prepared according to general procedure given for example 10 above but using (R)-2-(1-Benzyl-cyclopropylmethyl)-4-morpholin-4-yl-4-oxo-butyric acid and (S)-2-Amino-1-(5-ethyl-1,2,4-oxadiazol-3-yl)-butan-1-ol; compound with trifluoro-acetic acid.

$^H$NMR (CDCl3), (ppm): 7.19–7.36(m, 5H), 6.39–6.55(d, H), 5.30–5.44(m, 1H), 3.52–3.67 (m, 6H), 3.37–3.52(m, 2H), 3.06–3.17(m, 1H), 2.98–3.06(q, 2H), 2.66–2.83(dd, 1H), 2.55–2.85(dd, 2H), 2.25–2.32(dd, H), 2.03–2.15(m, 1H), 1.74–1.84(m, 1H), 1.44–1.49(t, 3H), 1.25–1.59(m, 2H), 0.96–1.01(t, 3H), 0.30–0.56(m, 4H).

MS: 497 (MH$^+$).

EXAMPLE 21

(R)-5-(2-Difluoromethoxy-phenyl)-4,4-dimethyl-2-(2-morpholin-4-yl -2-oxo-ethyl)-pentanoic acid[(S)-1-(5-ethyl-1,2,4-oxadiazole-3-carbonyl)-propyl]-amide

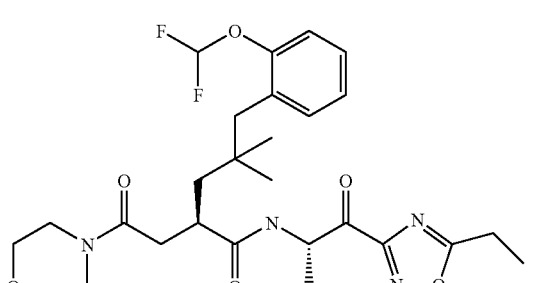

It is similarly prepared according to general procedure for Example 10 above.

$^H$NMR (CDCl$_3$), (ppm): 7.05–7.28(m, 4H), 6.85–6.87(d, 1H), 6.26–6.76(t, H), 5.27–5.34(m, 1H), 3.55–3.68 (m, 6H), 3.41–3.52(m, 2H), 3.08–3.15(m, 1H), 2.96–3.08(q, 2H), 2.72–2.80(dd, H), 2.52–2.69(dd, 2H), 2.29–2.35(dd, 1H), 1.99–2.19(m, 2H), 1.71–1.86(m, 1H), 1.42–1.47(t, 3H), 1.22–1.30(m, 1H), 0.96–1.04(t, 3H), 0.89(s, 3H), 0.86(s, 3H).

MS: 565 (MH$^+$).

EXAMPLE 22

(S)-N-[(S)-1-(Benzoxazole-2-carbonyl)-butyl]-2-(5-methyl-thiophen-2-ylmethyl)-4-morpholin-4-yl-4-oxo-butyramide

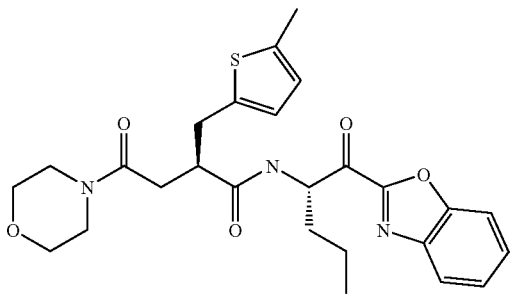

It is similarly prepared according to general procedure for Example 10 above.

$^H$NMR (CDCl$_3$), (ppm): 7.90–7.92(d, 1H), 7.66–7.69(d, 1H), 7.46–7.58(m, 2H), 6.90–6.92(d, 1H), 6.53–6.54(d, 1H), 6.35–6.36(d, 1H), 5.52–5.59(m, 1H), 3.60–3.68 (m, 6H), 3.38–3.60(m, 2H), 3.07–3.20(m, 2H), 2.77–2.91(m, 2H), 2.39–2.46(dd, H), 2.28(s, 3H), 1.94–2.04(m, 1H), 1.73–1.86 (m, 1H), 1.39–1.67(m, 2H), 0.93–0.98(t, 3H).

MS: 498 (MH$^+$).

EXAMPLE 23

(R)-N-[(S)-1-(Benzoxazole-2-carbonyl)-butyl]-2-(1-benzyl-cyclopropvlmethyl)-4-morpholin-4-yl-4-oxo-butyramide

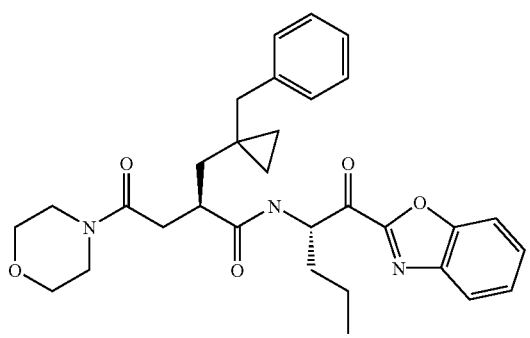

It is similarly prepared according to general procedure for Example 10 above.

$^1$H NMR (CDCl$_3$): 7.92 (d, J=8 Hz, 1H), 7.67 (d, J=8 Hz, 1H), 7.56 (dt, J=7 Hz & 1 Hz, 1H), 7.47 (dt, J=7 Hz & 1 Hz, 1H), 7.37–7.15 (m, 5H), 6.61 (d, J=7 Hz, 1H), 5.64 (m, 1H), 3.63 (m, 4H), 3.63–3.56 (m, 2H), 3.52–3.36 (m, 2H), 3.14 (m 1H), 2.80–2.67 (m, 2H), 2.51 (d, J=15 Hz, 1H), 2.28 (dd, J=16 Hz & 3.5 Hz, 1H), 2.14–1.98 (m, 1H), 1.90–1.75 (m, 1H), 1.60–1.37 (m, 4H), 0.98 (t, J=7 Hz, 3H), 0.62–0.27 (m, 4H).

MS: 532 (MH$^+$).

EXAMPLE 24

(R)-5-(2-Difluoromethoxy-phenyl)-4,4-dimethyl-2-(2-moipholin-4-yl-2-oxo-ethyl)-pentanoic acid[(S)-1-(benzoxazole-2-carbonyl)-butyl]-amide

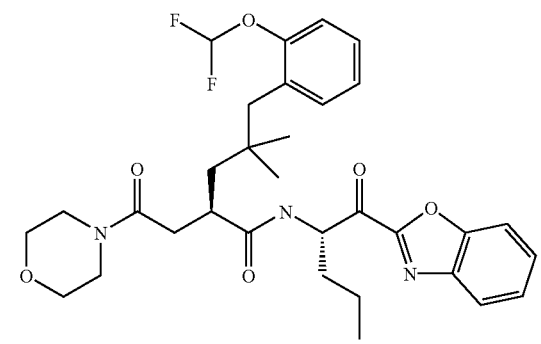

It is similarly prepared according to general procedure for Example 10 above.

$^H$NMR (CDCl$_3$), (ppm): 7.89–7.91(d, H), 7.64–7.67(d, H), 7.43–7.64(m, 2H), 7.04–7.23(m, 4H), 6.86–6.88(d, H), 6.256–6.74(t, H), 5.58–5.65(m, H), 3.57–3.68 (m, 6H), 3.46–3.57(m, 2H), 3.11–3.17(m, H), 2.73–2.82 (dd, H), 2.52–2.68(dd, 2H), 2.29–2.36(dd, H), 1.99–2.11(m, 2H), 1.76–1.86(m, H), 1.42–1.54(m, 2H), 0.95–1.00(t, 3H), 0.89 (s, 3H). 1.34–1.10 (dd, 1H).

MS: 600 (MH$^+$).

EXAMPLE 25

2-(2-Morpholin-4-yl-2-oxo-ethyl)-5-phenyl-pentanoic acid[(S)-1-(oxazole-2-carbonyl)-3-phenyl-propyl]-amide (mixture of diastereoisomers)

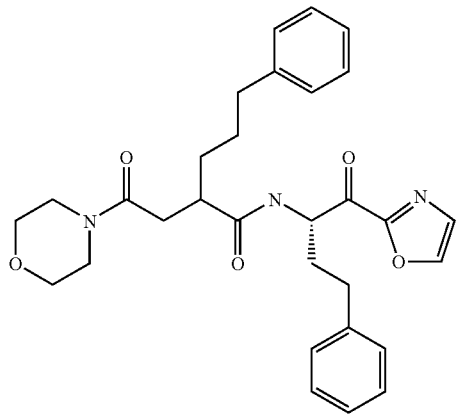

It is similarly prepared according to general procedure for Example 10 above but using 2-(2-Morpholin-4-yl-2-oxo-ethyl)-5-phenyl-pentanoic acid and (S)-2-Amino-1-oxazol-2-yl-4-phenyl-butan-1-ol.

$^1$H NMR (CDCl$_3$): 7.80 (d, J=4.5 Hz, 1H), 7.34 (d, J=6 Hz, 1H), 7.30–7.25 (m, 1H), 7.25–7.20 (m, 3H), 7.20–7.12 (m, 5H), 7.12–7.06 (m, 1H), 6.92, 6.69 (d, J=8 Hz, 1H), 5.54 (m, 1H), 3.73–3.60 (m, 4H), 3.60–3.52 (m, 2H), 3.48–3.38 (m, 2H), 3.00–2.80 (m, 1H), 2.80–2.32 (m, 5H), 2.43–2.22 (m, 2H), 2.05 (m, 1H), 1.87–1.53 (m, 3H), 1.53–1.37 (m, 1H).

MS: 518 (MH$^+$).

EXAMPLE 26

4-Morpholin-4-yl-N-[1-(oxazole-2-carbonyl)-3-phenyl-propyl]-4-oxo-2-(2-phenyl-cyclopropylmethyl)-butyramide (mixture of diastereoisomers)

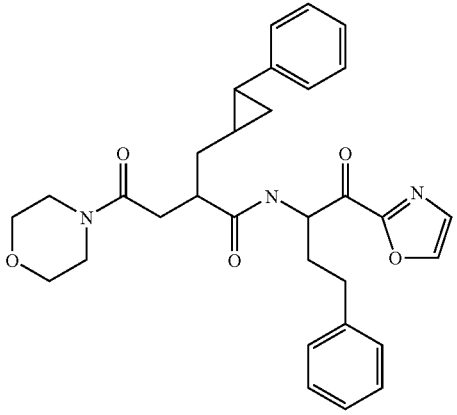

It is similarly prepared according to general procedure given for example X above but using 4-Morpholin-4-yl-4-oxo-2-(2-phenyl-cyclopropylmethyl)-butyric acid and (S)-2-Amino-1-oxazol-2-yl-4-phenyl-butan-1-ol.

$^1$H NMR (CDCl$_3$): 7.80 (t, J=2 Hz, 1H), 7.34 (d, J=6 Hz, 1H), 7.25–7.17 (m, 4H), 7.15–7.08 (m, 2H), 7.08–6.97 (m, 3H), 6.96–6.83 (m, 1H), 6.77, 6.52 (d, J=7 Hz, 1H), 5.47 (m, 1H), 3.73–3.60 (m, 4H), 3.60–3.53 (m, 2H), 3.53–3.32 (m, 2H), 3.04 (m, 1H), 2.89–2.51 (m, 3H), 2.46–2.14 (m, 2H), 2.12–1.77 (m, 2H), 1.75–1.56 (m, 2H), 1.54–1.33 (m, 1H), 1.01–0.73 (m, 2H).
MS: 530 (MH$^+$).

EXAMPLE 27

(R)-2-Cyclohexylmethyl-4-morpholin-4-yl-N-[(S)-1-(oxazole-2-carbonyl)-3-phenyl-propyl]-4-oxo-butyramide

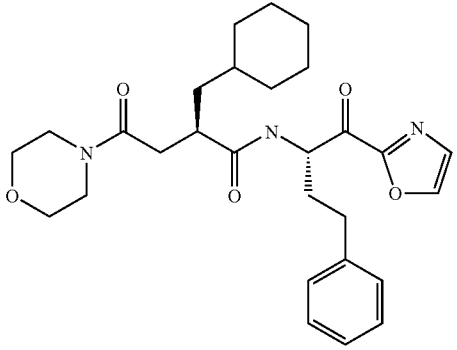

It is similarly prepared according to the general procedure for example 10 but using (S)-2-Amino-1-oxazol-2-yl-4-phenyl-butan-1-ol and 2-Cyclohexylmethyl-4-morpholin-4-yl-4-oxo-butyric acid.

$^1$H NMR: (CDCl$_3$) 7.80 (s, 1H), 7.40(s, 1H), 7.30–7.05 (m, 5H), 6.70 (d, 1H), 5.65–5.50 (m, 1H), 3.75–3.3(m, 8H), 3.10–2.90(m, 1H), 2.90–2.60(m, 3H), 2.45–2.20(m, 2H), 2.10–1.90 (m, 1H), 1.90–1.45(m, 6H), 1.35–1.00(m, 5H), 1.00–0.75(m, 2H)

LCMS: RT=3.25 min. M+1=496.4.

EXAMPLE 28

(R)-4,4-Dimethyl-2-(2-morpholin-4-yl-2-oxo-ethyl)-pentanoic acid[(S)-1-(5-phenyl-1,2,4-oxadiazole-3-carbonyl)-propyl-amide

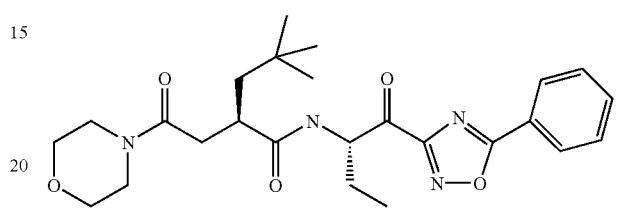

It is similarly prepared according to the general procedure for example 10.

$^1$HNMR: (CDCl$_3$) 8.10 (d, 2H), 7.50–7.70 (m, 3H), 6.73 (d, 1H) 5.40 (m, 1H), 3.58–3.70 (m, 6H), 3.45 (m, 2H), 2.96 (m, 1H), 2.75 (dd, 1H), 2.30 (dd, 1H), 2.10 (m, 1H), 1.75–1.95(m, 2H), 1.18 (dd, 1H), 0.98(t, 3H), 0.90(s, 9H).

LCMS: RT=3.20 min. M+1=471.2.

EXAMPLE 29

3-Phenylmethanesulfonyl-N-[(S)-1-(5-phenyl-1,2,4-oxadiazole-3-carbonyl)-propyl]- 2-(tetrahydro-pyran-4-yloxymethyl)-propionamide

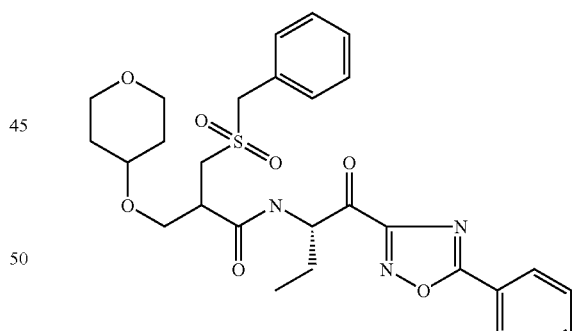

It is similarly prepared according to general procedure given for Example 1 above but using 2-Phenylmethanesulfonylmethyl-3-(tetrahydro-pyran-4-yloxy)-propionic acid and (S)-2-amino-1-(5-phenyl-1,2,4-oxadiazol-3-yl)-butan-1-ol.

$^1$H NMR (CDCl$_3$): 8.20 (d, J=7 Hz, 2H), 7.64 (m, 1H), 7.55 (t, J=7 Hz, 2H), 7.47–7.33 (m, 6H), 5.49 (m, 1H), 4.28 (m, 2H), 3.98–3.85 (m, 2H), 3.81–3.65 (m, 2H), 3.64–3.50 (m, 3.49–3.37 (m, 2H), 3.19 (m, 1H), 2.92 (2xdd, J=14 Hz & 6.5 Hz, 1H), 2.24–2.04 (m, 1H), 2.00–1.77 (m, 3H), 1.72–1.51 (m, 2H), 0.98 (2xt, J=10 Hz & 7.5 Hz, 3H).

MS: 556 (MH$^+$).

EXAMPLE 30

(R)-4,4,6-Trimethyl-2-(2-morpholin-4-yl-2-oxo-ethyl)-heptanoic acid[(S)-1-(5-ethyl-1,2,4-oxadiazole-3-carbonyl)-propyl]-amide

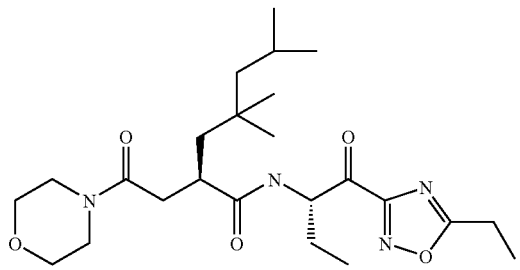

It is similarly prepared according to the general procedure for example 10.
LCMS: RT=3.35 min. M+1=465.

EXAMPLE 31

N-[(S)-1-(Benzoxazole-2-carbonyl)-2,2-dimethyl-propyl]-4-morpholin-4-yl-4-oxo-2-phenylmethane-sulfonylmethyl-butyramide

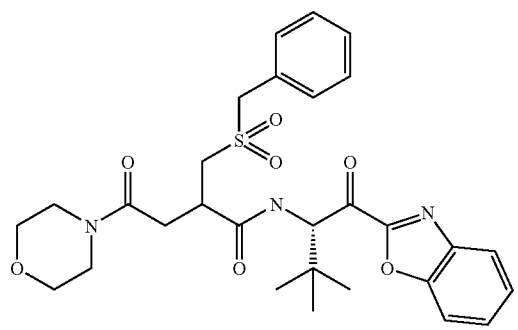

It is similarly prepared according to the procedure for Example 34.
LCMS: RT=3.2 min. M+1=570.

EXAMPLE 32

(R)-4,4,6-Trimethyl-2-(2-morpholin-4-yl-2-oxo-ethyl)-heptanoic acid[(S)-1-(oxazole-2-carbonyl)-propyl]-amide

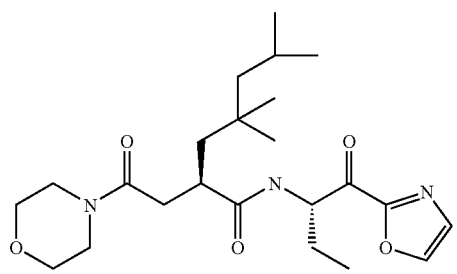

It is similarly prepared according to the general procedure for Example 10 using (S)-2-Amino-1-oxazol-2-yl-butan-1-one; hydrochloride as the amino component and (R)-4,4,6-Trimethyl-2-(2-morpholin-4-yl-2-oxo-ethyl)-heptanoic acid as the acidic component but without further oxidation step.
LCMS: RT=8.13 min. M+1=436. M+Na=458.

EXAMPLE 33

(R)-4,4,6-Trimethyl-2-(2-morpholin-4-yl-2-oxo-ethyl)-heptanoic acid[(S)-1-(benzoxazole-2-carbonyl)-butyl]-amide

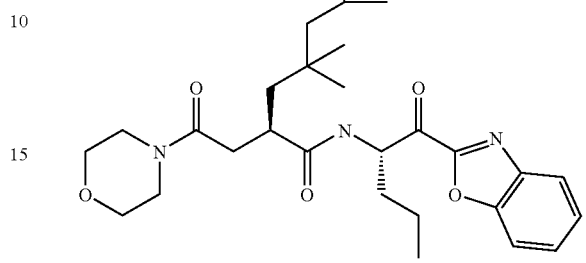

It is similarly prepared according to general procedure given for example 10.
LCMS: RT=3.65 min. M+1=500

EXAMPLE 34

(S)-2-(1-Fluoro-2-morpholin-4-yl-2-oxo-ethyl)-5-phenyl-pentanoic acid[1-(benzoxazole-2-carbonyl)-propyl]-amide

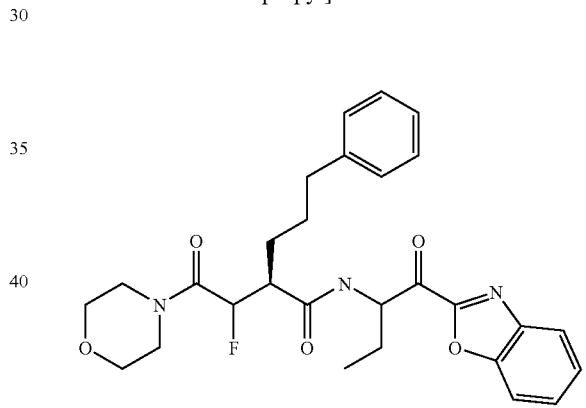

PyBOP (86 mg, 0.16 mmol), DIPEA (0.065 ml, 0.37 mmol) and 2-Amino-1-benzoxazol-2-yl-butan-1-(36 mg, 0.15 mmol) were added to a solution of (S)-2-(1-Fluoro-2-morpholin-4-yl-2-oxo-ethyl)-5-phenyl-pentanoic acid (7a) (50 mg, 0.15 mmol) in dry methylene chloride (4 ml) and the reaction mixture was stirred overnight at room temperature. The reaction was quenched with water, the solvent remove under reduced pressure, the aqueous was extracted with ethyl acetate, and the organic extracts were dried over MgSO4 and evaporated under reduced pressure. Column chromatography on silica eluting with a mixture of ethyl acetate and heptane gave (S)-2-(1-Fluoro-2-morpholin-4-yl-2-oxo-ethyl)-5-phenyl-pentanoic acid[1-(benzoxazol-2-yl-hydroxy-methyl)-propyl]-amide as a white solid (38 mg).

Dess-Martin Periodinane (15 wt % in DCM, 0.15 mmol, 424 mg) was added to a solution of (S)-2-(1-Fluoro-2-morpholin-4-yl-2-oxo-ethyl)-5-phenyl-pentanoic acid[1-(benzoxazol-2-yl-hydroxy-methyl)-propyl]-amide (0.074 mmol) in dry methylene chloride and stirred for three hours. The reaction was quenched with $Na_2S_2O_3$ (0.37 mmol, 56 mg) in aqueous $NaHCO_3$, the organic layer was separated, the aqueous extracted once more with methylene chloride, the organic extracts were dried over Na₂SO₄ and concentrated under reduced pressure. Column chromatography on silica eluting with a mixture of ethyl acetate and methylene chloride gave the title compound as a white solide (30 mg).

¹H NMR (CDCl₃) δ 1.02 (t, 3H), 2.26–1.40 (m, 2+2+2H), 2.78–2.58 (m, 2H), 3.24–3.02 (m, 1H), 3.75–3.48 (m, 8H), 5.38–5.08 (m, 1H), 5.78–5.52 (m, 1H), 6.88–6.56 (m, 1H), 7.36–7.15 (m, 5H), 7.60–7.42 (m, 2H), 7.70 (m, 1H), 7.94 (m, 1H);

MS 510 (M⁺). 532 (M+23).

EXAMPLE 35

(S)-2-(1-Fluoro-2-morpholin-4-yl-2-oxo-ethyl)-5-phenyl-pentanoic acid[(S)-1-(benzoxazole-2-carbonyl)-butyl]-amide

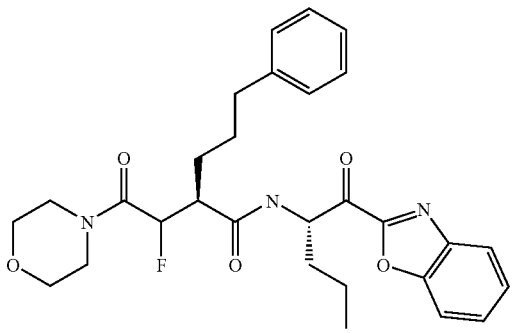

It is similarly prepared according to the procedure for Example 34.

¹H NMR (CDCl₃) δ 0.98 (t, 3H), 2.18–1.40 (m, 2+2+2H), 2.74–2.58 (m, 2H), 3.96–2.98 (m, 1H), 3.78–3.46 (m, 8H), 5.36–5.16 (m, 1H), 5.80–5.58 (m, 1H), 6.72–6.48 (m, 1H), 7.36–7.14 (m, 5H), 7.60–7.48 (m, 2H), 7.65 (m, 1H), 7.92 (m, 1H);

LCMS: RT=3.5 & 3.4 min. M+1=524

EXAMPLE 36

(R)-2-((S)-1-Methoxy-2-morpholin-4-yl-2-oxo-ethyl)-5-phenyl-pentanoic acid[(S)-1-(benzoxazole-2-carbonyl)-butyl]-amide

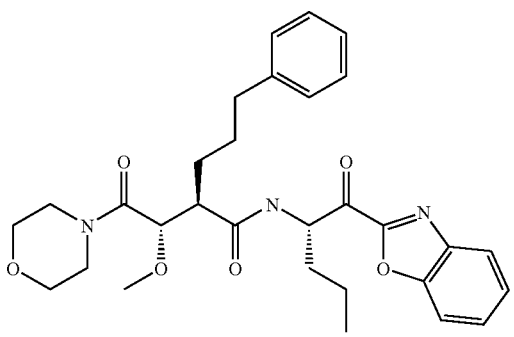

It is similarly prepared according to the procedure for Example 34.

¹H NMR (CDCl₃) δ 0.98 (t, 3H), 2.18–1.46 (m, 2+2+2H), 2.74–2.52 (m, 1+2H), 3.34 (s, 3H), 3.78–3.52 (m, 8H), 4.32 (d, 1H), 5.80–5.70 (m, 1H), 6.56 (d, 1H), 7.36–7.14 (m, 5H), 7.62–7.46 (m, 2H), 7.68 (m, 1H), 7.92 (m, 1H);

LCMS: RT=3.37 min. M+1=536

EXAMPLE 37

2-(2-Morpholin-4-yl-2-oxo-ethyl)-5-phenyl-pentanoic acid[(S)-1-(oxazole-2-carbonyl)-propyl]-amide

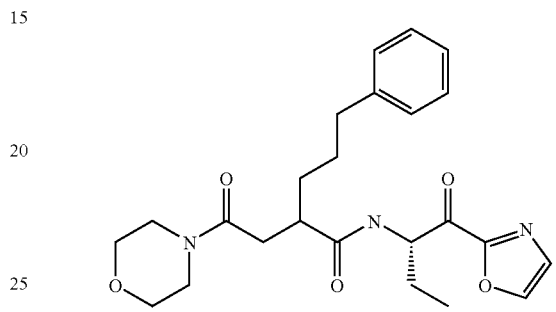

It is similarly prepared according to the general procedure for Example 10 using (S)-2-Amino-1-oxazol-2-yl-butan-1-one; hydrochloride as the amino component and 2-(2-Morpholin-4-yl-2-oxo-ethyl)-5-phenyl-pentanoic acid as the acidic component but without further oxidation.

LCMS: RT=2.86 min. M+1=442

EXAMPLE 38

(R)-2-((S)-1-Hydroxy-2-morpholin-4-yl-2-oxo-ethyl)-5-phenyl-pentanoic acid[(S)-1-(oxazole-2-carbonyl)-propyl]-amide

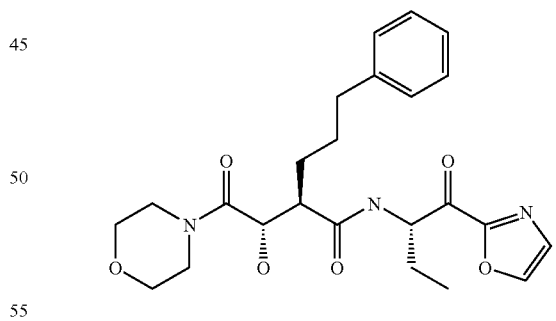

It is similarly prepared according to the general procedure for Example 10 using (S)-2-Amino-1-oxazol-2-yl-butan-1-one; hydrochloride as the amino component and (R)-2-((S)-1-Hydroxy-2-morpholin-4-yl-2-oxo-ethyl)-5-phenyl-pentanoic acid as the acidic component but without further oxidation.

¹H NMR (CDCl₃) δ 1.0 (t, 3H), 2.22–1.64 (m, 2+2+2H), 2.75–2.55 (m, 2+1H), 3.75–3.45 (m, 8H), 4.44 (m, 1H), 4.98–4.64 (b, 1H), 5.55–5.45 (m, 1H), 6.98–6.72 (m, 1H), 7.34–7.15 (m, 5H), 7.38 (d, 1H), 7.84 (d, 1H).

MS: 458 (M⁺).

EXAMPLE 39

(R)-5-(2-Difluoromethoxy-phenyl)-2-((S)-1-hydroxy-2-morpholin-4-yl-2-oxo-ethyl)-pentanoic acid [(S)-1-(oxazole-2-carbonyl)-propyl]-amide

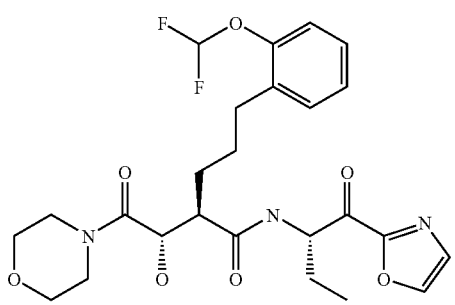

It is similarly prepared according to the general procedure for Example 10 using (S)-2-Amino-1-oxazol-2-yl-butan-1-one; hydrochloride as the amino component and (R)-5-(2-Difluoromethoxy-phenyl)-2-((S)-1-hydroxy-2-morpholin-4-yl-2-oxo-ethyl)-pentanoic acid as the acidic component but without further oxidation step.

$^1$H NMR (CDCl$_3$) δ 1.2 (t, 3), 2.22–1.164 (m, 2+2+2H), 2.75–2.55 (m, 2+1H), 3.75–3.45 (m, 8H), 4.38–4.10 (b, 1H), 4.44 (m, 1H), 5.55–5.45 (m, 1H), 6.80–6.28 (t, 1H), 7.08–7.70) (m, 1H), 726–7.10 (m, 4H), 7.38 (d, 1H), 7.85 (d, 1H).

MS: 524 (M$^+$).

EXAMPLE 40

2-(1-Methyl-cyclopentylmethyl)-4-morpholin-4-yl-N-[1-(oxazolo[4,5-b]pyridine-2-carbonyl)-propyl]-4-oxo-butyramide

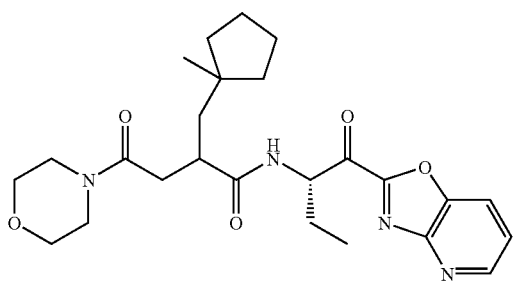

2-(1-Methyl-cyclopentylmethyl)-4-morpholin-4-yl-4-oxo-butyric acid (100 mg, 0.35 mmol) was combined with EDC (250 mg, 1.3 mmol), HOBt (250 mg, 1.6 mmol), and (2S)-2-amino-1-oxazolo[4,5-b]pyridin-2-yl-butan-1-ol (100 mg, 0.48 mmol). Dichloromethane (4 mL) was added and then 4-methylmorpholine (0.5 mL). The mixture was stirred at ambient temperature for 2 hours. After dilution with ethyl acetate (150 mL), the solution was washed with 1N aqueous HCl, water, saturated aqueous NaHCO$_3$ solution and brine, dried with MgSO$_4$ and evaporated under vacuum. The crude product was dissolved in dry dichloromethane (10 mL) and Dess-Martin Periodinane (500 mg, 1.2 mmol) was added. After stirring at ambient temperature for 1 hour, the mixture was diluted with ethyl acetate (150 mL) and treated with 0.26M Na$_2$S$_2$O$_3$ solution in saturated aqueous NaHCO$_3$. The organic phase was washed with saturated aqueous NaHCO$_3$ and brine, dried with MgSO$_4$ and evaporated. The product was purified by flash chromatography on silica gel (hexane/ethyl acetate 1:1) to yield the title compound (40 mg; 0.085 mmol) as a mixture of diastereomers.

LC-MS: elution time diastereomer 1=3.90 min. 469.6(M−1), 471.4(M+1). Elution time diastereomer 2=3.97 min. 469.6(M−1), 471.4(M+1). (MS: API 150EX. LC: HP Agilent 1100 Series. Column: Phenomenex, 5u ODS3 100A 100×3 mm.; Flow Rate: 2 ml/min. Two solvent gradient: Solvent A, 99% water, 1% acetonitrile, 0.1% AcOH. Solvent B, 99% acetonitrile, 1% water, 0.1% AcOH. Gradient from 100% A, 0% B to 0% A, 100% B from t=0 to t=6 min. Then gradient back to 100% A, 0% B from t=7 to t=15 min.)

EXAMPLE 41

(S)-3-(4-Morpholin-4-yl-4-oxo-2-phenylmethane-sulfonylmethyl-butyrylamino)-2-oxo-pentanoic acid (pyridin-4-ylmethyl)-amide

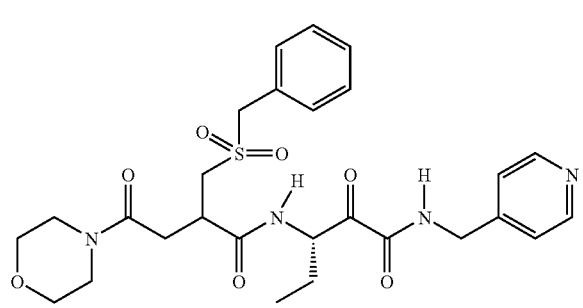

The synthesis was performed in analogy to Harbeson, S. L. et al. *J. Med. Chem.* 1994, 37, 2918–2929.

$^1$H NMR (CDCl$_3$) δ 8.5–8.4(m, 2H), 7.5–7.0 (m, 9H), 5.05 (m, 1H), 4.6–4.0 (m, 4H), 3.7–3.1(m, 7H), 2.9–2.5(m, 2H), 2.1–1.9(m, 2H), 1.8–1.5(m, 2H), 1.3–1.0(m, 2H), 1.0–0.8(m, 3H).

MS: 559 (MH$^+$).

EXAMPLE 42

(S)-3-(4-Morpholin-4-yl-4-oxo-2-phenylmethane-sulfonylmethyl-butyfylamino)-2-oxo-pentanoic acid diethylamide

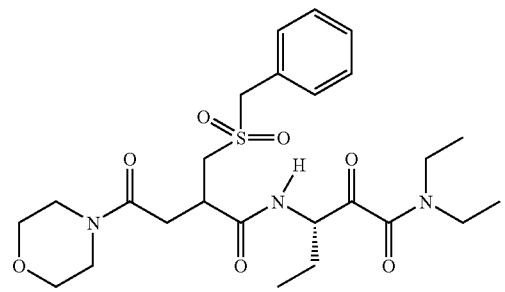

The synthesis was performed in analogy to Harbeson, S. L. et al. *J. Med. Chem.* 1994, 37, 2918–2929.

$^1$H NMR (CDCl$_3$) δ 7.37–7.19(m, 6H), 4.7–4.59 (m, 1H), 4.25–4.1 (m, 2H), 3.6–3.05 (m, 13H), 2.96–2.55 (m, 3H), 1.8–1.7 (m, 2H), 1.3–0.8 (m, 10H).

MS: 525 (MH$^+$), 546 (M+Na).

EXAMPLE 43

N-((S)-1-Ethyl-2,3-dioxo-3-pyrrolidin-1-yl-propyl)-4-morpholin-4-yl-4-oxo-2-phenylmethanesulfonylm-ethyl-butyramide

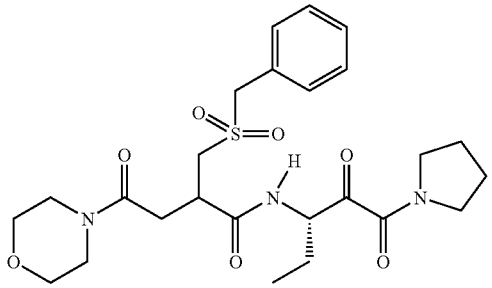

The synthesis was performed in analogy to Harbeson, S. L. et al. *J. Med. Chem.* 1994, 37, 2918–2929.

$^1$H NMR (CDCl$_3$) δ 7.2–7.0 (m, 6H), 4.7 (m, 1H), 4.2 (m, 2H), 3.6–3.2 (m, 10H), 2.95 (m, 1H), 2.85–2.6 (m, 2H), 2.0–1.3 (m, 7H), 1.3–1.1 (m, 3H), 1.0–0.8 (m, 3H).

MS: 522 (MH$^+$), 544 (M+Na).

EXAMPLE 44

(S)-3-(4-Morrpholin-4-yl-4-oxo-2-phenylmethane-sulfonylmethyl-butyralamino)-2-oxo-pentanoic acid phenethyl-amide

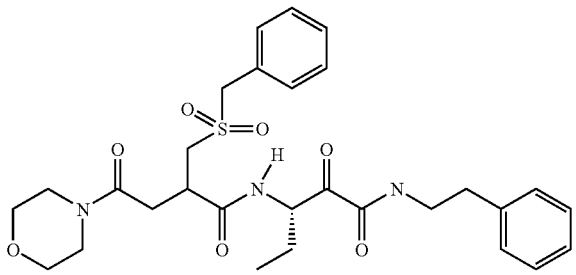

The synthesis was performed in analogy to Harbeson, S. L. et al. *J. Med. Chem.* 1994, 37, 2918–2929.

$^1$H NMR (CDCl$_3$) δ 7.4–6.8 (m, 12H), 5.15 (m, 1H), 4.25–4.15 (m, 2H), 3.6–3.2 (m, 12H), 2.94–2.5 (m, 5H), 2.0–1.8 (m, 1H), 1.65–1.55 (m, 1H), 0.90–0.8 (m, 3H).

MS: 572, 596.

EXAMPLE 45

(S)-3-(4-Moripholin-4-yl-4-oxo-2-phenylmethane-sulfonylmethyl-butyrylamino)-2-oxo-pentanoic acid (2-pyridin-2-yl-ethyl)-amide

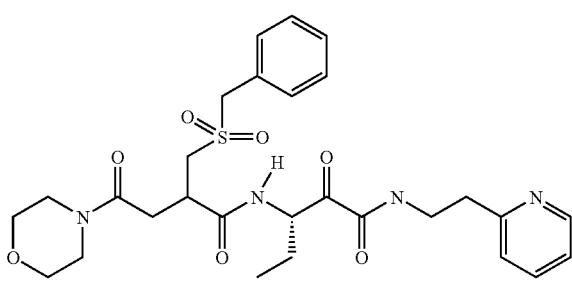

The synthesis was performed in analogy to Harbeson, S. L. et al. *J. Med. Chem.* 1994, 37, 2918–2929.

$^1$H NMR (CDCl$_3$) δ 8.51 (m, 1H), 7.86 (m, 1H), 7.5 (m, 1H), 7.4–7.1 (m, 7H), 5.2 (m, 1H), 4.3–4.2 (m, 3H), 3.8–3.3 (m, 9H), 3.1–2.6 (m, 4H), 2.0 (m, 2H), 1.7 (m, 2H), 0.90 (m, 3H).

MS: 573 (MH$^+$).

EXAMPLE 46

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM). Human cathepsin S (0.158 pMoles in 25 μL of assay buffer) was added to the dilutions. The assay solutions were mixed for 5–10 seconds on a shaker plate, covered and incubated for 30 minutes at ambient temperature. Z-Val-Val-Arg-AMC (9 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models. Based on essays carried out by Applicants, the following compounds showed a Ki value below 100 nM:

2-(2-Methyl-propane-1-sulfonylmethyl)-4-morpholin-4-yl-4-oxo-N-[(S)-1-(5-phenyl-1,2,4-oxadiazole-3-carbonyl)-propyl]-butyramide, (R)-4-Morpholin-4-yl-4-oxo-2-phenylmethanesulfonylm-ethyl-N-[1-(3-phenyl-1,2,4-oxadiazole-5-carbonyl)-propyl]-butyramide, N-[(S)-1-(Benzoxazole-2-carbonyl)-butyl]-2-(1-benzyl-cyclopropylmethyl)-4-morpholin-4-yl-4-oxo-butyramide, N-[(S)-1-(Benzoxazole-2-carbonyl)-butyl]-4-morpholin-4-yl-4-oxo-2-(2-phenyl-cyclopropylmethyl)-butyramide, (R)-4,4-Dimethyl-2-(2-morpholin-4-yl-2-oxo-ethyl)-pentanoic acid[(S)-1-(benzoxazole-2-carbonyl)-butyl]-amide, (R)-4,4-Dimethyl-2-(2-morpholin-4-yl-2-oxo-ethyl)-pentanoic acid[1-(3-phenyl-1,2,4-oxadiazole-5-carbonyl)-propyl]-amide, (R)-4,4-Dimethyl-2-(2-morpholin-4-yl-2-oxo-ethyl)-5-phenyl-pentanoic acid[1-(3-phenyl-1,2,4-oxadiazole-5-carbonyl)-propyl]-amide, 4,4-Dimethyl-2-(2-morpholin-4-yl-2-oxo-ethyl)-5-phenyl-pentanoic acid[(S)-1-(benzoxazole-2-carbonyl)-butyl]-amide, 2-(2-Morpholin-4-yl-2-oxo-ethyl)-5-phenyl-pentanoic acid [(S)-1-(oxazole-2-carbonyl)-3-phenyl-propyl]-amide (mixture of diastereoisomers), 4-Morpholin-4-yl-N-[1-(oxazole-2-carbonyl)-3-phenyl-propyl]-4-oxo-2-(2-phenyl-cyclopropylmethyl)-butyramide (mixture of diastereoisomers), (R)-2-Cyclohexylmethyl-4-morpholin-4-yl-N-[(S)-1-(oxazole-2-carbonyl)-3-phenyl-propyl]-4-oxo-butyramide, (R)-4,4,6-Trimethyl-2-(2-morpholin-4-yl-2-oxo-ethyl)-heptanoic acid[(S)-1-(benzoxazole-2-carbonyl)-butyl]-amide, (R)-2-((S)-1-Hydroxy-2-morpholin-4-yl-2-oxo-ethyl)-5-phenyl-pentanoic acid[(S)-1-(oxazole-2-carbonyl)-3-phenyl-propyl]-amide, (S)-2-(1-Fluoro-2-morpholin-4-yl-2-oxo-ethyl)-5-phenyl-pentanoic acid[(S)-1-(benzoxazole-2-carbonyl)-butyl]-amide, and (R)-2-((S)-1-Methoxy-2-morpholin-4-yl-2-oxo-ethyl)-5-phenyl-pentanoic acid[(S)-1-(benzoxazole-2-carbonyl)-butyl]-amide.

EXAMPLE 47

Cathepsin B Assay

Solutions of test compounds in varying concentrations were prepared in 10 μL of dimethyl sulfoxide (DMSO) and then diluted into assay buffer (40 μL, comprising: N,N-bis (2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5–10 seconds on a shaker plate, covered and incubated for 30 minutes at ambient temperature. Z-FR-AMC (20 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

EXAMPLE 48

Cathepsin K Assay

Solutions of test compounds in varying concentrations were prepared in 10 VL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at ambient temperature. Z-Phe-Arg-AMC (4 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

EXAMPLE 49

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5–10 seconds on a shaker plate, covered and incubated for 30 minutes at ambient temperature. Z-Phe-Arg-AMC (1 nMoles in 25 μL of assay buffer) was added to the assay solutions and hydrolysis was followed spectrophotometrically at (λ460 nm) for 5 minutes. Apparent inhibition constants ($K_i$) were calculated from the enzyme progress curves using standard mathematical models.

EXAMPLE 50

Representative Pharmaceutical Formulations Containing a Compound of Formula I, II or III

| ORAL FORMULATION | |
| --- | --- |
| Compound of Formula I, II or III | 10–100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
| --- | --- |
| Compound of Formula I, II or III | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
| --- | --- |
| Compound of Formula I, II or III | 1% |
| Microcrystalline Cellulose | 73% |
| Stearic Acid | 25% |
| Colloidal Silica | 1%. |

While there have been described and pointed out fundamental novel features of the invention as applied to a preferred embodiment thereof, it will be understood that various omissions and substitutions and changes, in the form and details of the composition and methods illustrated, may be made by those skilled in the art without departing from the spirit of the invention. For example, it is expressly intended that chemical radical substitutions and/or method steps which perform substantially the same function in substantially the same way to achieve the same results are within the scope of the invention.

The invention is not limited by the embodiments described above which a represented as examples only but can be modified in various ways within the scope of protection defined by the appended patent claims.

We claim:
1. A compound of formula I,

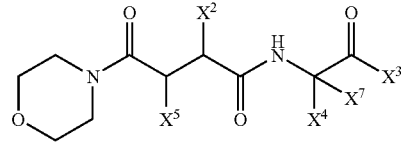

wherein $X^2$ is a sulfonyl alkyl motif selected from the group consisting of,

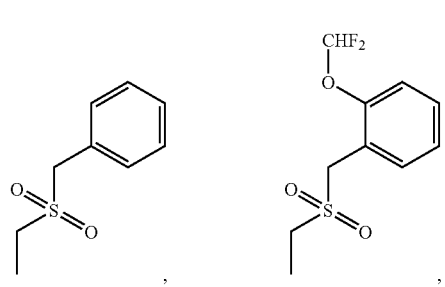

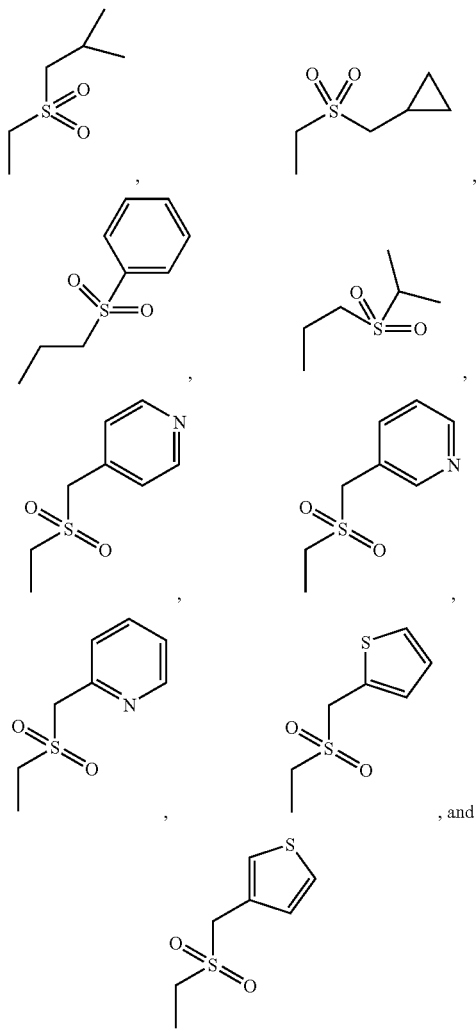

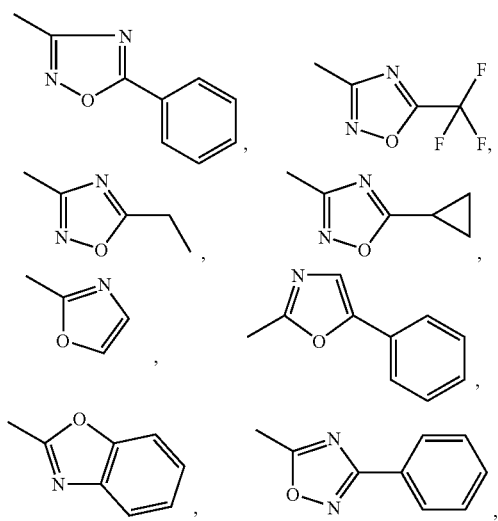

$X^3$ is a heterocyclic motif or an amide motif, wherein the heterocyclic motif is selected the group consisting of

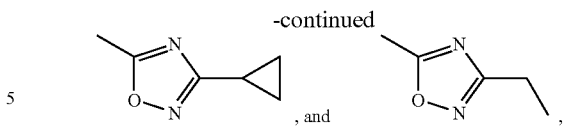

and the amide motif is selected from the group consisting of $X^7$ is —H, $X^4$ is an alkyl group with straight or branched-chain containing 1–4 carbon atoms or and $X^5$ is —H, —F, —OH, or —O—R, and R is an alkyl group with straight or branched-chain containing 1–6 carbon.

2. A compound of claim 1, wherein $X^5$ is —H.

3. A compound of claim 2, wherein $X^4$ is —CH$_2$CH$_3$, —CH$_2$CH$_2$CH$_3$—C(CH$_3$)$_3$ or 4. A compound selected from the group consisting of:
2-(2-Methyl-propane-1-sulfonylmethyl)-4-morpholin-4-yl-4-oxo-N-[(S)-1-(5-phenyl-1,2,4-oxadiazole-3-carbonyl)-propyl]-butyramide,
4-Morpholin-4-yl-4-oxo-2-phenylmethanesulfonylmethyl-N-[(S)-1-(5-trifluoromethyl-1,2,4-oxadiazole-3-carbonyl)-propyl]-butyramide,
(R)-2-(2-Methyl-propane-1-sulfonylmethyl)-4-morpholin-4-yl-4-oxo-N-[(S)-1-(3-phenyl-1,2,4-oxadiazole-5-carbonyl)-propyl]-butyramide,
N-[(S)-1-(5-Ethyl-1,2,4-oxadiazole-3-carbonyl)-propyl]-4-morpholin-4-yl-4-oxo-2-phenylmethanesulfonylmethyl-butyramide,
(R)-4-Morpholin-4-yl-4-oxo-2-phenylmethanesulfonylmethyl-N-[(S)-1-(3-phenyl-1,2,4-oxadiazole-5-carbonyl)-propyl]-butyramide,
(R)-4-Morpholin-4-yl-4-oxo-2-phenylmethanesulfonylmethyl-N-[1-(3-phenyl-1,2,4-oxadiazole-5-carbonyl)-propyl]-butyramide,
(R)-N-[(S)-1-(3-Cyclopropyl-1,2,4-oxadiazole-5-carbonyl)-propyl]-2-(2-methyl-prapane-1-sulfonylmethyl)-4-morpholin-4-yl-4-oxo-butyramide,
(R)-2-Cyclopropylmethanesulfonylmethyl-N-[(S)-1-(3-cyclopropyl-1,2,4-oxadiazole-5-carbonyl)-propyl]-4-morpholin-4-yl-4-oxo-butyramide,
(R)-N-[(S)-1-(3-Ethyl-1,2,4-oxadiazole-5-carbonyl)-propyl]-2-(2-methyl-propane-1-sulfonylmethyl)-4-morpholin-4-yl-4-oxo-butyramide,
(R)-2-Cyclopropylmethanesulfonylmethyl-N-[(S)-1-(3-ethyl-1,2,4-oxadiazole-5-carbonyl)-propyl]-4-morpholin-4-yl-4-oxo-butyramide,
(S)-2-(2-Benzenesulfonyl-ethyl)-N-[(S)-1-(3-ethyl-1,2,4-oxadiazole-5-carbonyl)-propyl]-4-morpholin-4-yl-4-oxo-butyramide,
(S)-N-[(S)-1-(3-Ethyl-1,2,4-oxadiazole-5-carbonyl)-propyl]-4-morpholin-4-yl-4-oxo-2-[2-(propane-2-sulfonyl)-ethyl]-butyramide, (S)-3-(4-Morpholin-4-yl-4-oxo-2-phenylmethanesulfo-nylmethyl-butyrylamino)-2-oxo-pentanoic acid (pyridin-4-ylmethyl)-amide,
(S)-3-(4-Morpholin-4-yl-4-oxo-2-phenylmethanesulfo-nylmethyl-butyrylamino)-2-oxo-pentanoic acid diethylamide,
(S)-3-(4-Morpholin-4-yl-4-oxo-2-phenylmethanesulfo-nylmethyl-butyrylamino)-2-oxo-pentanoic acid phenethyl-amide, and
(S)-3-(4-Morpholin-4-yl-4-oxo-2-phenylmethanesulfo-nylmethyl-butyrylamino)-2-oxo-pentanoic acid (2-pyridin-2-yl-ethyl)-amide.

5. A compound selected from the group consisting of:
2-(2-Methyl-propane-1-sulfonylmethyl)-4-morpholin-4-yl-4-oxo-N-[(S)-1-(5-phenyl-1,2,4-oxadiazole-3-carbonyl)-propyl]-butyramide and
(R)-4-Morpholin-4-yl-4-oxo-2-phenylmethanesulfonyl-methyl-N-[(1-(3-phenyl-1,2,4-oxadiazole-5-carbonyl)-propyl]-butyramide.

6. A compound derived from a compound of claim 1, which is an N-oxide derivative of, an prodrug of, a protected derivative of, an isomer of, an mixture of isomers of, or a pharmaceutically acceptable salt or solvate of a compound of claim 1.

7. A compound derived from a compound of claim 4 or claim 5, which is an N-oxide derivative of, an prodrug of, a protected derivative of, an isomer of, an mixture of isomers of, or a pharmaceutically acceptable salt or solvate of a compound of claim 4 or claim 5.

8. A pharmaceutical composition comprising a therapeutically effective amount of a compound of claim 1 or a compound of claim 6, in combination with a pharmaceutically acceptable excipient.

9. A pharmaceutical composition comprising a therapeutically effective amount of a compound of claim 4 in combination with a pharmaceutically acceptable excipient.

* * * * *